US012558035B2

(12) United States Patent
Matsimanis et al.

(10) Patent No.: US 12,558,035 B2
(45) Date of Patent: Feb. 24, 2026

(54) SYSTEMS FOR DETECTING FIT OF A WEARABLE DEVICE ON A USER BY MEASURING THE CURRENT DRAW TO AMPLIFY A BIOPOTENTIAL SIGNAL SENSOR AND METHOD OF USE THEREOF

(71) Applicant: Meta Platforms Technologies, LLC, Menlo Park, CA (US)

(72) Inventors: Peter Andrew Matsimanis, Menlo Park, CA (US); Igor Gurovski, Mountain View, CA (US); Tahir Turan Caliskan, Lund (SE); Pascal Alexander Bentioulis, Malmo (SE); Per-Erik Bergström, Malmo (SE); Muhammed Talha Agcayazi, Bothell, WA (US); Murat Yokus, Kirkland, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 190 days.

(21) Appl. No.: 18/503,142

(22) Filed: Nov. 6, 2023

(65) Prior Publication Data

US 2024/0148331 A1 May 9, 2024

Related U.S. Application Data

(60) Provisional application No. 63/488,142, filed on Mar. 2, 2023, provisional application No. 63/382,701, filed on Nov. 7, 2022.

(51) Int. Cl.
| | |
|---|---|
| *A61B 5/00* | (2006.01) |
| *A61B 5/251* | (2021.01) |
| *A61B 5/26* | (2021.01) |

(52) U.S. Cl.
CPC ............ *A61B 5/7221* (2013.01); *A61B 5/251* (2021.01); *A61B 5/26* (2021.01); *A61B 5/681* (2013.01);
(Continued)

(58) Field of Classification Search
CPC ......... A61B 5/7221; A61B 5/251; A61B 5/26; A61B 5/681; A61B 5/6824; A61B 5/683; A61B 5/742; A61B 5/6843
See application file for complete search history.

(56) References Cited

U.S. PATENT DOCUMENTS

| | | | | |
|---|---|---|---|---|
| 11,890,083 B1 * | 2/2024 | Williams | ............... | A61B 5/681 |
| 2020/0146629 A1 * | 5/2020 | Sun | ........................ | A61B 5/7221 |
| 2021/0022678 A1 * | 1/2021 | Langer | ............... | A61B 5/02416 |

* cited by examiner

*Primary Examiner* — Eugene T Wu
(74) *Attorney, Agent, or Firm* — Morgan, Lewis & Bockius LLP

(57) ABSTRACT

An example method for securing a wearable device to a user occurs while the wearable device is worn around a body part. The wearable device includes a biopotential-signal sensor connected to an amplifier to adjust amplification of biopotential signal. The method includes receiving first information representative of power needed to amplify the biopotential signal to the particular amplitude for signal processing. The method also includes, in accordance with a determination that the first information indicates that the wearable device is not properly affixed to the body part, providing first instructions to adjust how the wearable device is affixed to the body part. The method includes receiving second information, and, in accordance with a determination that the second information indicates that the
(Continued)

wearable device is properly affixed to the body part, forgo-
ing providing second instructions to adjust how the wearable
device is affixed to the body part.

19 Claims, 23 Drawing Sheets

(52) U.S. Cl.
CPC ............ *A61B 5/6824* (2013.01); *A61B 5/683*
(2013.01); *A61B 5/742* (2013.01)

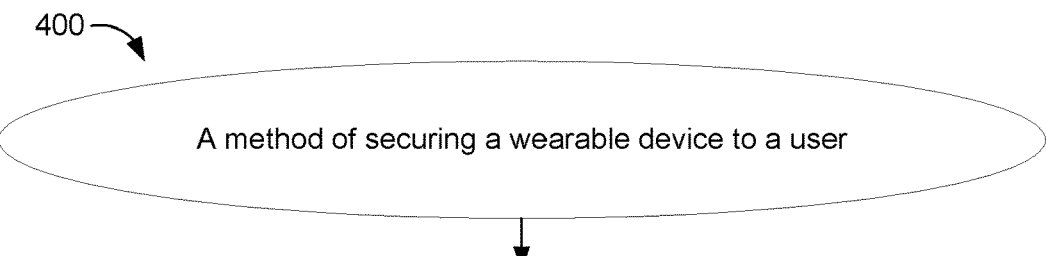

A method of securing a wearable device to a user

While the wearable device is worn around a body part, the wearable device including a neuromuscular-signal sensor configured to receive a neuromuscular signal and the neuromuscular-signal sensor is connected to an amplifier to adjust amplification of the neuromuscular signal to a particular amplitude for signal processing:

Receiving first information representative of power needed to amplify the neuromuscular signal to the particular amplitude for signal processing In accordance with a determination that the first information representative of the power needed to amplify the neuromuscular signal to the particular amplitude for signal processing indicates that the wearable device is not properly affixed to a body part of a user, providing first instructions to adjust how the wearable device is affixed to the wrist of a user Receiving second information representative of power needed to amplify the neuromuscular signal to the particular amplitude for signal processing In accordance with a determination that the second information representative of the power needed to amplify the neuromuscular signals to the particular amplitude for signal processing indicates that the wearable device is properly affixed to the wrist of the user, forgoing providing second instructions to adjust how the wearable device is affixed to the body part of the user

Figure 4

VR device 710

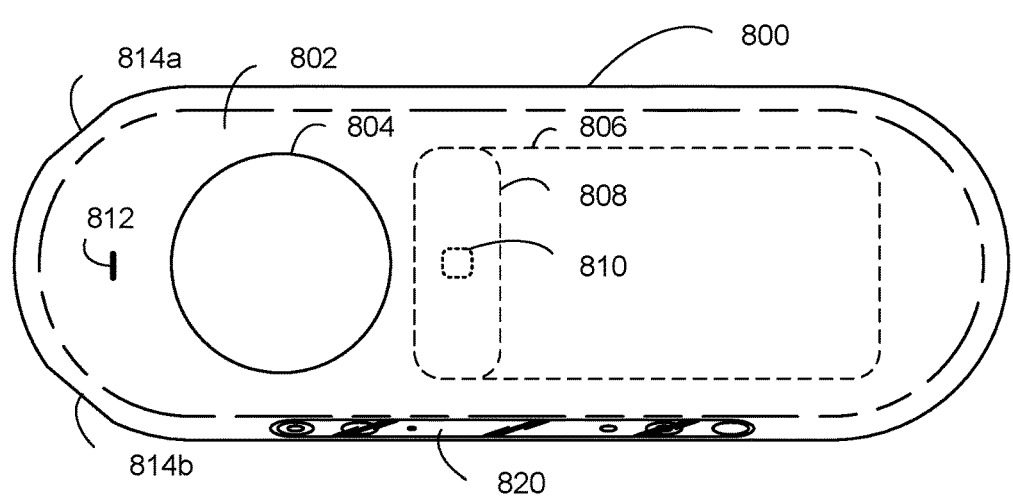
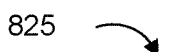
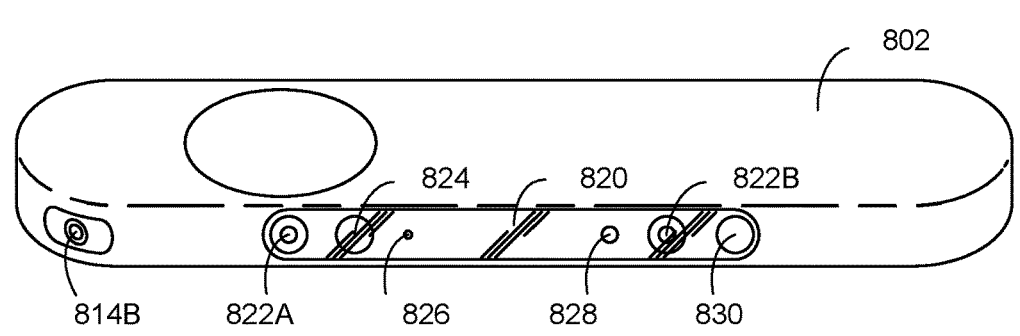
Figure 8A

Computer System — 840

800

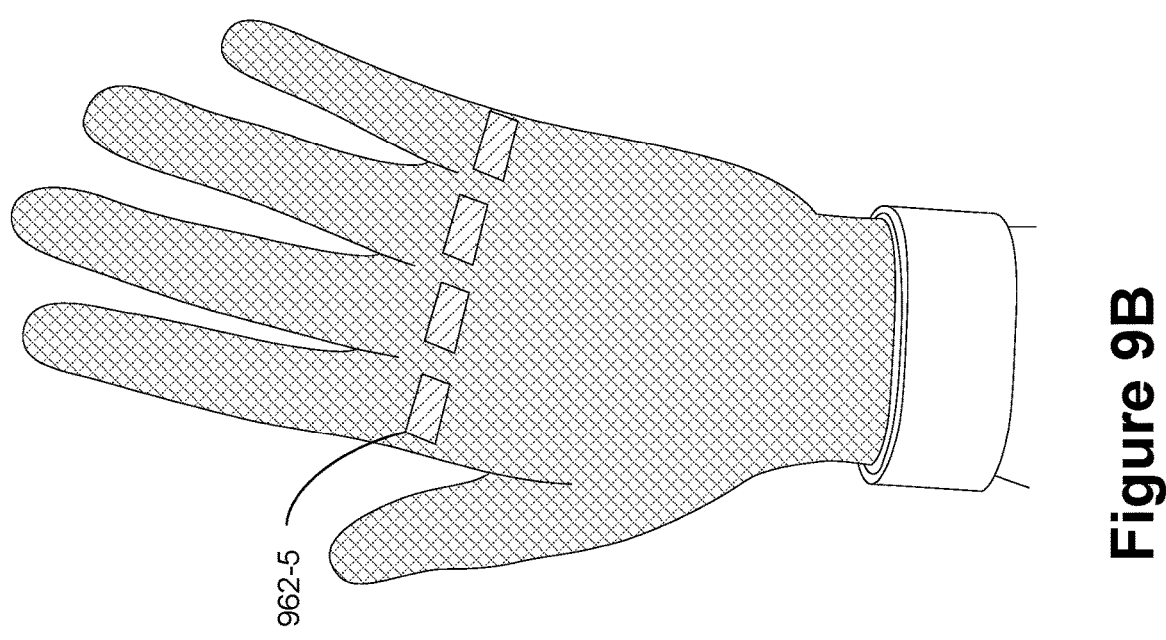
962-5
Figure 9B
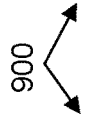
900
962-1
962-2
962-3
904
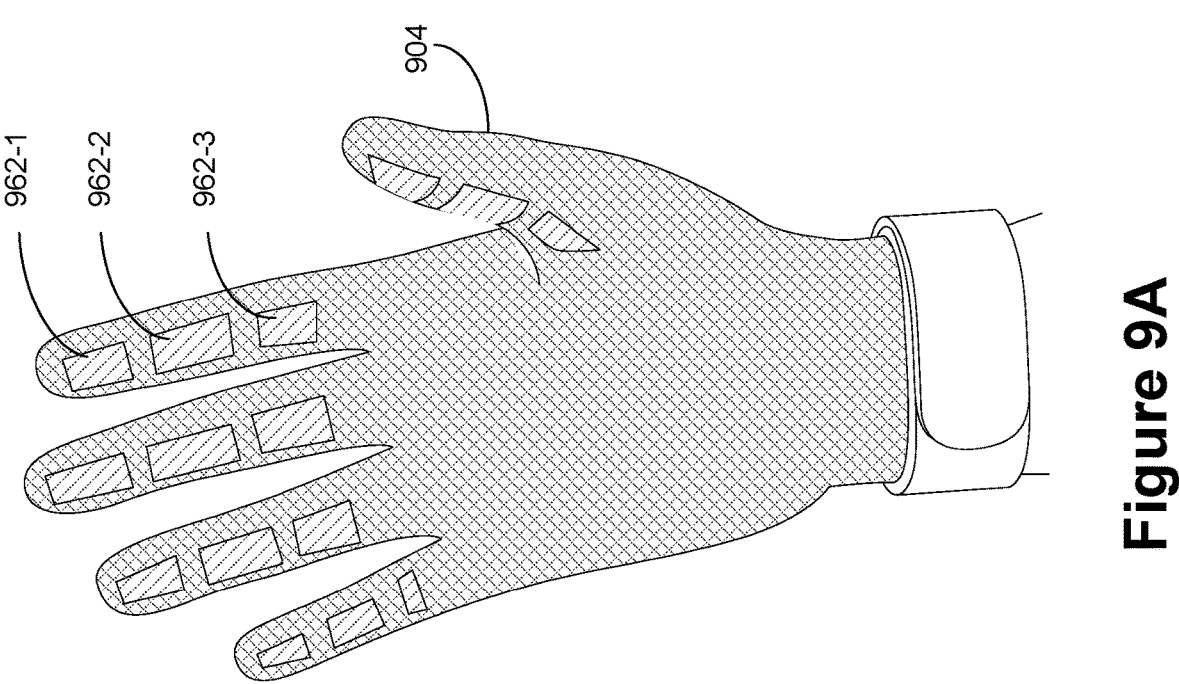
Figure 9A

1

SYSTEMS FOR DETECTING FIT OF A WEARABLE DEVICE ON A USER BY MEASURING THE CURRENT DRAW TO AMPLIFY A BIOPOTENTIAL SIGNAL SENSOR AND METHOD OF USE THEREOF

RELATED APPLICATIONS

This application claims priority to U.S. Provisional Application No. 63/382,701, filed Nov. 7, 2022; and U.S. Provisional Application No. 63/488,142 filed Mar. 2, 2023, each of which is incorporated by reference herein.

TECHNICAL FIELD

This application relates generally to wearable devices (e.g., wrist-wearable devices), including, detecting a fit characteristic of the wearable device on a user by using a measurements associated with an already existing sensor that is part of the wearable device (e.g., by monitoring how much current is needed to amplify a biopotential signal, it can be determined whether the sensor is properly affixed to a user and if an adjustment of the wearable device is required). This application also generally relates to adjusting biopotential signals received from a biopotential sensor based on data received from other sensors, such as an optical sensor.

BACKGROUND

Wearable electronic devices, such as wrist-wearable electronic devices (e.g., smart watches) and head-wearable devices (e.g., artificial-reality (AR) glasses, virtual-reality (VR) goggles, etc.) are gaining popularity, and users are gradually integrating more of such wearable devices into their everyday lives. While there are many positive aspects of such wearable electronic devices, there are also constraints and unresolved issues. For example, these devices require a certain fit on the user to function properly, and when the fit is improper the user experience can be degraded (e.g., allowing sensors to operate optimally). Further, these wearable devices need to remain comfortable, so adding additional components to check for fit issues can also impair comfort (e.g., by making the device heavier or more cumbersome to use) and reduce battery life in these wearable devices.

Improved ways of determining whether a wearable device is properly fitted to a user are thus needed, so users can comfortably wear the wearable device while also ensuring that the user experience is not degraded.

Certain devices also require a very specific type of wear characteristic in order to operate properly (i.e., the sensor has to be tightly secured). Having specific wear characteristics are inconvenient for the user and not always listened to which can be problematic for incoming data.

SUMMARY

The embodiments discussed herein address one or more of the problems and drawbacks discussed above, for example, by determining how much current is being drawn to amplify a signal from a biopotential signal sensor, it can be determined whether the biopotential signal sensor is properly affixed to the user (e.g., a high current to amplify the signal correlates to poor contact of the biopotential signal sensor). In addition, by just monitoring the required amplification of the signal coming the biopotential signal sensor, there is no need for an additional sensor to determine if the fit is correct. By not having an additional sensor, the device becomes lighter, which is beneficial in wearable devices worn for an extended period of time. In some embodiments, when the signal is degraded, a higher current is required to amplify the signal, which also reduces battery life of the wearable device. Thus, there is an additional benefit of securing the wearable device properly, as it also results in a reduction power consumption, and thereby extends the battery life of the wearable device. This is especially apparent when the sensor is an electromyography (EMG) sensor. As will be discussed in detail below, the wearable device's fit determination is capable of reducing battery consumption and improving signal recording all while adding no new components to the wearable device.

A further summary of this first example method will now be provided. The example method describes that securing a wearable device to a user occurs while the wearable device is worn around a body part the wearable device, and the wearable device includes a biopotential-signal sensor configured to receive a biopotential signal. The biopotential-signal sensor is also connected to an amplifier to adjust amplification of the biopotential signal to a particular amplitude for signal processing. The method includes, receiving first information representative of power needed to amplify the biopotential signal to the particular amplitude for signal processing. The method also includes, in accordance with a determination that the first information representative of the power needed to amplify the biopotential signal to the particular amplitude for signal processing indicates that the wearable device is not properly affixed to a body part of a user. The method further includes, providing first instructions to adjust how the wearable device is affixed to the wrist of a user, and receiving second information representative of power needed to amplify the biopotential signal to the particular amplitude for signal processing. The method includes, in accordance with a determination that the second information representative of the power needed to amplify the biopotential signals to the particular amplitude for signal processing indicates that the wearable device is properly affixed to the wrist of the user, forgoing providing second instructions to adjust how the wearable device is affixed to the body part of the user.

In some embodiments, a computing system (e.g., an artificial-reality system that includes a wrist-wearable device and a head-wearable device) includes one or more processors, memory, one or more means (e.g., a display or projector) of presenting a user interface, and one or more programs stored in memory. The one or more programs are configured for execution by the one or more processors. The one or more programs include instructions for performing any of the methods described herein (e.g., the method 400).

In some embodiments, a non-transitory computer-readable storage medium stores one or more programs configured for execution by a computing device (e.g., a wrist-wearable device or a head-wearable device, or another connected device, such as a smartphone or desktop or laptop computer that can be configured to coordinate operations at the wrist-wearable device and the head-wearable device), having one or more processors, memory, and a display (in some embodiments, the display can be optional, such as for example certain connected devices that can coordinate operations to be performed at the wrist-wearable device and/or the head-wearable device, and thus have processing and power resources, but need not have their own displays). The one or more programs include instructions for performing (or causing performance of) any of the methods described herein (e.g., the method 400).

Turning to the issue identified above regarding receiving poor data because of specific wear characteristics not being followed, it is thus necessary for there to be a way to remove artifacts from biopotential signals that are a result of unintended movement caused by the wearable device being loosely worn by a user.

To that end, a solution using an optical sensor to detect movement is provided below. In one example, a wearable device can include a biopotential-signal sensor, and an optical sensor configured to detect optical data indicating changes in position of the biopotential-signal sensor (e.g., relative to a body part of the user (e.g., detecting moving about a wrist of a user). The wearable device can also include a processor (e.g., or more than one processor) configured to receive (i) biopotential-signal data from the biopotential-signal sensor and (ii) the optical data from the optical sensor. The processor is also configured to determine one or more motion artifacts in the biopotential-signal data based on the optical data. The processor is further configured to adjust the biopotential signal data based on the motion artifacts to produce corrected biopotential signal data.

Using the above techniques, erroneous signals can be removed without interfering with non-erroneous signals.

Thus, methods, systems, and computer-readable storage media are disclosed for detecting fit of a wearable device on a user by measuring the current draw to amplify a biopotential signal sensor. Such methods can complement or replace conventional methods for determining proper fit of a wearable device.

The features and advantages described in the specification are not necessarily all inclusive and, in particular, certain additional features and advantages will be apparent to one of ordinary skill in the art in view of the drawings, specification, and claims. Moreover, it should be noted that the language used in the specification has been principally selected for readability and instructional purposes.

Having summarized the above example aspects, a brief description of the drawings will now be presented.

BRIEF DESCRIPTION OF THE DRAWINGS

For a better understanding of the various described embodiments, reference should be made to the Detailed Description below, in conjunction with the following drawings in which like reference numerals refer to corresponding parts throughout the figures.

FIG. 1C shows an example interaction where the wearable device is properly affixed to a wrist of a user, in accordance with some embodiments.

FIGS. 3A and 3B illustrate a way of automatically adjusting the fit of the wearable device, in accordance with some embodiments.

FIG. 4 shows a flow chart of a method of securing a wearable device to a user, in accordance with some embodiments.

FIGS. 8A-8B illustrate an example handheld intermediary processing device, in accordance with some embodiments.

FIGS. 9A-9C illustrate an example smart textile-based garment, in accordance with some embodiments.

Figure 1A:
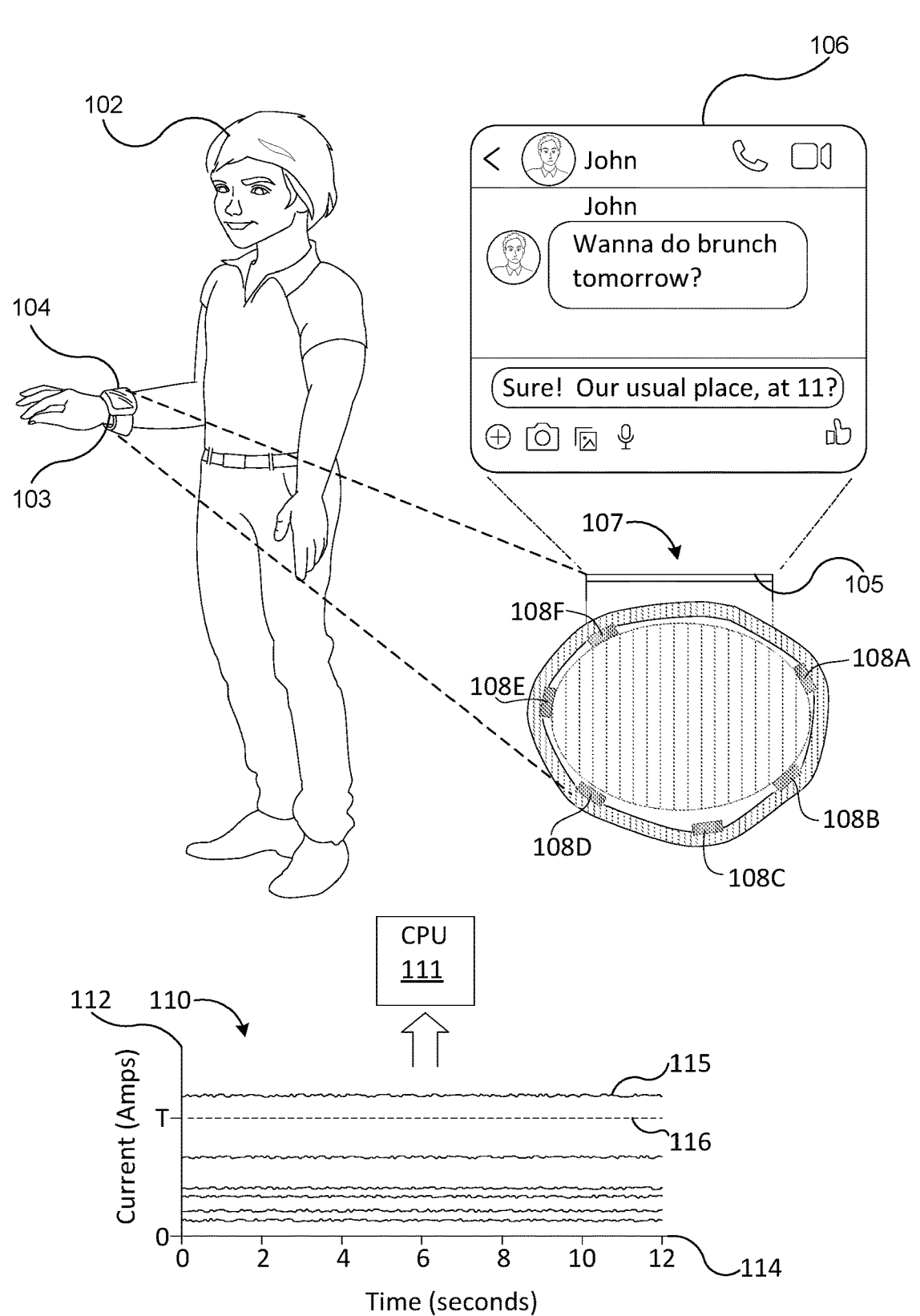
FIG. 1A shows an example interaction of securing a wearable device to a user, in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method, or device. Finally, like reference numerals may be used to denote like features throughout the specification and figures.

DETAILED DESCRIPTION

Numerous details are described herein to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not necessarily been described in exhaustive detail so as to avoid obscuring pertinent aspects of the embodiments described herein.

Embodiments of this disclosure can include or be implemented in conjunction with various types or embodiments of artificial-reality systems. Artificial-reality (AR), as described herein, is any superimposed functionality and or sensory-detectable presentation provided by an artificial-reality system within a user's physical surroundings. Such artificial-realities can include and/or represent virtual reality (VR), augmented reality, mixed artificial-reality (MAR), or some combination and/or variation one of these. For example, a user can perform a swiping in-air hand gesture to cause a song to be skipped by a song-providing API providing playback at, for example, a home speaker. An AR environment, as described herein, includes, but is not limited to, VR environments (including non-immersive, semi-immersive, and fully immersive VR environments); augmented-reality environments (including marker-based augmented-reality environments, markerless augmented-reality environments, location-based augmented-reality environments, and projection-based augmented-reality environments); hybrid reality; and other types of mixed-reality environments.

Artificial-reality content can include completely generated content or generated content combined with captured (e.g., real-world) content. The artificial-reality content can include video, audio, haptic events, or some combination thereof, any of which can be presented in a single channel or in multiple channels (such as stereo video that produces a three-dimensional effect to a viewer). Additionally, in some embodiments, artificial reality can also be associated with applications, products, accessories, services, or some combination thereof, which are used, for example, to create content in an artificial reality and/or are otherwise used in (e.g., to perform activities in) an artificial reality.

A hand gesture, as described herein, can include an in-air gesture, a surface-contact gesture, and or other gestures that can be detected and determined based on movements of a single hand (e.g., a one-handed gesture performed with a user's hand that is detected by one or more sensors of a wearable device (e.g., electromyography (EMG) and/or inertial measurement units (IMU)s of a wrist-wearable device) and/or detected via image data captured by an imaging device of a wearable device (e.g., a camera of a head-wearable device)) or a combination of the user's hands. In-air means, in some embodiments, that the user hand does not contact a surface, object, or portion of an electronic device (e.g., a head-wearable device or other communicatively coupled device, such as the wrist-wearable device), in other words the gesture is performed in open air in 3D space and without contacting a surface, an object, or an electronic device. Surface-contact gestures (contacts at a surface, object, body part of the user, or electronic device) more generally are also contemplated in which a contact (or an intention to contact) is detected at a surface (e.g., a single or double finger tap on a table, on a user's hand or another finger, on the user's leg, a couch, a steering wheel, etc.). The different hand gestures disclosed herein can be detected using image data and/or sensor data (e.g., neuromuscular signals sensed by one or more biopotential sensors (e.g., EMG sensors) or other types of data from other sensors, such as proximity sensors, time-of-flight sensors, sensors of an inertial measurement unit, etc.) detected by a wearable device worn by the user and/or other electronic devices in the user's possession (e.g., smartphones, laptops, imaging devices, intermediary devices, and/or other devices described herein).

Turning to the figures, FIG. 1A shows an example interaction of securing a wearable device to a user, in accordance with some embodiments. FIG. 1A shows a user 102 wearing a wearable device 104 on their wrist 103. The wearable device includes a display 105 (e.g., a touch-sensitive display or non-touch-sensitive display) that, in this example, is configured to display a messaging user interface 106. A cross-sectional view 107 of wearable device 104 and a wrist 103 is also shown. The cross-sectional view 107 illustrates that the wearable device 104 includes numerous sensors biopotential-signal sensors (e.g., biopotential-signal sensor 108A-108F). While six biopotential-signal sensors are shown in this example, it is possible for any number of sensors to be used (e.g., 1 to 'n' biopotential-signal sensor(s)). FIG. 1A also illustrates in cross-sectional view 107 that biopotential-signal sensor 108C is not in contact (or not secured tight enough) with the wrist 103 of a user 102.

FIG. 1A also shows a current over time chart 110, which illustrates the amount of respective current being sent to each biopotential-signal sensor over time. The current over time chart 110 shows the Y-axis 112 representing "current (Amps)" and the X-axis 114 representing "time (seconds)." When a biopotential-signal sensor is not in contact with a user's skin properly (e.g., contact patch is minimal, not enough pressure is applied, no contact at all with the wrist), the signal from the biopotential-signal sensor will be weak or non-existent. Accordingly, the wearable device instructs an amplifier to amplify this weak signal in order to retrieve usable data. Amplification of a signal requires current in this example, and thus a weak signal can be determined based on how much amplification (i.e., current) is applied/required. Thus, the amount of power needed to amplify the signal can be used as a proxy for determining, via a processor, whether the biopotential-signal sensor is fitted properly.

The current over time chart 110 illustrates the above scenario. The current over time chart 110 shows a line 115 that indicates that the biopotential-signal sensor 108C is consuming more current (e.g., has a higher power draw) than the other biopotential-signal sensors. While it is possible that not every biopotential-signal sensor will have the same current draw (e.g., due to unique human wrist structures), it is still possible to determine, via the processor, when a current draw is too high. For example, current over time chart 110 shows a threshold line 116 indicating a threshold amount of current being drawn is too great (e.g., too great of a power draw can be a power draw that significantly reduces battery life). In some embodiments, the threshold needs to be exceeded for set period of time before it is considered to be an issue with fit (e.g., 5, 10, 15, 30 seconds, etc.,). In some embodiments, if the threshold is repeatedly exceeded and then dips below the threshold, the fit may still be considered an issue. For example, when a user is running, the contact may be sufficient during only part of the running cadence of the user. FIG. 1A also illustrates a CPU 111 that can also function as a post-amplifier signal processing component (e.g., the CPU can read the amplified signals and perform determinations as to the state of fit of the wearable device).

Figure 1B:
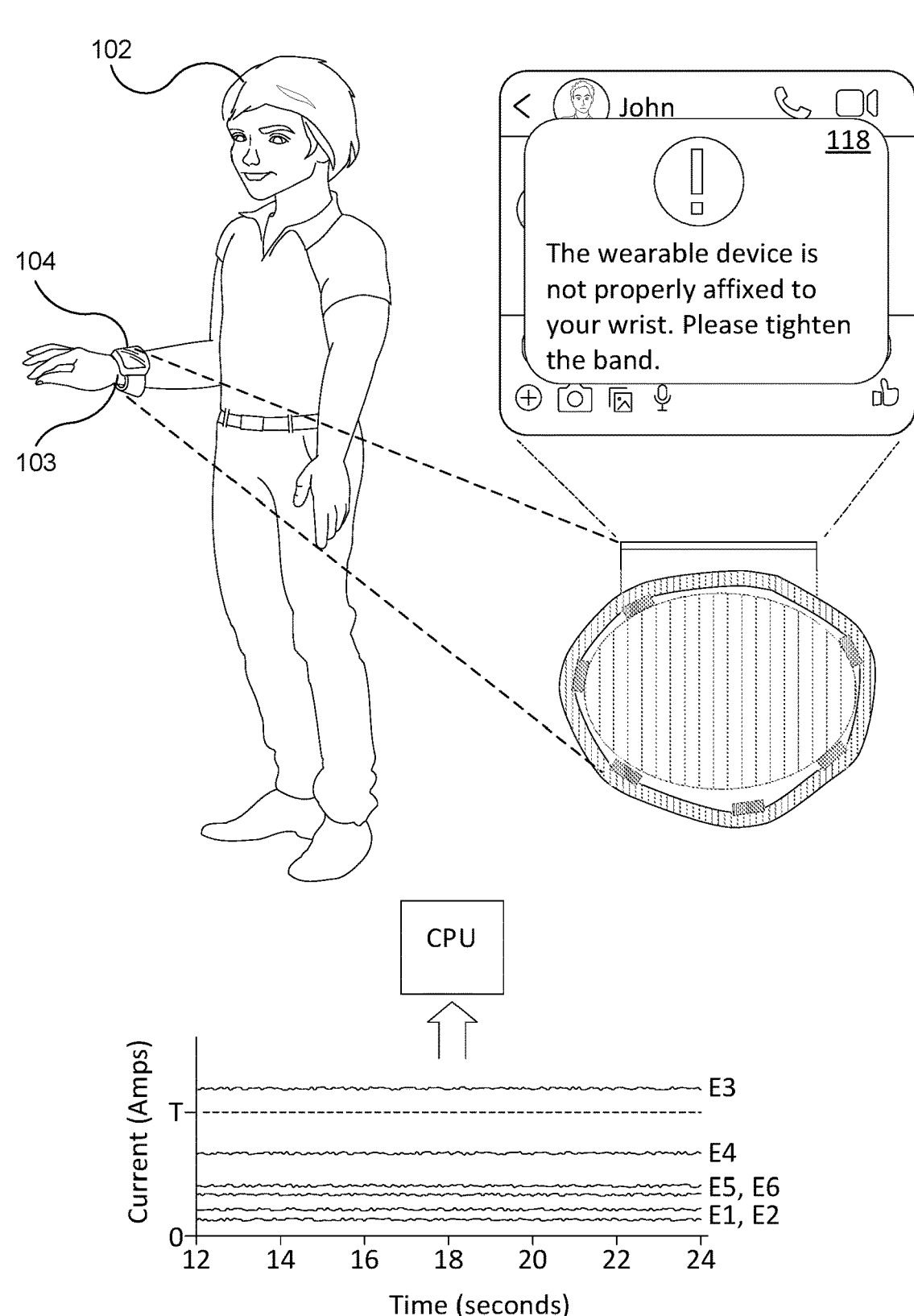
FIG. 1B shows an example interaction of securing a wearable device to a user when the fit of the wearable device on a wrist of the user is determined to be loose, in accordance with some embodiments.

FIG. 1B shows an example interaction of securing a wearable device to a user when the fit of the wearable device on a wrist of the user is determined to be loose, in accordance with some embodiments. FIG. 1B shows a notification 118 for providing an instructions to adjust how the wearable device 104 is affixed to the wrist 103 of a user 102. In this instance, the notification 118 instructs the user to tighten the wearable device 104 to the wrist 103.

Figure 1C:
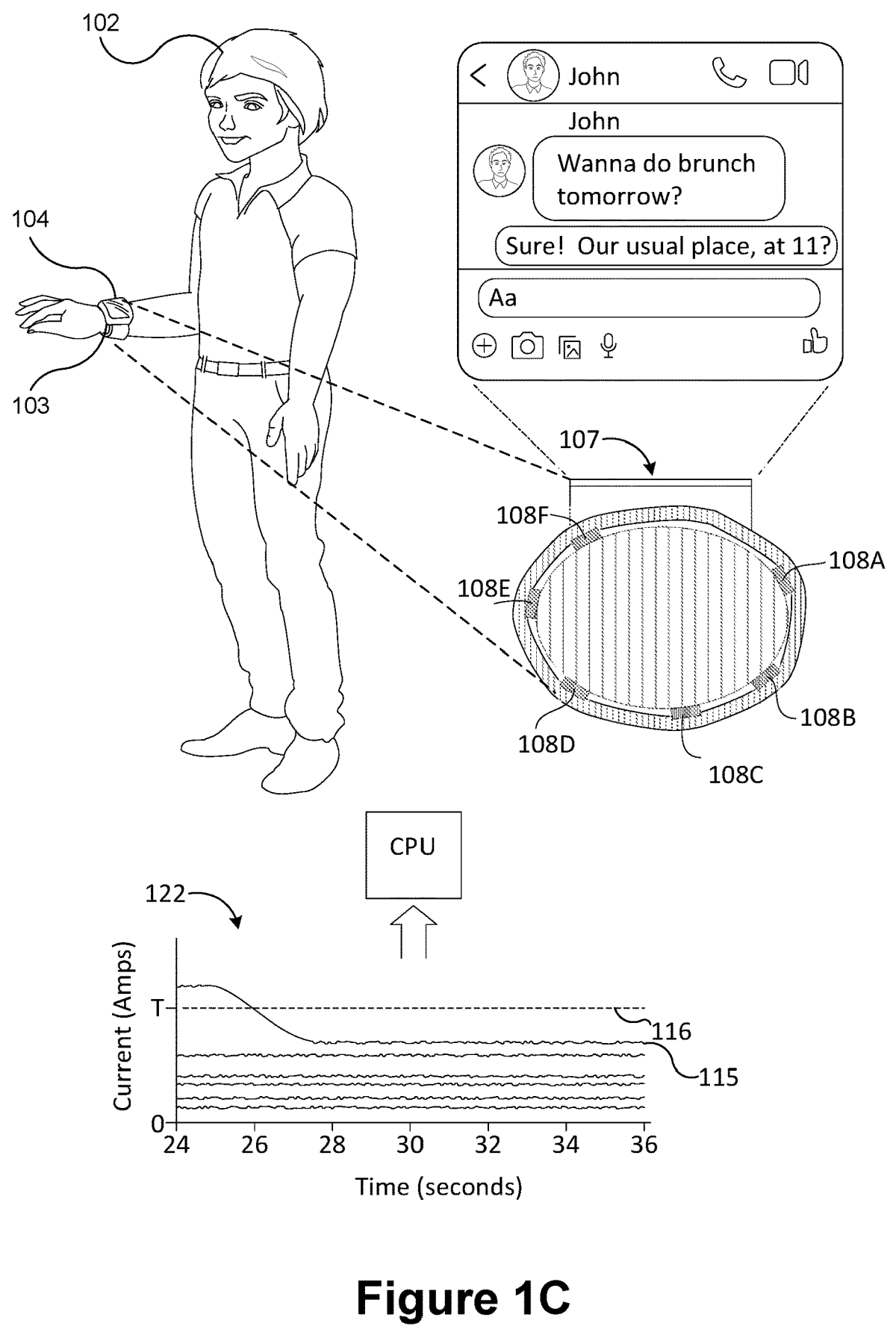

FIG. 1C shows an example interaction where the wearable device is properly affixed to a wrist of a user, in accordance with some embodiments. FIG. 1C builds off FIGS. 1A-1B, and shows that as a result of the user 102 tightening the wearable device 104 around their wrist 103, the notification 118 is ceased to be displayed. The current over time chart 122, which is the same as the chart 110, but at a later point in time, also shows that the line 115 corresponding to biopotential-signal sensor 108C has fallen below the threshold line 116, in response to biopotential-signal sensor 108C, as shown in cross-sectional view 107, being in better contact with the wrist 103 of the user 102.

Figure 2A:
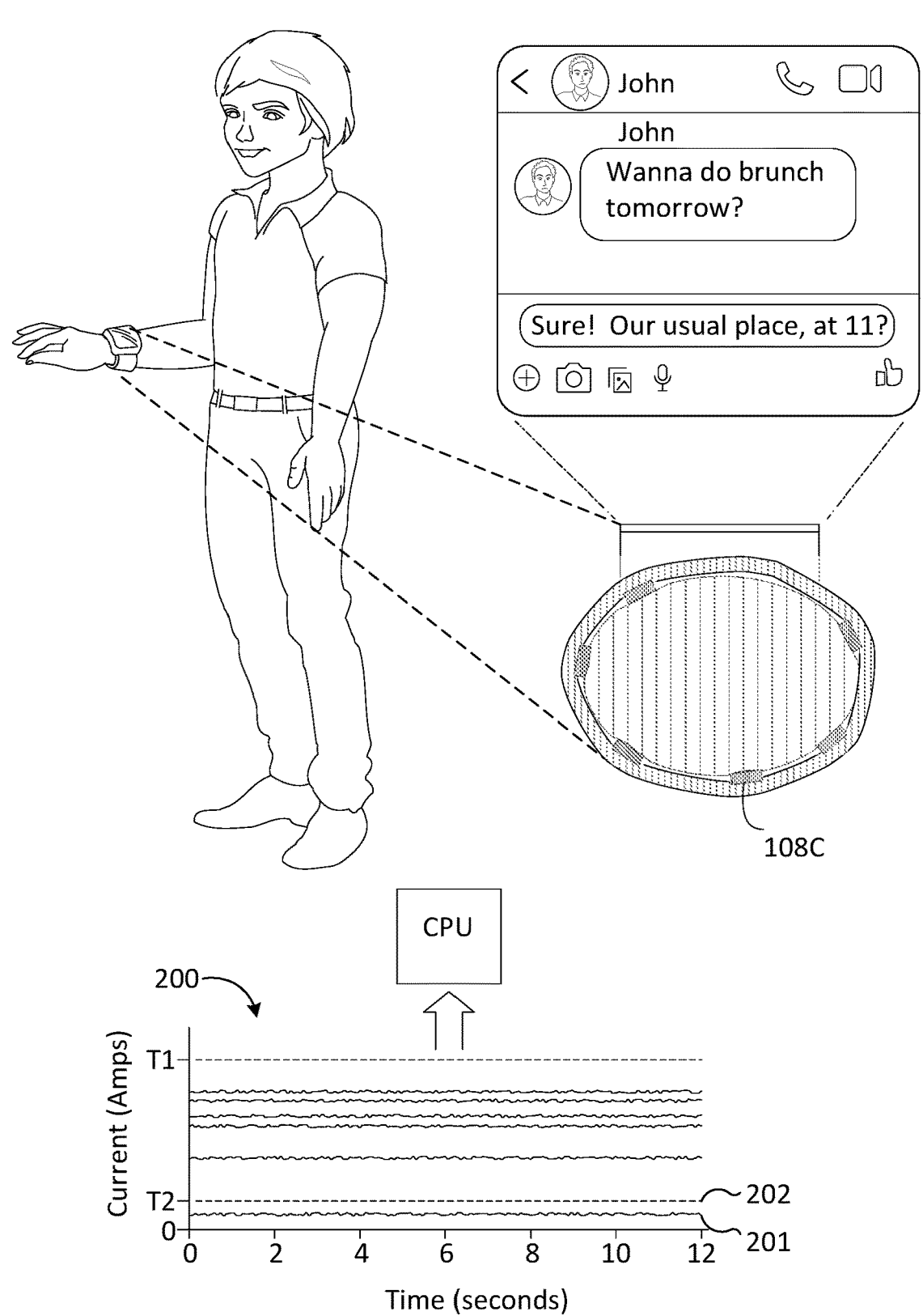
FIG. 2A shows an example interaction where the wearable device is potentially overtightened on a user's wrist, in accordance with some embodiments.

FIG. 2A shows an example interaction where the wearable device is potentially overtightened on a user's wrist, in accordance with some embodiments. While this is not necessarily a performance issue, it could potentially be a comfort issue that leads to the user loosening the wearable device to a point that it becomes a performance issue.

FIG. 2A shows in current over time chart 200 that the current applied to biopotential-signal sensor 108C to amplify the signal (as indicated by line 201) as being below a minimum threshold line 202. As discussed above, since current for amplification can be used as a proxy to determine tightness, it can be determined, by the processor, that if the required amplification is low enough, the biopotential-signal sensor could be placed too tightly around the wrist of the user and could cause discomfort. In some embodiments, the type of detected exercise may warrant different tightness and looseness thresholds. For example, when sitting at a desk, a looser band may be sufficient, but a tighter band may be required for exercising.

Figure 2B:
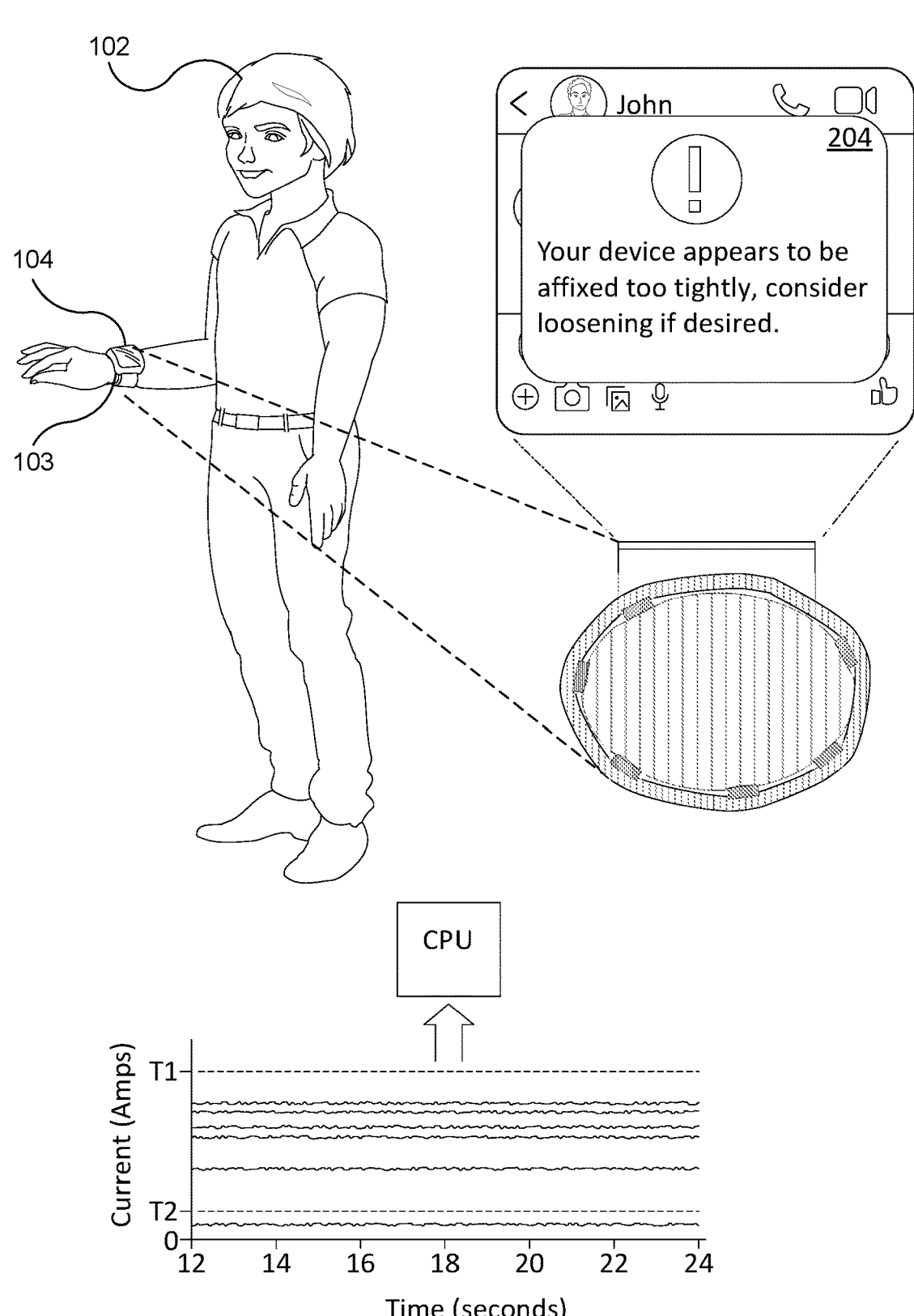
FIG. 2B shows an example interaction where the wearable device is potentially overtightened on a user's wrist and a resulting notification is provided, in accordance with some embodiments.

FIG. 2B shows an example interaction where the wearable device is potentially overtightened on a user's wrist and a resulting notification is provided, in accordance with some embodiments. FIG. 2B illustrates a notification 204 for providing an instructions to adjust how the wearable device 104 is affixed to the wrist 103 of a user 102. In this instance, the notification 204 instructs the user to loosen the wearable device 104 on the wrist 103 if desired by the user (e.g., suggesting that this step may be optional). In some embodiments, the user can adjust whether these notifications are received or not. For example, the user may desire to wear the wearable device tighter than the threshold.

Figure 2C:
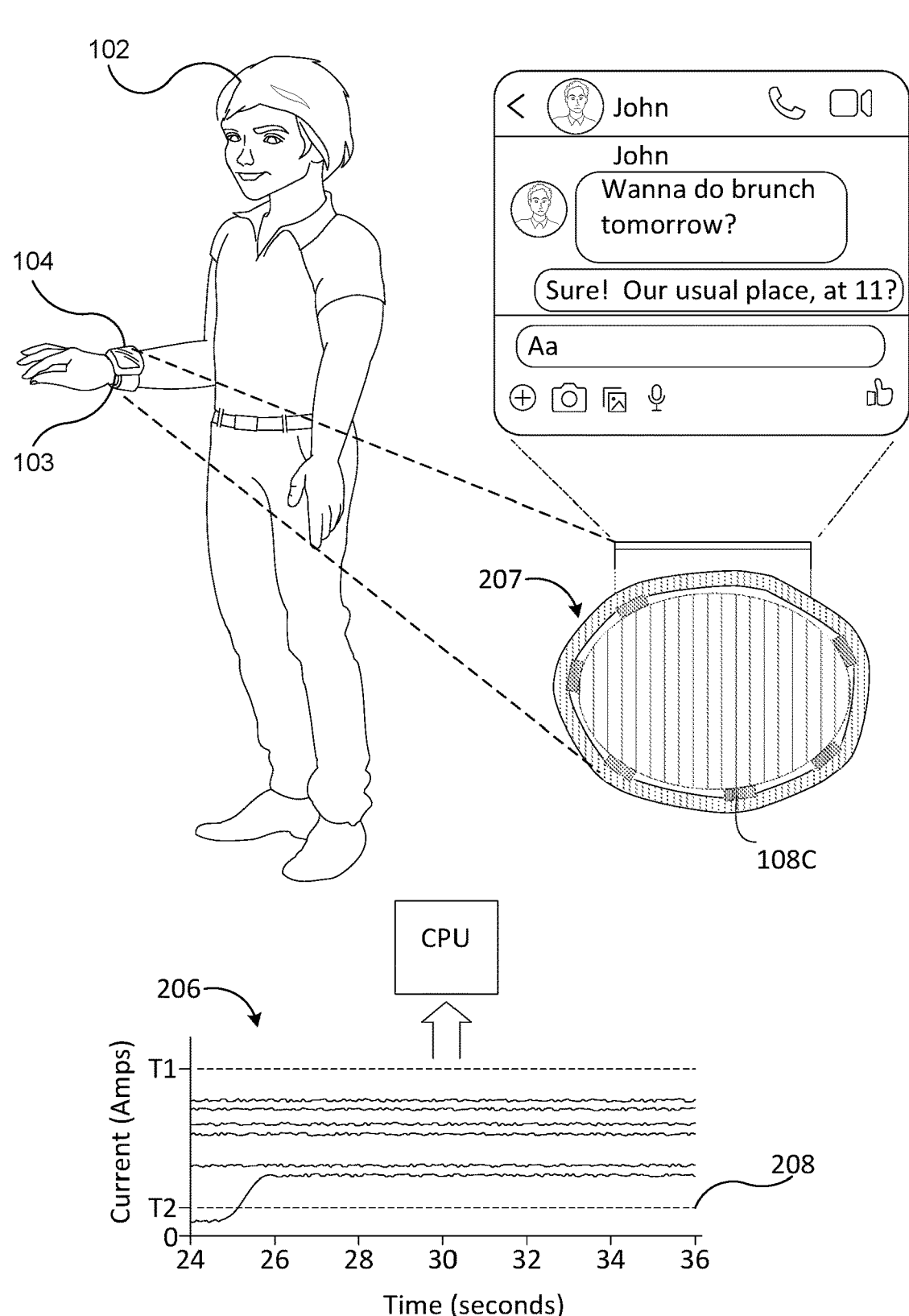
FIG. 2C shows an example interaction where the wearable device is properly affixed to a wrist of a user, in accordance with some embodiments.

FIG. 2C shows an example interaction where the wearable device is properly affixed to a wrist of a user, in accordance with some embodiments. FIG. 2C builds off of FIG. 2A-2B, and shows that as a result of the user 102 loosening the wearable device 104 around their wrist 103, the notification 204 is ceased to be displayed. The current over time chart 206, which is the same as the chart 200, but at a later point in time, also shows that the line 201 corresponding to biopotential-signal sensor 108C has surpassed or met the threshold line 208, in response to biopotential-signal sensor 108C, as shown in cross-sectional view 207, being looser around the wrist 103 of the user 102.

Figure 3A:
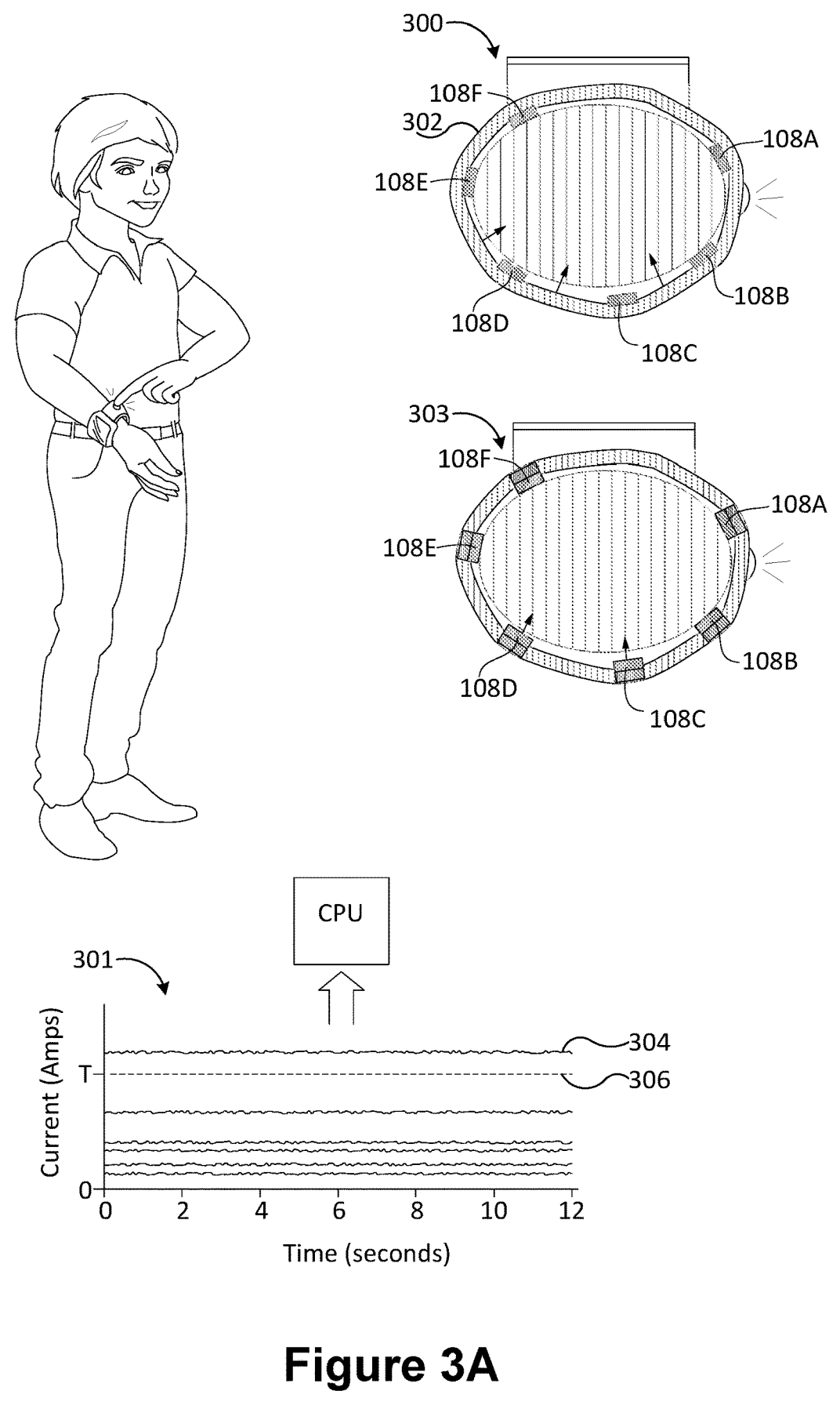
Figure 3B:
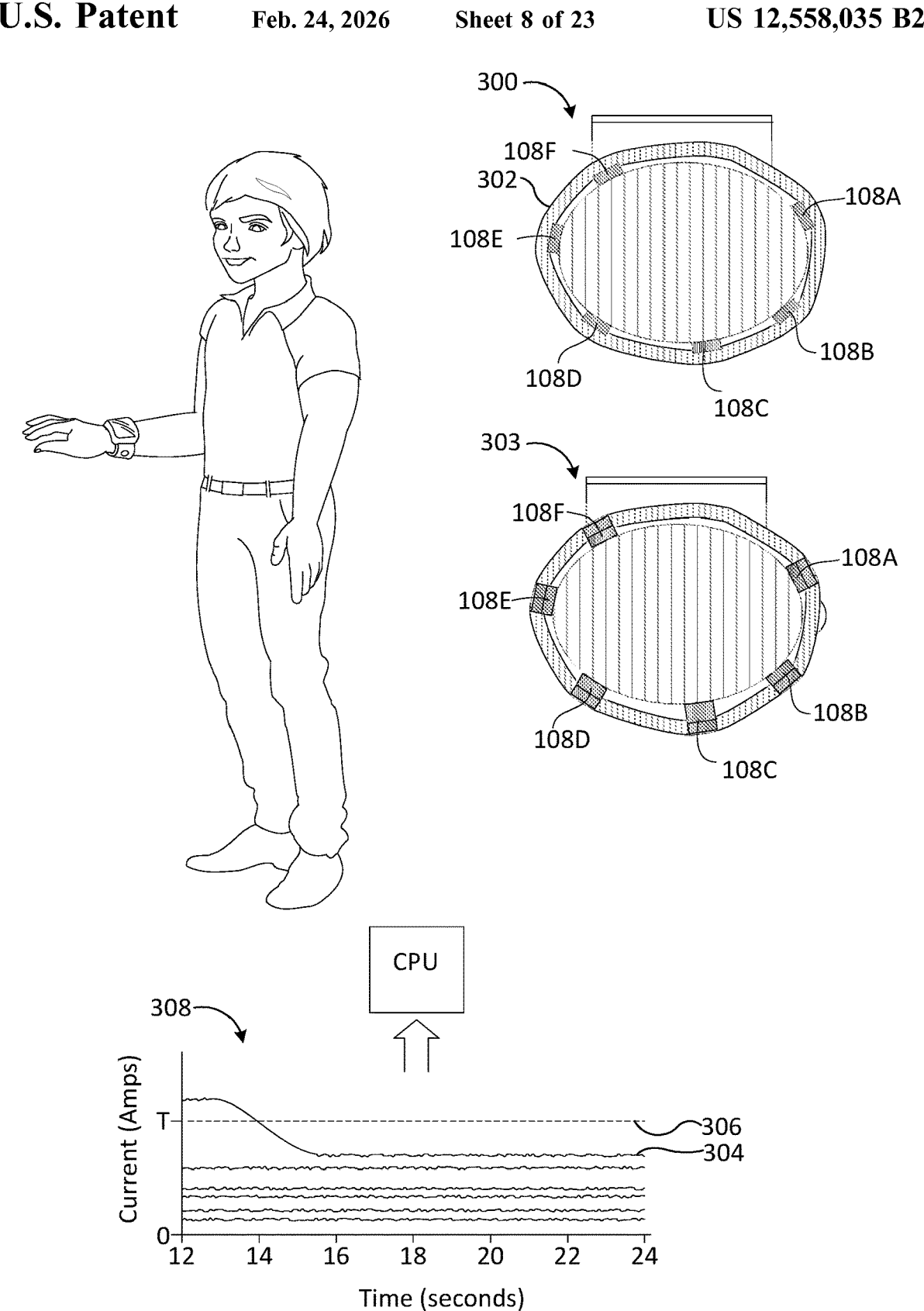

FIGS. 3A and 3B illustrate a way of automatically adjusting the fit of the wearable device, in accordance with some embodiments. FIG. 3A shows a first example wearable device 300 that includes a first type of automatic fit adjustment mechanism. The first type of automatic fit adjustment mechanism is a mechanism for tightening and/or loosening of band 302 of the wearable device 300, which thereby tightens and/or loosens the biopotential-signal sensors 108A-108F to the wrist of the user. FIG. 3A also shows a second example wearable device 303 that includes a second type of automatic fit adjustment mechanism.

The second type of automatic fit adjustment mechanism is a mechanism for tightening and/or loosening of the individual biopotential-signal sensors 108A-108F to the wrist of the user. This second type of automatic fit adjustment can be used in place of or in addition to the first type of automatic fit adjustment. A current over time chart 301 also shows that the current over time, as indicated by line 304, applied to biopotential-signal sensor 108C to amplify the signal is above a maximum threshold line 306. As discussed above, the amount of power needed to amplify the signal can be used as a proxy for determining whether the biopotential-signal sensor is fitted properly.

FIG. 3B shows that in response to the wearable device determining, via a processor, that the biopotential-signal sensor 108C is not properly fastened to the wrist 103 of the user 102, the wearable device automatically adjusts (e.g., without human intervention) to ensure an appropriate fit. FIG. 3B shows a first example wearable device 300 that includes a first type of automatic fit adjustment mechanism that is configured to tighten the band 302, which consequently tightens the biopotential-signal sensors 108A-108F to the wrist of the user. FIG. 3B also shows a second example wearable device 303, that includes a second type of automatic fit adjustment mechanism, tightens individual biopotential-signal sensor 108C in response to determining, via the processor, that the biopotential-signal sensor 108C is not properly fastened. A current over time chart 308, which is the same chart as current over time chart 301, but at a later time interval, also shows that the line 304 representing the amplification current is less than the maximum threshold line 306.

FIG. 4 shows a flow chart of a method of securing a wearable device to a user, in accordance with some embodiments. The wearable device includes a biopotential-signal sensor configured to receive a biopotential signal and the biopotential-signal sensor is connected to an amplifier (e.g., an analog front end (AFE)) to adjust amplification of the biopotential signal to a particular amplitude for signal processing (e.g., FIG. 1A illustrates a user 102 wearing a wearable device 104 on their wrist 103).

(A1) In accordance with some embodiments, the method occurs while the wearable device is worn around a body part (e.g., a wrist, an ankle, a head, a waist, a leg, etc.,). The method includes, receiving first information representative of power needed to amplify the biopotential signal to the particular amplitude for signal processing (e.g., FIG. 1A shows that the current over time chart 110 shows a line 115 that indicates that the biopotential-signal sensor 108C is consuming more current (e.g., has a higher power draw) than the other biopotential-signal sensors).

While the wearable device is worn around a body part, in accordance with a determination that the first information representative of the power needed to amplify the biopotential signal to the particular amplitude for signal processing indicates that the wearable device is not properly affixed to a body part of a user, providing first instructions to adjust how the wearable device is affixed to the wrist of a user (e.g., FIG. 1B shows a notification 118 for providing an instructions to adjust how the wearable device 104 is affixed to the wrist 103 of a user 102.).

While the wearable device is worn around a body part, receiving second information representative of power needed to amplify the biopotential signal to the particular amplitude for signal processing.

While the wearable device is worn around a body part, in accordance with a determination that the second information representative of the power needed to amplify the biopotential signals to the particular amplitude for signal processing indicates that the wearable device is properly affixed to the wrist of the user, forgoing providing second instructions to adjust how the wearable device is affixed to the body part of the user (e.g., FIG. 1C shows that as a result of the user 102 tightening the wearable device 104 around their wrist 103, the notification 118 is ceased to be displayed).

(A2) In some embodiments of A1, providing first instructions to adjust how the wearable device is affixed to the body part of the user includes providing instructions as to tightening or loosening the wearable device around the body part (e.g., FIG. 1B shows in the notification 118 instructs the user to tighten the wearable device 104 to the wrist 103, and FIG. 2B shows a notification 204 that instructs the user to loosen the wearable device 104 on the wrist 103 if desired by the user).

(A3) In some embodiments of A1-A2, providing the first instructions to adjust how the wearable device is affixed to the wrist of a user includes causing display of a visual alert (e.g., FIGS. 1B and 2B show their respective notifications being displayed on a display of the wearable device).

(A4) In some embodiments of A1-A3, the visual alert is displayed via a display device (e.g., the visual alert is a color of an LED, the alert is a descriptive notification displayed on a display of the wearable device) of the wearable device (e.g., FIGS. 1B and 2B show their respective notifications being displayed on a display of the wearable device).

(A5) In some embodiments of A1-A4, the wearable device is in communication with another electronic device that includes a display, and the providing of the first instructions occurs at the display of the other electronic device.

(A6) In some embodiments of A1-A5, the wearable device includes post-amplifier signal processing components. In some embodiments, while the wearable device is worn around the body part of the user: in accordance with the determination that the first information representative of the power needed to amplify the biopotential signal to the particular amplitude for signal processing indicates that the wearable device is not properly affixed to the wrist of the user, forgoing processing biopotential signal data by the post-amplifier signal processing components. For example, FIG. 1A describes a CPU 111 that can also function as a post-amplifier signal processing component.

(A7) In some embodiments of A1-A6, the wearable device includes post-amplifier signal processing components, and the method includes, while the wearable device is worn around the wrist of the user, in accordance with the determination that the second information representative of the power needed to amplify the biopotential signal to the particular amplifier for signal processing indicates that the wearable device is affixed to the wrist of the user, processing biopotential signal data by the post-amplifier signal processing components. For example, FIG. 1A describes a CPU 111 that can also function as a post-amplifier signal processing component.

(A8) In some embodiments of A1-A7, the wearable device includes an automatic-wrist-fit adjusting mechanism, the method includes, before receiving the second information, receiving, at the automatic-wrist-fit adjusting mechanism, the first instructions to adjust how the wearable device is affixed to the wrist of a user, and in response to receiving the first instructions, automatically adjusting a fit characteristic of the wearable device (e.g., FIGS. 3A and 3B illustrate a way of automatically adjusting the fit of the wearable device).

(A9) In some embodiments of A1-A8, the determination that the second information representative of the power needed to amplify the biopotential signals to the particular amplitude for signal processing indicates that the wearable device is properly affixed to the wrist of the user is made after adjusting the fit characteristic of the wearable device (e.g., FIG. 1C shows that a second determination is made after the fit of the wearable device is adjusted, which is evidenced by the notification 118 being removed).

(A10) In some embodiments of A1-A9, the automatically adjusting a fit characteristic of wearable device occurs via a linear actuator (and) or by adjusting the individual fit of the biopotential-signal sensor (e.g., without tightening the band). In some embodiments, the wearable device is properly affixed to skin of a user when the biopotential signal sensor has a minimum skin depression depth between 1 mm to 5 mm.

(A11) In some embodiments of A1-A10, the method includes, automatically adjusting the fit characteristic until a further determination is made that the wearable device is properly affixed to the body part of the user, and when the further determination is made, ceasing to further adjust how the wearable device is affixed to the body part of the user (e.g., FIG. 3B shows the adjustment ceasing after the biopotential signal sensors are properly affixed to the user's wrist).

(A12) In some embodiments of A1-A11, the first information representative of the power needed to amplify the biopotential signal to the particular amplifier for signal processing includes a measurement of the average current being used to amplify signals detected by the biopotential-signal sensor.

(A13) In some embodiments of A1-A12, the measurement of average current being sent to the biopotential-signal sensor exceeds 50 microamps.

(A14) In some embodiments of A1-A13, the second information representative of the power needed to amplify the biopotential signal to the particular amplifier for signal processing includes a measurement of the average current being used to amplify signals detected by the biopotential-signal sensor.

(A15) In some embodiments of A1-A14, the measurement of average current being sent to the biopotential-signal sensor does not meet 30 milliamps.

(A16) In some embodiments of A1-A15, the wearable device is a wrist-wearable device and the body part of the user is a wrist (e.g., FIGS. 1A-3B show a wearable device being worn on a wrist of user).

(A17) In some embodiments of A1-A16 the biopotential-signal sensor is a neuromuscular signal sensor configured to receive a neuromuscular signal.

(B1) In accordance with some embodiments, a non-transitory computer readable storage medium including instructions that, when executed by a computing device in communication with a wearable device, cause the computer device to perform any of A1-A17.

(C1) In accordance with some embodiments, a computing device in communication with a wearable device, comprises memory and one or more programs. The one or more programs are stored in the memory and configured to be executed by the one or more processors of the computing device, the one or more programs including instructions for performing any of A1-A17.

In accordance with some embodiments, a wearable device comprises memory and one or more programs. The one or more programs are stored in the memory and configured to be executed by the one or more processors of the wearable device, the one or more programs including instructions for performing any of A1-A17.

Further embodiments and variations related to wearable devices that include biopotential sensors and optical sensors are described in additional detail below.

Figure 8B:
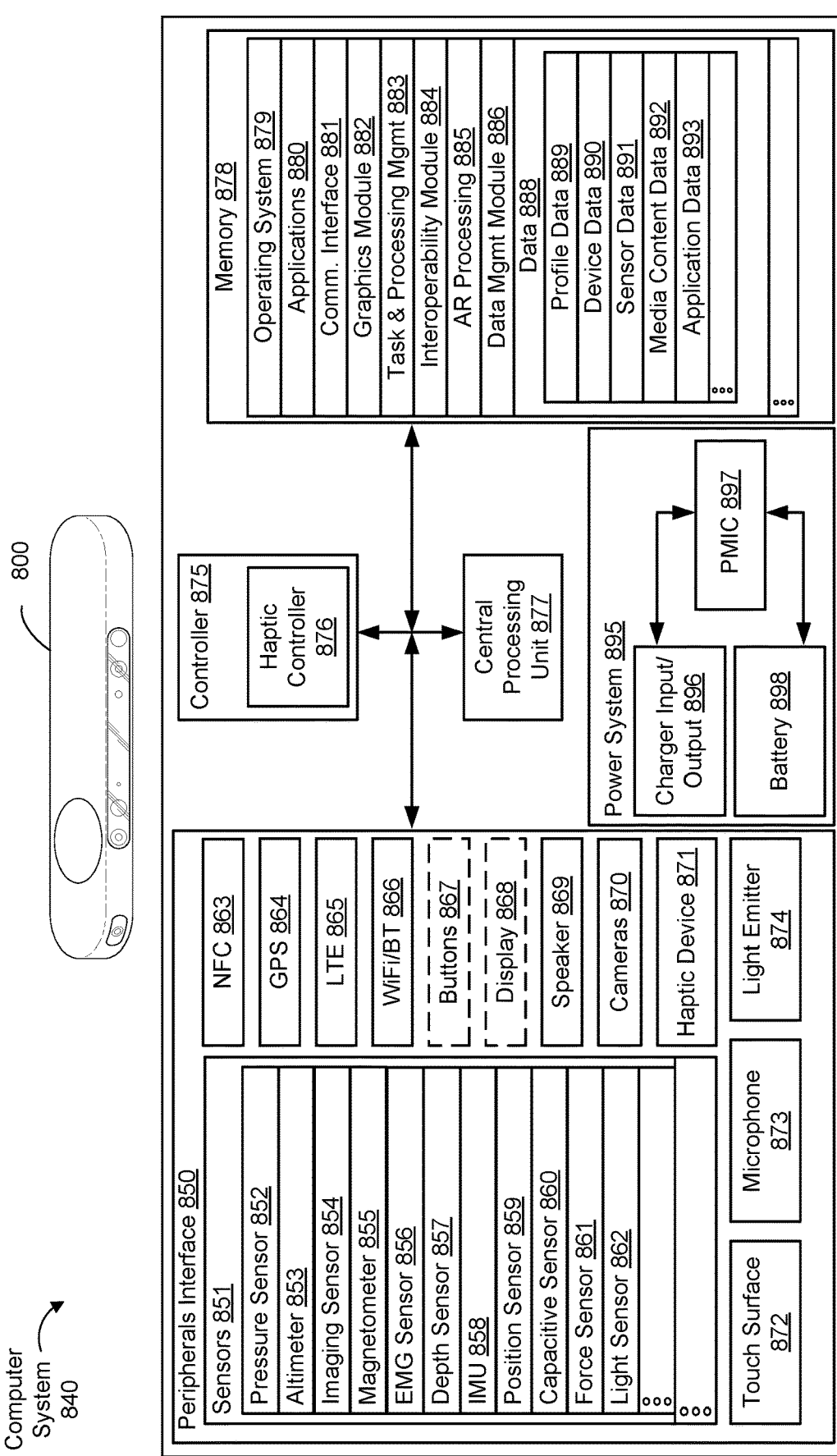

(D1) In accordance with some embodiments, a wearable device (e.g., wearable device 104 in FIGS. 8A-8C) includes a biopotential-signal sensor (e.g., sensor component 802 in FIGS. 8A-8C), and an optical sensor configured to detect optical data indicating changes in position of the biopotential-signal sensor (e.g., relative to a body part of the user (e.g., detecting moving about a wrist of a user)). For example, FIG. 8A shows in chart 808 recorded movement determined from data provided by the optical sensor component 804. The wearable device also includes a processor (e.g., or more than one processor) configured to receive (i) biopotential-signal data from the biopotential-signal sensor and (ii) the optical data from the optical sensor. The processor is also configured to determine one or more motion artifacts in the biopotential-signal data based on the optical data. The processor is further configured to adjust the biopotential signal data based on the motion artifacts to produce corrected biopotential signal data. For example, FIG. 8A shows in chart 810 artifacts that were the result of motion with respect to the user's wrist have been removed.

Removing artifacts improves the accuracy of data, which ensures that resulting operations match the users inputs. Having disconnects between inputs and resulting operations can make using the wearable device difficult and frustrating, especially when inputs need to be repeated. Having operations that match the inputs provided by the user allow for quick interactions that allow the user to seamlessly interact with the device, which reduces the number of inputs and thereby reduces battery consumption.

In some embodiments, the processor is also located on a remote device where at least some of the operations can be performed at instead (i.e., to reduce power consumption on devices with small batteries).

(D2) In some embodiments of D1, the biopotential-signal sensor is an electromyography (EMG) sensor or an electrocardiogram (ECG) sensor.

(D3) In some embodiments of any of D1-D2, the optical sensor is located at the center of the biopotential signal sensor (e.g., signal recording electrode would surround the aperture of the optical sensors for biopotential recording). FIG. 9A shows that the optical sensor component 804 is in the center of the sensor 802.

(D4) In some embodiments of any of D1-D3, the motion artifacts are determined based on lateral slip detection (electrode movement on x-axis and y-axes) and lift-off detection (electrode movement on the z-axis). FIGS. 8A-8B show in chart 808 and 836, respectively, that movement can be detected along three different axes.

(D5) In some embodiments of any of D1-D4, the biopotential-signal sensor is made from an inherently electrically conductive material.

(D6) In some embodiments of any of D1-D5, the biopotential-signal sensor is made from a transparent material (e.g., glass or a polymer) that is coated with a transparent conductive material (e.g., indium tin oxide, carbon nanotubes or other transparent conductors) thereby allowing the optical sensor to view images through the transparent material.

(D7) In some embodiments of any of D1-D6, the optical sensor is one or more of a: light emitting diode, lasers, photodiode, photomultiplier, optical fiber, filter, waveguide, lens, imaging sensor, or photonic integrated circuits.

(D8) In some embodiments of any of D1-D7, the optical sensor relies on one or more of the following measurements techniques: optical flow sensing, speckle sensing, or optical sensor-skin distance measurement.

(D9) In some embodiments of any of D1-D8, the optical sensor is integrated into the biopotential-signal sensor such that the biopotential-signal sensor encloses the optical sensor (e.g., in a spherical biopotential-signal sensor, the optical center is concentric with the biopotential-signal sensor). For example, FIG. 9A shows that the optical sensor component 804 is integrated into the sensor 802 and is also surrounded by the sensor 802.

(D10) In some embodiments of any of D1-D9, the optical sensor is stacked on top of the biopotential signal sensor. FIGS. 8A-8C show an embodiment where the optical sensor component 804 is above the sensor component 802.

(D11) In some embodiments of any of D1-D10, the processor is configured to determine whether the bio-potential signal sensor has enough pressure on a user's skin via optical data from the optical sensor (e.g., the camera can determine how much ambient light is incoming and using that light to determine if the sensor is in close enough contact). FIG. 8C illustrates an embodiment where the optical sensor component 804 is being used to determine pressure based on how much light is being detected (e.g., light entering because the sensor 802 is not pushed down enough on the wrist 103 of the user 102, or by how much light is escaping (e.g., how well it is illuminating the user's wrist) if the light source 805-1 is turned on).

(D12) In some embodiments of any of D1-D11, the adjusting the biopotential-signal data based on the motion artifacts to produce corrected biopotential signal data, includes adjusting based on the frequency content of the artifacts.

(D13) In some embodiments of D1-D12, the processor is configured to determine a fit characteristic of the biopotential-signal sensor based on the optical data. The processor is further configured to provide information for adjusting fit of the biopotential-signal sensor based on the determined fit characteristic.

(D14) In some embodiments of D1-D13, the processor is configured to provide the corrected biopotential signal data to an application. The processor is also configured to, in response to providing the corrected biopotential signal data to the application, perform an operation in an application based on the corrected biopotential signal data. For example, both FIGS. 8A and 8B show a message being sent within the user interface 822 in response to the non-erroneous spike 820 corresponding to an input made by the user 102.

(E1) In accordance with some embodiments, a sensor system includes a biopotential-signal sensor, and an optical sensor configured to detect optical data indicating changes in position of the biopotential-signal sensor (e.g., relative to a body part of the user (e.g., detecting moving about a wrist of a user). The sensor system also includes a processor (e.g., or more than one processor) configured to receive (i) biopotential-signal data from the biopotential-signal sensor and (ii) the optical data from the optical sensor, and determine one or more motion artifacts in the biopotential-signal data based on the optical data. The processor is also configured to adjust the biopotential signal data based on the motion artifacts to produce corrected biopotential signal data.

In some embodiments, a fusing of sensor data from multiple types of sensors (optical, imaging, and EMG sensors) can be used to collectively detect gestures (each of the types of sensor data can be provided as inputs to one or more trained machine-learning models for gesture-detection purposes).

While the primary example provided herein relates to using data from the optical sensors to adjust biopotential-signal data, other types of sensor data can also be corrected based on data from an optical sensor. Thus, other examples of sensor data that can be corrected include skin temperature, pulse oximeter, tissue oxygenation, blood pressure, etc.).

(E2) In some embodiments of E1, the sensor system is configured in accordance with any of D21-D34.

(F1) In accordance with some embodiments, a method of removing motion artifacts from biopotential signals occurs at wearable device that includes a biopotential-signal sensor and an optical sensor that is configured to detect optical data indicating changes in position of the biopotential-signal sensor. The method includes, receiving (i) biopotential-signal data from the biopotential-signal sensor and (ii) the optical data from the optical sensor. The method also includes, determining one or more motion artifacts in the biopotential-signal data based on the optical data. The method further comprises, adjusting the biopotential signal data based on the motion artifacts to produce corrected biopotential signal data.

(F2) In some embodiments of F1, the wearable device is configured in accordance with any of D21-D34.

The devices described above are further detailed below, including systems, wrist-wearable devices, headset devices, and smart textile-based garments. Specific operations described above may occur as a result of specific hardware, such hardware is described in further detail below. The devices described below are not limiting and features on these devices can be removed or additional features can be added to these devices. The different devices can include one or more analogous hardware components. For brevity, analogous devices and components are described below. Any differences in the devices and components are described below in their respective sections.

As described herein, a processor (e.g., a central processing unit (CPU), microcontroller unit (MCU), etc.), is an electronic component that is responsible for executing instructions and controlling the operation of an electronic device (e.g., a wrist-wearable device 600, a head-wearable device, an HIPD 800, a smart textile-based garment 900, or other computer system). There are various types of processors that may be used interchangeably, or may be specifically required, by embodiments described herein. For example, a processor may be: (i) a general processor designed to perform a wide range of tasks, such as running software applications, managing operating systems, and performing arithmetic and logical operations; (ii) a microcontroller designed for specific tasks such as controlling electronic devices, sensors, and motors; (iii) a graphics processing unit (GPU) designed to accelerate the creation and rendering of images, videos, and animations (e.g., virtual-reality animations, such as three-dimensional modeling); (iv) a field-programmable gate array (FPGA) that can be programmed and reconfigured after manufacturing, and/or can be customized to perform specific tasks, such as signal processing, cryptography, and machine learning; (v) a digital signal processor (DSP) designed to perform mathematical operations on signals such as audio, video, and radio waves. One of skill in the art will understand that one or more processors of one or more electronic devices may be used in various embodiments described herein.

As described herein, controllers are electronic components that manage and coordinate the operation of other components within an electronic device (e.g., controlling inputs, processing data, and/or generating outputs). Examples of controllers can include: (i) microcontrollers, including small, low-power controllers that are commonly used in embedded systems and Internet of Things (IoT) devices; (ii) programmable logic controllers (PLCs) which may be configured to be used in industrial automation systems to control and monitor manufacturing processes; (iii) system-on-a-chip (SoC) controllers that integrate multiple components such as processors, memory, I/O interfaces, and other peripherals into a single chip; and/or DSPs. As described herein, a graphics module is a component or software module that is designed to handle graphical operations and/or processes, and can include a hardware module and/or a software module.

As described herein, memory refers to electronic components in a computer or electronic device that store data and instructions for the processor to access and manipulate. The devices described herein can include volatile and non-volatile memory. Examples of memory can include: (i) random access memory (RAM), such as DRAM, SRAM, DDR RAM or other random access solid state memory devices, configured to store data and instructions temporarily; (ii) read-only memory (ROM) configured to store data and instructions permanently (e.g., one or more portions of system firmware, and/or boot loaders); (iii) flash memory, magnetic disk storage devices, optical disk storage devices, other non-volatile solid state storage devices, which can be configured to store data in electronic devices (e.g., USB drives, memory cards, and/or solid-state drives (SSDs); and (iv) cache memory configured to temporarily store frequently accessed data and instructions. Memory, as described herein, can include structured data (e.g., SQL databases, MongoDB databases, GraphQL data, JSON data, etc.). Other examples of memory can include: (i) profile data, including user account data, user settings, and/or other user data stored by the user; (ii) sensor data detected and/or otherwise obtained by one or more sensors; (iii) media content data including stored image data, audio data, documents, and the like; (iv) application data, which can include data collected and/or otherwise obtained and stored during use of an application; and/or any other types of data described herein.

As described herein, a power system of an electronic device is configured to convert incoming electrical power into a form that can be used to operate the device. A power system can include various components, including: (i) a power source, which can be an alternating current (AC) adapter or a direct current (DC) adapter power supply; (ii) a charger input, and can be configured to use a wired and/or wireless connection (which may be part of a peripheral interface, such as a USB, micro-USB interface, near-field magnetic coupling, magnetic inductive and magnetic resonance charging, and/or radio frequency (RF) charging); (iii) a power-management integrated circuit, configured to distribute power to various components of the device and to ensure that the device operates within safe limits (e.g., regulating voltage, controlling current flow, and/or managing heat dissipation); and/or (iv) a battery configured to store power to provide usable power to components of one or more electronic devices.

As described herein, peripheral interfaces are electronic components (e.g., of electronic devices) that allow electronic devices to communicate with other devices or peripherals, and can provide a means for input and output of data and signals. Examples of peripheral interfaces can include: (i) universal serial bus (USB) and/or micro-USB interfaces configured for connecting devices to an electronic device; (ii) bluetooth interfaces configured to allow devices to communicate with each other, including bluetooth low energy (BLE); (iii) near field communication (NFC) interfaces configured to be short-range wireless interface for operations such as access control; (iv) POGO pins, which may be small, spring-loaded pins configured to provide a charging interface; (v) wireless charging interfaces; (vi) GPS interfaces; (vii) WiFi interfaces for providing a connection between a device and a wireless network; (viii) sensor interfaces.

As described herein, sensors are electronic components (e.g., in and/or otherwise in electronic communication with electronic devices, such as wearable devices) configured to detect physical and environmental changes and generate electrical signals. Examples of sensors can include: (i) imaging sensors for collecting imaging data (e.g., including one or more cameras disposed on a respective electronic device); (ii) biopotential-signal sensors; (iii) inertial measurement unit (e.g., IMUs) for detecting, for example, angular rate, force, magnetic field, and/or changes in acceleration; (iv) heart rate sensors for measuring a user's heart rate; (v) SpO2 sensors for measuring blood oxygen saturation and/or other biometric data of a user; (vi) capacitive sensors for detecting changes in potential at a portion of a user's body (e.g., a sensor-skin interface) and/or the proximity of other devices or objects; (vii) light sensors (e.g., time-of-flight sensors, infrared light sensors, visible light sensors, etc.), and/or sensor for sensing data from the user or the user's environment. As described herein biopotential-signal-sensing components are devices used to measure electrical activity within the body (e.g., biopotential-signal sensors). Some types of biopotential-signal sensors include: (i) electroencephalography (EEG) sensors configured to measure electrical activity in the brain to diagnose neurological disorders; (ii) electrocardiography (ECG or EKG) sensors configured to measure electrical activity of the heart to diagnose heart problems; (iii) electromyography (EMG) sensors configured to measure the electrical activity of muscles and to diagnose neuromuscular disorders; (iv) electrooculography (EOG) sensors configure to measure the electrical activity of eye muscles to detect eye movement and diagnose eye disorders.

As described herein, an application stored in memory of an electronic device (e.g., software) includes instructions stored in the memory. Examples of such applications include: (i) games; (ii) word processors; (iii) messaging applications; (iv) media-streaming applications; (v) financial applications; (vi) calendars; (vii) clocks; (viii) web-browsers; (ix) social media applications, (x) camera applications, (xi) web-based applications; (xii) health applications; (xiii) artificial reality applications, and/or any other applications that can be stored in memory. The applications can operate in conjunction with data and/or one or more components of a device or communicatively coupled devices to perform one or more operations and/or functions.

As described herein, communication interface modules can include hardware and/or software capable of data communications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, or MiWi), custom or standard wired protocols (e.g., Ethernet or HomePlug), and/or any other suitable communication protocol, including communication protocols not yet developed as of the filing date of this document. A communication interface is a mechanism that enables different systems or devices to exchange information and data with each other, including hardware, software, or a combination of both hardware and software. For example, a communication interface can refer to a physical connector and/or port on a device that enables communication with other devices (e.g., USB, Ethernet, HDMI, Bluetooth). In some embodiments, a communication interface can refer to a software layer that enables different software programs to communicate with each other (e.g., application programming interfaces (APIs), protocols like HTTP and TCP/IP, etc.).

As described herein, a graphics module is a component or software module that is designed to handle graphical operations and/or processes, and can include a hardware module and/or a software module.

As described herein, non-transitory computer-readable storage media are physical devices or storage medium that can be used to store electronic data in a non-transitory form (e.g., such that the data is stored permanently until it is intentionally deleted or modified).

Example AR Systems

Figure 5A:
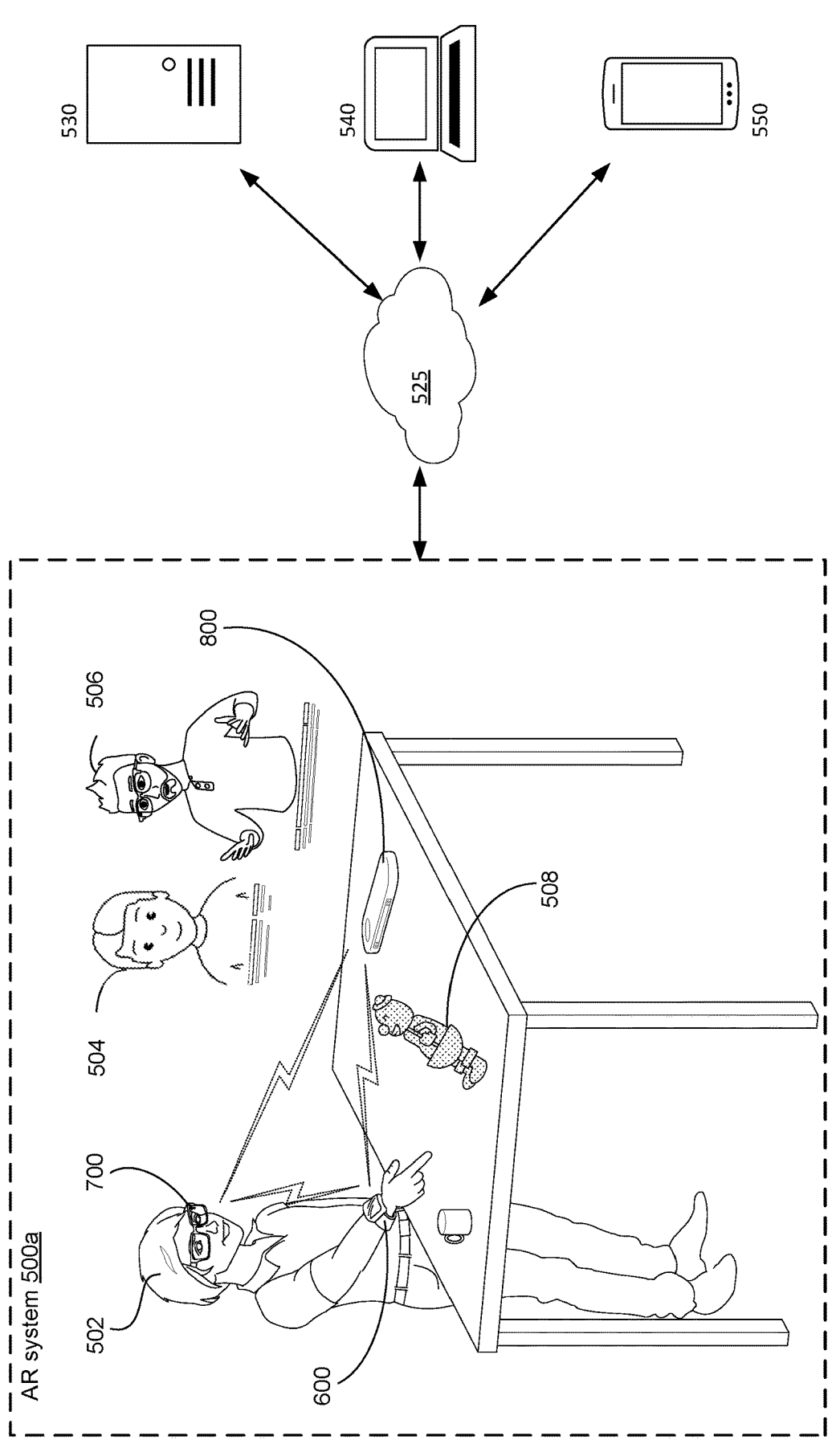
FIGS. 5A-5D-2 illustrate example artificial-reality systems, in accordance with some embodiments.
Figure 5B:
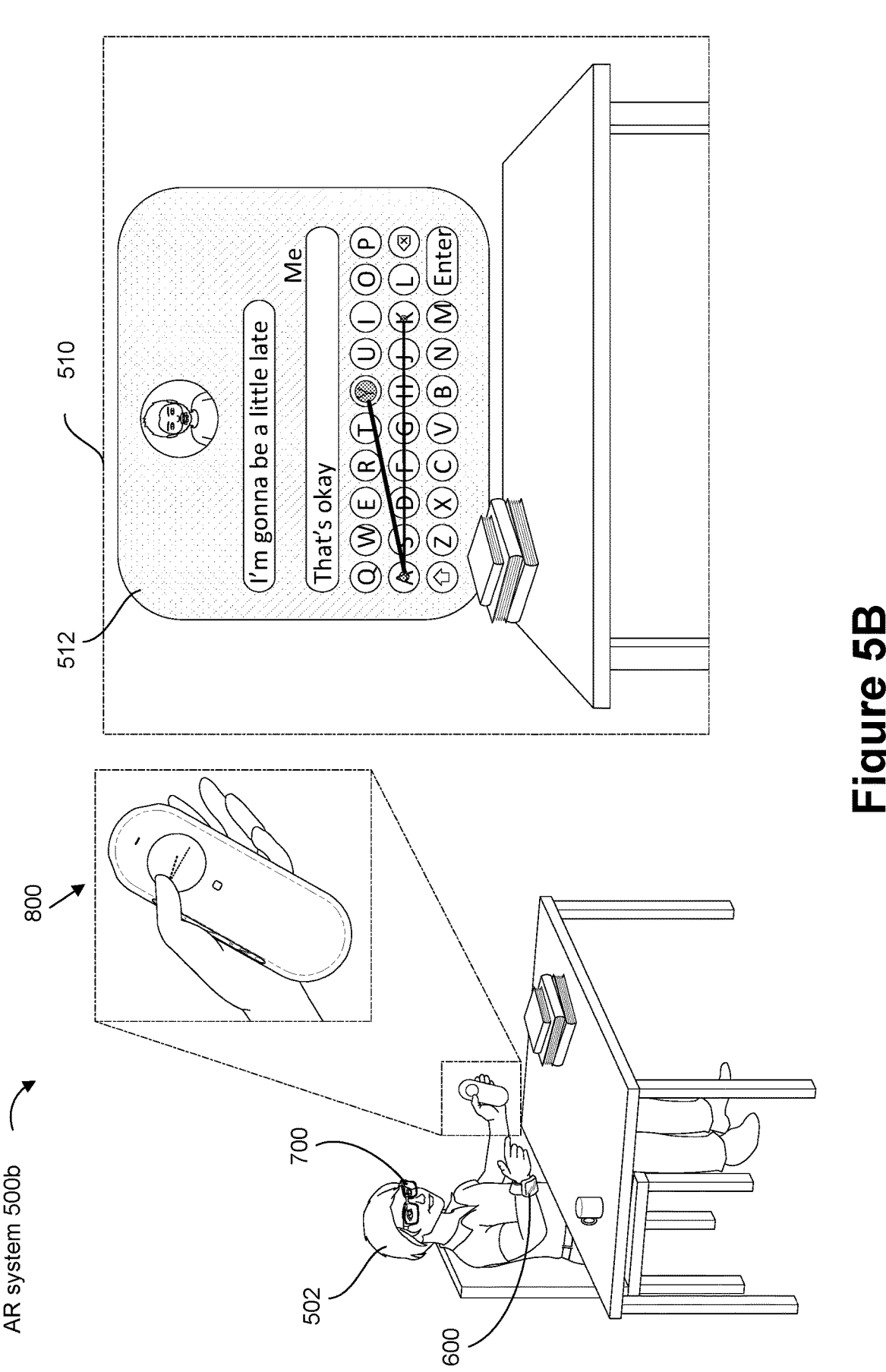
Figures 1, 5C:
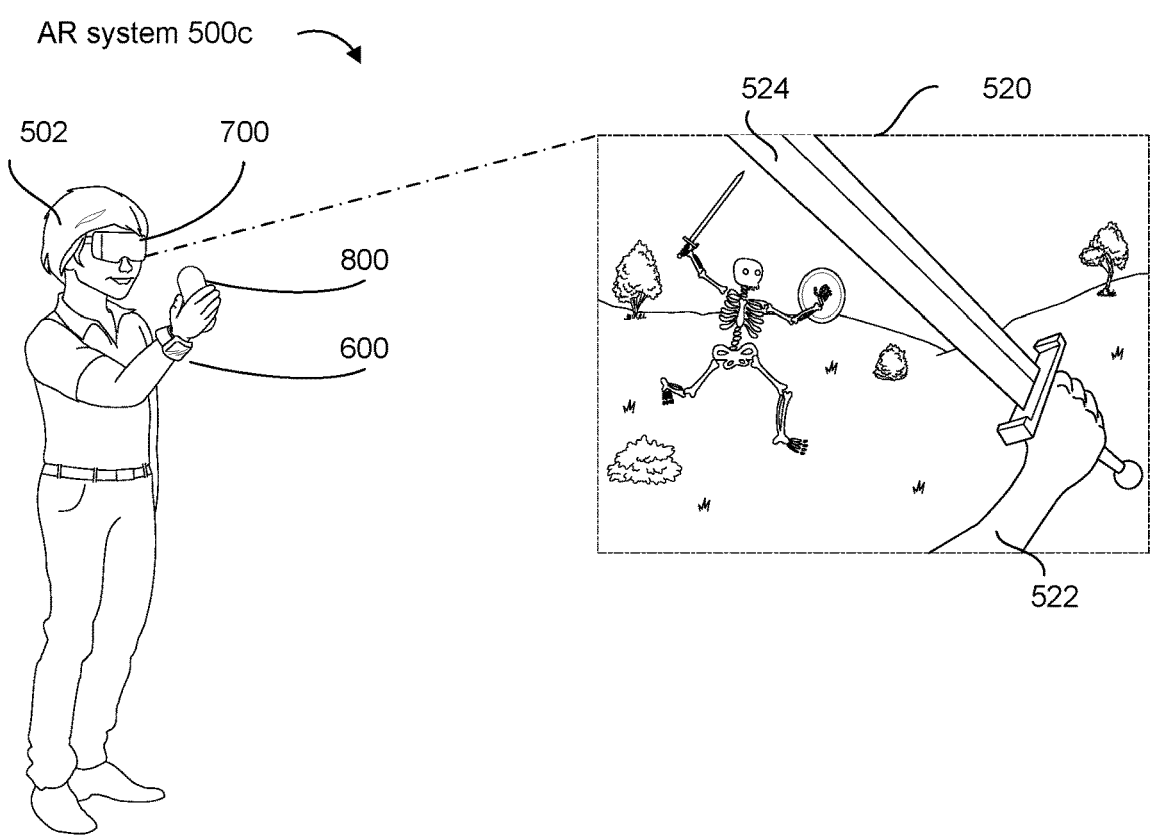
Figures 2, 5C:
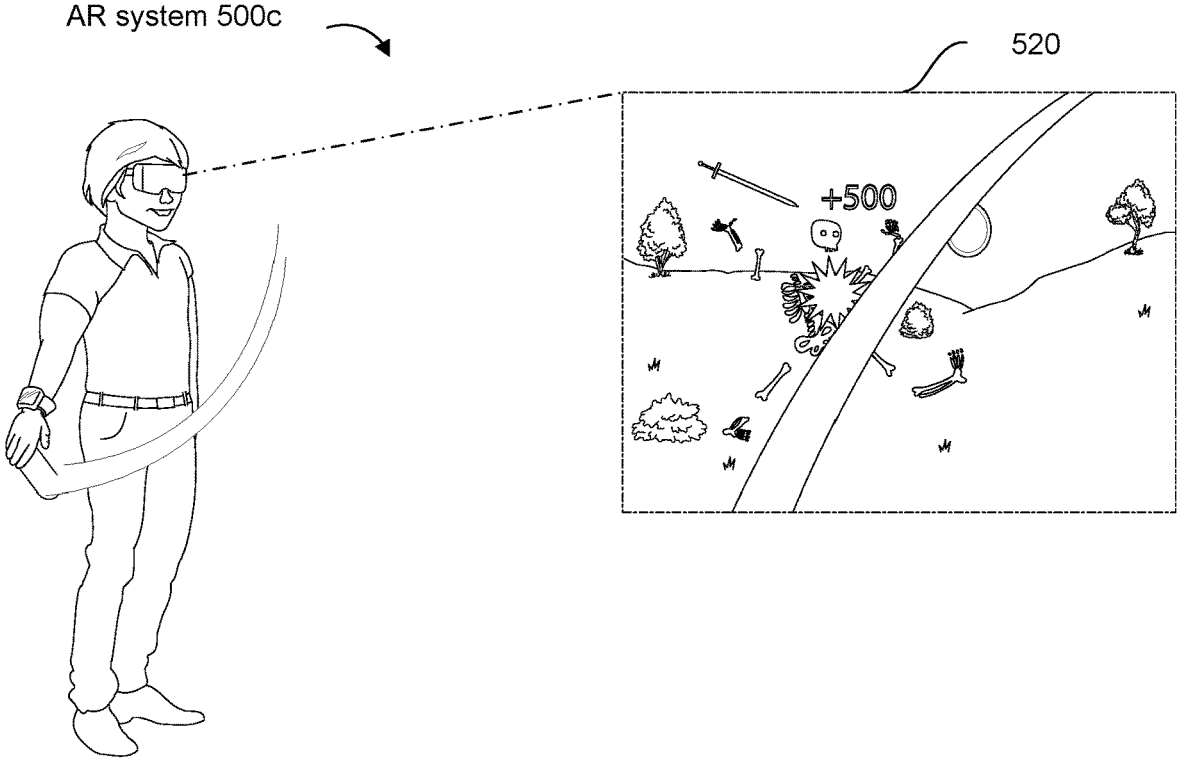
Figures 1, 5D:
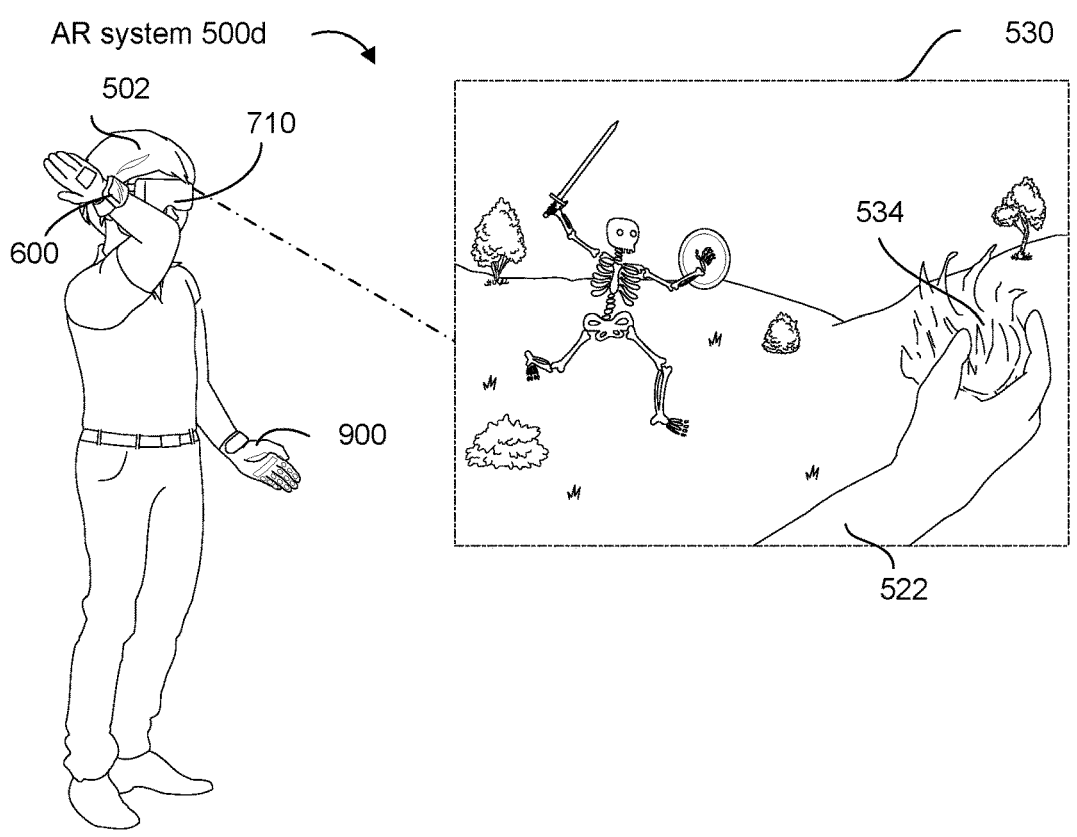
Figures 2, 5D:
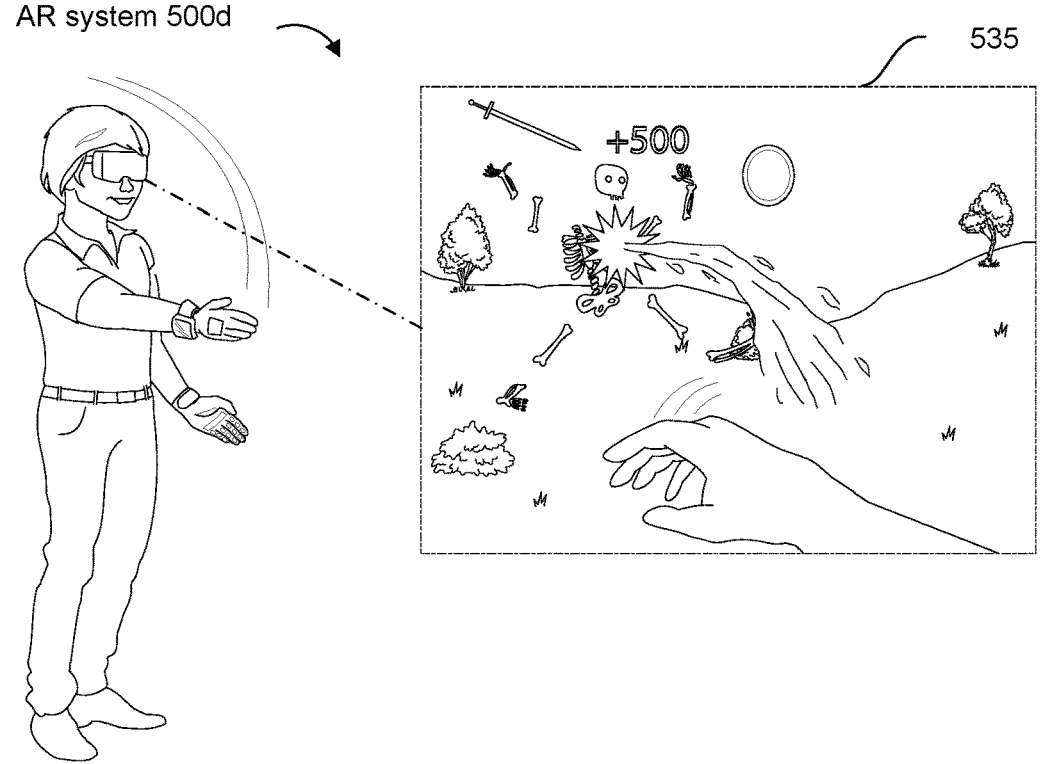

FIGS. 5A-5D-2 illustrate example artificial-reality systems, in accordance with some embodiments. FIG. 5A shows a first AR system 500a and first example user interactions using a wrist-wearable device 600, a head-wearable device (e.g., AR device 700), and/or a handheld intermediary processing device (HIPD) 800. FIG. 5B shows a second AR system 500b and second example user interactions using a wrist-wearable device 600, AR device 700, and/or an HIPD 800. FIGS. 5C-1 and 5C-2 show a third AR system 500c and third example user interactions using a wrist-wearable device 600, a head-wearable device (e.g., VR device 710), and/or an HIPD 800. FIGS. 5D1 and 5D2 show a fourth AR system 500d and fourth example user interactions using a wrist-wearable device 600, VR device 710, and/or a smart textile-based garment 900 (e.g., wearable gloves haptic gloves). As the skilled artisan will appreciate upon reading the descriptions provided herein, the above-example AR systems (described in detail below) can perform various functions and/or operations.

The wrist-wearable device 600 and one or more of its components are described below in reference to FIGS. 6A-6B; the head-wearable devices and their one or more components are described below in reference to FIGS. 7A-7D; and the HIPD 800 and its one or more components are described below in reference to FIGS. 8A-8B. The smart textile-based garment 900 and its one or more components are described below in reference to FIGS. 9A-9C. The wrist-wearable device 600, the head-wearable devices, and/or the HIPD 800 can communicatively couple via a network 525 (e.g., cellular, near field, Wi-Fi, personal area network, wireless LAN, etc.). Additionally, the wrist-wearable device 600, the head-wearable devices, and/or the HIPD 800 can also communicatively couple with one or more servers 530, computers 540 (e.g., laptops, computers, etc.), mobile devices 550 (e.g., smartphones, tablets, etc.), and/or other electronic devices via the network 525 (e.g., cellular, near field, Wi-Fi, personal area network, wireless LAN, etc.). Similarly, the smart textile-based garment 900, when used, can also communicatively couple with the wrist-wearable device 600, the head-wearable devices, the HIPD 800, the one or more servers 530, the computers 540, the mobile devices 550, and/or other electronic devices via the network 525.

Turning to FIG. 5A, a user 502 is shown wearing the wrist-wearable device 600 and the AR device 700, and having the HIPD 800 on their desk. The wrist-wearable device 600, the AR device 700, and the HIPD 800 facilitate user interaction with an AR environment. In particular, as shown by the first AR system 500a, the wrist-wearable device 600, the AR device 700, and/or the HIPD 800 cause presentation of one or more avatars 504, digital representations of contacts 506, and virtual objects 508. As discussed below, the user 502 can interact with the one or more avatars 504, digital representations of the contacts 506, and virtual objects 508 via the wrist-wearable device 600, the AR device 700, and/or the HIPD 800.

The user 502 can use any of the wrist-wearable device 600, the AR device 700, and/or the HIPD 800 to provide user inputs. For example, the user 502 can perform one or more hand gestures that are detected by the wrist-wearable device 600 (e.g., using one or more EMG sensors and/or IMUs, described below in reference to FIGS. 6A-6B) and/or AR device 700 (e.g. using one or more image sensor or camera, described below in reference to FIGS. 7A-7B) to provide a user input. Alternatively, or additionally, the user 502 can provide a user input via one or more touch surfaces of the wrist-wearable device 600, the AR device 700, and/or the HIPD 800, and/or voice commands captured by a microphone of the wrist-wearable device 600, the AR device 700, and/or the HIPD 800. In some embodiments, the wrist-wearable device 600, the AR device 700, and/or the HIPD 800 include a digital assistant to help the user in providing a user input (e.g., completing a sequence of operations, suggesting different operations or commands, providing reminders, confirming a command, etc.). In some embodiments, the user 502 can provide a user input via one or more facial gestures and/or facial expressions. For example, cameras of the wrist-wearable device 600, the AR device 700, and/or the HIPD 800 can track the user 502's eyes for navigating a user interface.

The wrist-wearable device 600, the AR device 700, and/or the HIPD 800 can operate alone or in conjunction to allow the user 502 to interact with the AR environment. In some embodiments, the HIPD 800 is configured to operate as a central hub or control center for the wrist-wearable device 600, the AR device 700, and/or another communicatively coupled device. For example, the user 502 can provide an input to interact with the AR environment at any of the wrist-wearable device 600, the AR device 700, and/or the HIPD 800, and the HIPD 800 can identify one or more back-end and front-end tasks to cause the performance of the requested interaction and distribute instructions to cause the performance of the one or more back-end and front-end tasks at the wrist-wearable device 600, the AR device 700, and/or the HIPD 800. In some embodiments, a back-end task is background processing task that is not perceptible by the user (e.g., rendering content, decompression, compression, etc.), and a front-end task is a user-facing task that is perceptible to the user (e.g., presenting information to the user, providing feedback to the user, etc.)). As described below in reference to FIGS. 8A-8B, the HIPD 800 can perform the back-end tasks and provide the wrist-wearable device 600 and/or the AR device 700 operational data corresponding to the performed back-end tasks such that the wrist-wearable device 600 and/or the AR device 700 can perform the front-end tasks. In this way, the HIPD 800, which has more computational resources and greater thermal headroom than the wrist-wearable device 600 and/or the AR device 700, performs computationally intensive tasks and reduces the computer resource utilization and/or power usage of the wrist-wearable device 600 and/or the AR device 700.

In the example shown by the first AR system 500a, the HIPD 800 identifies one or more back-end tasks and front-end tasks associated with a user request to initiate an AR video call with one or more other users (represented by the avatar 504 and the digital representation of the contact 506) and distributes instructions to cause the performance of the one or more back-end tasks and front-end tasks. In particular, the HIPD 800 performs back-end tasks for processing and/or rendering image data (and other data) associated with the AR video call and provides operational data associated with the performed back-end tasks to the AR device 700 such that the AR device 700 perform front-end tasks for presenting the AR video call (e.g., presenting the avatar 504 and the digital representation of the contact 506).

In some embodiments, the HIPD 800 can operate as a focal or anchor point for causing the presentation of information. This allows the user 502 to be generally aware of where information is presented. For example, as shown in the first AR system 500a, the avatar 504 and the digital representation of the contact 506 are presented above the HIPD 800. In particular, the HIPD 800 and the AR device 700 operate in conjunction to determine a location for presenting the avatar 504 and the digital representation of the contact 506. In some embodiments, information can be presented a predetermined distance from the HIPD 800 (e.g., within 5 meters). For example, as shown in the first AR system 500a, virtual object 508 is presented on the desk some distance from the HIPD 800. Similar to the above example, the HIPD 800 and the AR device 700 can operate in conjunction to determine a location for presenting the virtual object 508. Alternatively, in some embodiments, presentation of information is not bound by the HIPD 800. More specifically, the avatar 504, the digital representation of the contact 506, and the virtual object 508 do not have to be presented within a predetermined distance of the HIPD 800.

User inputs provided at the wrist-wearable device 600, the AR device 700, and/or the HIPD 800 are coordinated such that the user can use any device to initiate, continue, and/or complete an operation. For example, the user 502 can provide a user input to the AR device 700 to cause the AR device 700 to present the virtual object 508 and, while the virtual object 508 is presented by the AR device 700, the user 502 can provide one or more hand gestures via the wrist-wearable device 600 to interact and/or manipulate the virtual object 508.

FIG. 5B shows the user 502 wearing the wrist-wearable device 600 and the AR device 700, and holding the HIPD 800. In the second AR system 500b, the wrist-wearable device 600, the AR device 700, and/or the HIPD 800 are used to receive and/or provide one or more messages to a contact of the user 502. In particular, the wrist-wearable device 600, the AR device 700, and/or the HIPD 800 detect and coordinate one or more user inputs to initiate a messaging application and prepare a response to a received message via the messaging application.

In some embodiments, the user 502 initiates, via a user input, an application on the wrist-wearable device 600, the AR device 700, and/or the HIPD 800 that causes the application to initiate on at least one device. For example, in the second AR system 500b the user 502 performs a hand gesture associated with a command for initiating a messaging application (represented by messaging user interface 512); the wrist-wearable device 600 detects the hand gesture; and, based on a determination that the user 502 is wearing AR device 700, causes the AR device 700 to present a messaging user interface 512 of the messaging application. The AR device 700 can present the messaging user interface 512 to the user 502 via its display (e.g., as shown by user 502's field of view 510). In some embodiments, the application is initiated and ran on the device (e.g., the wrist-wearable device 600, the AR device 700, and/or the HIPD 800) that detects the user input to initiate the application, and the device provides another device operational data to cause the presentation of the messaging application. For example, the wrist-wearable device 600 can detect the user input to initiate a messaging application; initiate and run the messaging application; and provide operational data to the AR device 700 and/or the HIPD 800 to cause presentation of the messaging application. Alternatively, the application can be initiated and ran at a device other than the device that detected the user input. For example, the wrist-wearable device 600 can detect the hand gesture associated with initiating the messaging application and cause the HIPD 800 to run the messaging application and coordinate the presentation of the messaging application.

Further, the user 502 can provide a user input provided at the wrist-wearable device 600, the AR device 700, and/or the HIPD 800 to continue and/or complete an operation initiated are at another device. For example, after initiating the messaging application via the wrist-wearable device 600 and while the AR device 700 present the messaging user interface 512, the user 502 can provide an input at the HIPD 800 to prepare a response (e.g., shown by the swipe gesture performed on the HIPD 800). The user 502's gestures performed on the HIPD 800 can be provided and/or displayed on another device. For example, the user 502's swipe gestured performed on the HIPD 800 are displayed on a virtual keyboard of the messaging user interface 512 displayed by the AR device 700.

In some embodiments, the wrist-wearable device 600, the AR device 700, the HIPD 800, and/or other communicatively couple device can present one or more notifications to the user 502. The notification can be an indication of a new message, an incoming call, an application update, a status update, etc. The user 502 can select the notification via the wrist-wearable device 600, the AR device 700, the HIPD 800, and cause presentation of an application or operation associated with the notification on at least one device. For example, the user 502 can receive a notification that a message was received at the wrist-wearable device 600, the AR device 700, the HIPD 800, and/or other communicatively couple device and provide a user input at the wrist-wearable device 600, the AR device 700, and/or the HIPD 800 to review the notification, and the device detecting the user input can cause an application associated with the notification to be initiated and/or presented at the wrist-wearable device 600, the AR device 700, and/or the HIPD 800.

While the above example describes coordinated inputs used to interact with a messaging application, the skilled artisan will appreciate upon reading the descriptions that user inputs can be coordinated to interact with any number of applications including, but not limited to, gaming applications, social media applications, camera applications, web-based applications, financial applications, etc. For example, the AR device 700 can present to the user 502 game application data and the HIPD 800 can use a controller to provide inputs to the game. Similarly, the user 502 can use the wrist-wearable device 600 to initiate a camera of the AR device 700, and the user can use the wrist-wearable device 600, the AR device 700, and/or the HIPD 800 to manipulate the image capture (e.g., zoom in or out, apply filters, etc.) and capture image data.

Turning to FIGS. 5C-1 and 5C-2, the user 502 is shown wearing the wrist-wearable device 600 and a VR device 710, and holding the HIPD 800. In the third AR system 500c, the wrist-wearable device 600, the VR device 710, and/or the HIPD 800 are used to interact within an AR environment, such as a VR game or other AR application. While the VR device 710 present a representation of a VR game (e.g., first AR game environment 520) to the user 502, the wrist-wearable device 600, the VR device 710, and/or the HIPD 800 detect and coordinate one or more user inputs to allow the user 502 to interact with the VR game.

In some embodiments, the user 502 can provide a user input via the wrist-wearable device 600, the VR device 710, and/or the HIPD 800 that causes an action in a corresponding AR environment. For example, the user 502 in the third AR system 500c (shown in FIG. 5C-1) raises the HIPD 800 to prepare for a swing in the first AR game environment 520. The VR device 710, responsive to the user 502 raising the HIPD 800, causes the AR representation of the user 522 to perform a similar action (e.g., raise a virtual object, such as a virtual sword 524). In some embodiments, each device uses respective sensor data and/or image data to detect the user input and provide an accurate representation of the user 502's motion. For example, image sensors 858 (e.g., SLAM cameras or other cameras discussed below in FIGS. 8A and 8B) of the HIPD 800 can be used to detect a position of the 800 relative to the user 502's body such that the virtual object can be positioned appropriately within the first AR game environment 520; sensor data from the wrist-wearable device 600 can be used to detect a velocity at which the user 502 raises the HIPD 800 such that the AR representation of the user 522 and the virtual sword 524 are synchronized with the user 502's movements; and image sensors 726 (FIGS. 7A-7C) of the VR device 710 can be used to represent the user 502's body, boundary conditions, or real-world objects within the first AR game environment 520.

In FIG. 5C-2, the user 502 performs a downward swing while holding the HIPD 800. The user 502's downward swing is detected by the wrist-wearable device 600, the VR device 710, and/or the HIPD 800 and a corresponding action is performed in the first AR game environment 520. In some embodiments, the data captured by each device is used to improve the user's experience within the AR environment. For example, sensor data of the wrist-wearable device 600 can be used to determine a speed and/or force at which the downward swing is performed and image sensors of the HIPD 800 and/or the VR device 710 can be used to determine a location of the swing and how it should be represented in the first AR game environment 520, which, in turn, can be used as inputs for the AR environment (e.g., game mechanics, which can use detected speed, force, locations, and/or aspects of the user 502's actions to classify a user's inputs (e.g., user performs a light strike, hard strike, critical strike, glancing strike, miss, etc.) or calculate an output (e.g., amount of damage)).

While the wrist-wearable device 600, the VR device 710, and/or the HIPD 800 are described as detecting user inputs, in some embodiments, user inputs are detected at a single device (with the single device being responsible for distributing signals to the other devices for performing the user input). For example, the HIPD 800 can operate an application for generating the first AR game environment 520 and provide the VR device 710 with corresponding data for causing the presentation of the first AR game environment 520, as well as detect the 502's movements (while holding the HIPD 800) to cause the performance of corresponding actions within the first AR game environment 520. Additionally or alternatively, in some embodiments, operational data (e.g., sensor data, image data, application data, device data, and/or other data) of one or more devices is provide to a single device (e.g., the HIPD 800) to process the operational data and cause respective devices to perform an action associated with processed operational data.

FIGS. 5D-1 and 5D-2, the user 502 is shown wearing the wrist-wearable device 600, the VR device 710, smart textile-based garments 900. In the fourth AR system 500d, the wrist-wearable device 600, the VR device 710, and/or the smart textile-based garments 900 are used to interact within an AR environment (e.g., any AR system described above in reference to FIGS. 5A-5C-2). While the VR device 710 present a representation of a VR game (e.g., second AR game environment 530) to the user 502, the wrist-wearable device 600, the VR device 710, and/or the smart textile-based garments 900 detect and coordinate one or more user inputs to allow the user 502 to interact with the AR environment.

In some embodiments, the user 502 can provide a user input via the wrist-wearable device 600, the VR device 710, and/or the smart textile-based garments 900 that causes an action in a corresponding AR environment. For example, the user 502 in the fourth AR system 500d (shown in FIG. 5D-1) raises a hand wearing the smart textile-based garments 900 to prepare for cast spell or throw an object within the second AR game environment 530. The VR device 710, responsive to the user 502 holding up their hand (wearing a smart textile-based garments 900), causes the AR representation of the user 522 to perform a similar action (e.g., hold a virtual object, such as a casting a fireball 534). In some embodiments, each device uses respective sensor data and/or image data to detect the user input and provide an accurate representation of the user 502's motion.

In FIG. 5D-2, the user 502 performs a throwing motion while wearing the smart textile-based garment 900. The user 502's throwing motion is detected by the wrist-wearable device 600, the VR device 710, and/or the smart textile-based garments 900 and a corresponding action is performed in the second AR game environment 530. As described above, the data captured by each device is used to improve the user's experience within the AR environment. Although not shown, the smart textile-based garments 900 can be used in conjunction with an AR device 710 and/or an HIPD 800.

Having discussed example AR systems, devices for interacting with such AR systems, and other computing systems more generally, will now be discussed in greater detail below. Some definitions of devices and components that can be included in some or all of the example devices discussed below are defined here for ease of reference. A skilled artisan will appreciate that certain types of the components described below may be more suitable for a particular set of devices, and less suitable for a different set of devices. But subsequent reference to the components defined here should be considered to be encompassed by the definitions provided.

In some embodiments discussed below example devices and systems, including electronic devices and systems, will be discussed. Such example devices and systems are not intended to be limiting, and one of skill in the art will understand that alternative devices and systems to the example devices and systems described herein may be used to perform the operations and construct the systems and device that are described herein.

As described herein, an electronic device is a device that uses electrical energy to perform a specific function. It can be any physical object that contains electronic components such as transistors, resistors, capacitors, diodes, and integrated circuits. Examples of electronic devices include smartphones, laptops, digital cameras, televisions, gaming consoles, and music players, as well as the example electronic devices discussed herein. As described herein, an intermediary electronic device is a device that sits between two other electronic devices, and/or a subset of components of one or more electronic devices and facilitates communication, and/or data processing and/or data transfer between the respective electronic devices and/or electronic components.

Example Wrist-Wearable Devices

Figure 6A:
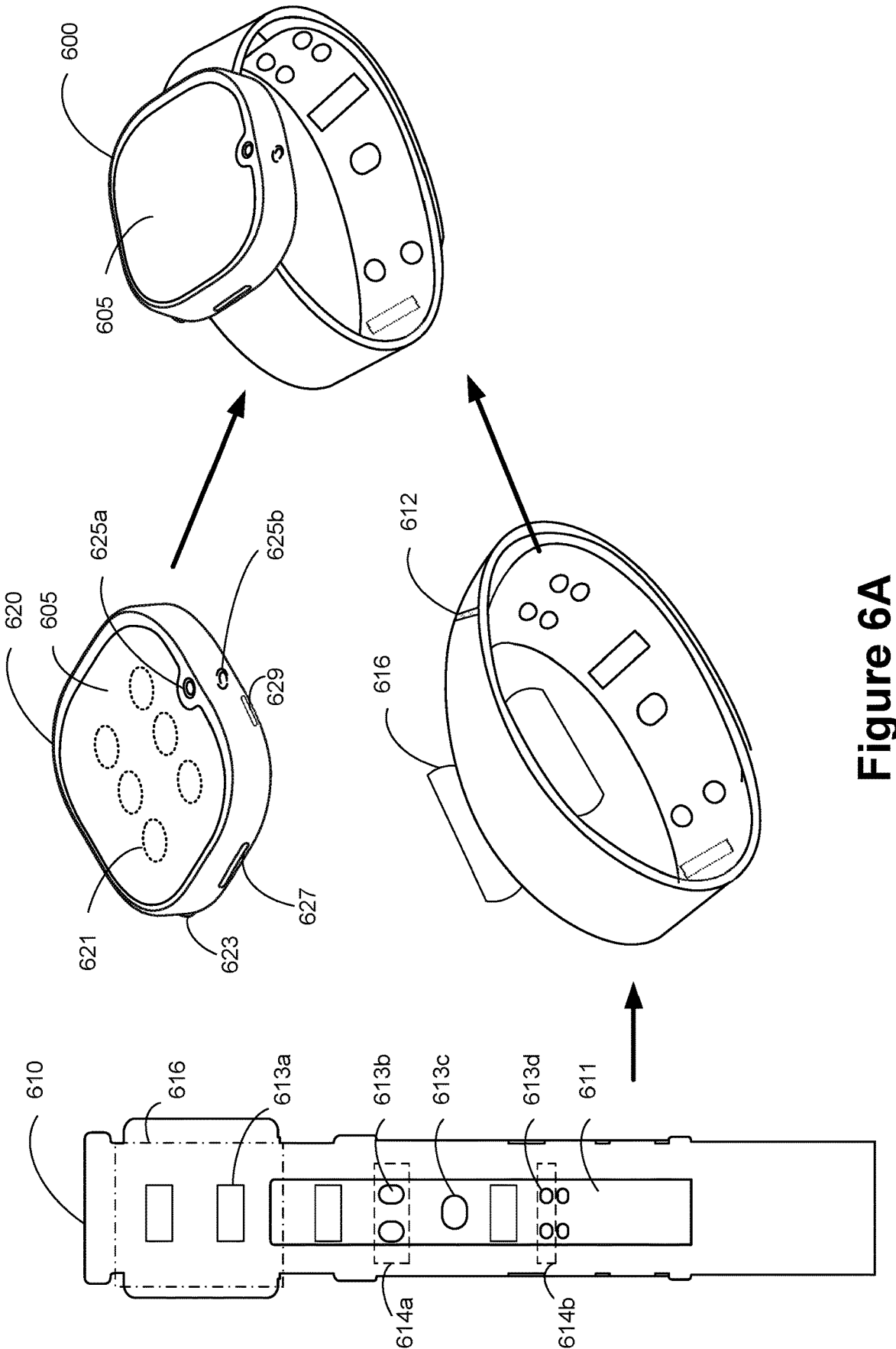
FIGS. 6A-6B illustrate an example wrist-wearable device 600, in accordance with some embodiments.
Figure 6B:
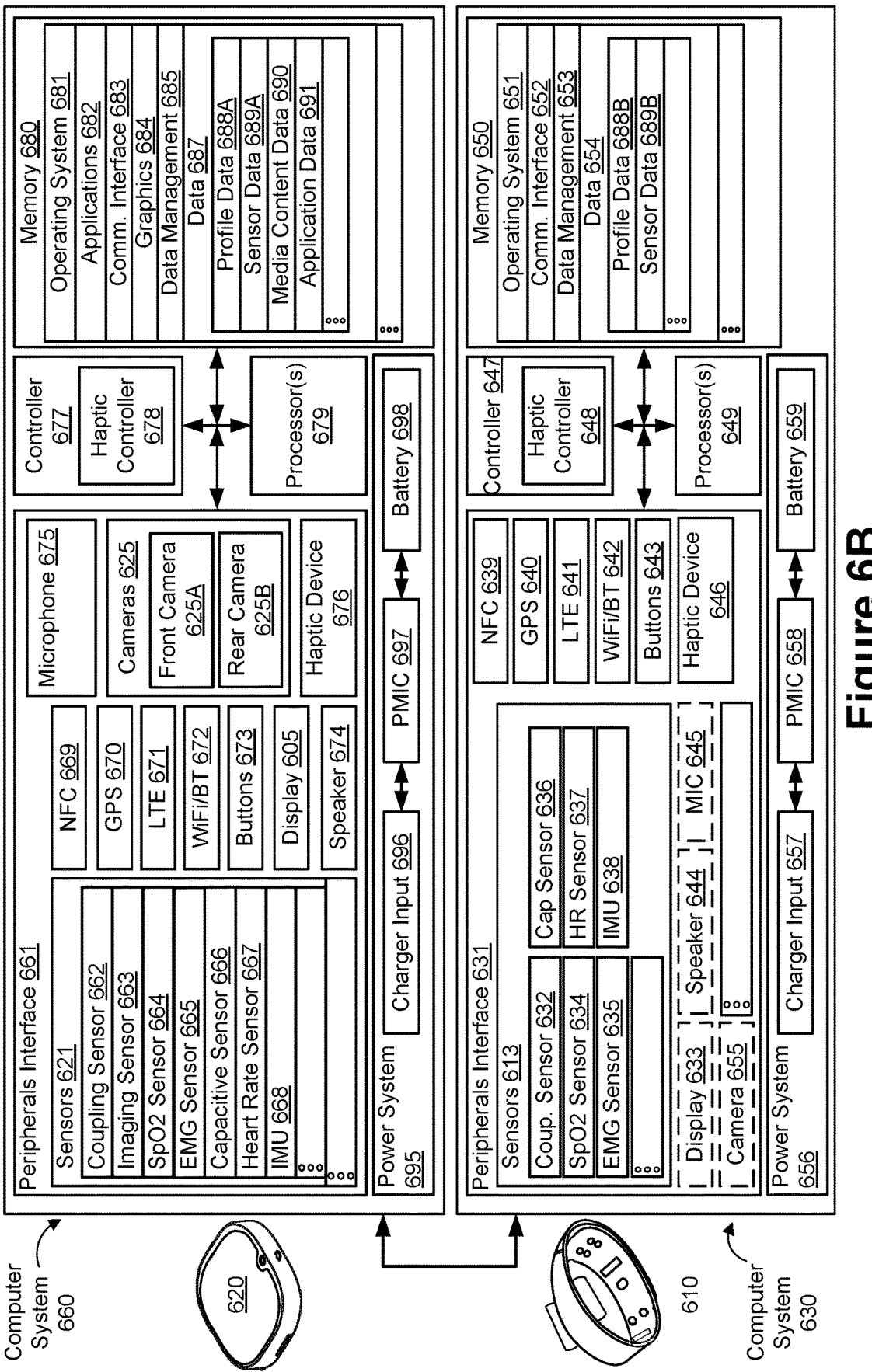

FIGS. 6A and 6B illustrate an example wrist-wearable device 600, in accordance with some embodiments. The wrist-wearable device 600 is an instance of the wearable device wearable device 104, described in reference to FIGS. 1A-4 herein, such that the wrist-wearable devices should be understood to have the features of the wrist-wearable device 600 and vice versa. FIG. 6A illustrates components of the wrist-wearable device 600, which can be used individually or in combination, including combinations that include other electronic devices and/or electronic components.

FIG. 6A shows a wearable band 610 and a watch body 620 (or capsule) being coupled, as discussed below, to form the wrist-wearable device 600. The wrist-wearable device 600 can perform various functions and/or operations associated with navigating through user interfaces and selectively opening applications, as well as the functions and/or operations described above with reference to FIGS. 1A-4.

As will be described in more detail below, operations executed by the wrist-wearable device 600 can include: (i) presenting content to a user (e.g., displaying visual content via a display 605); (ii) detecting (e.g., sensing) user input (e.g., sensing a touch on peripheral button 623 and/or at a touch screen of the display 605, a hand gesture detected by sensors (e.g., biopotential sensors)); (iii) sensing biometric data via one or more sensors 613 (e.g., neuromuscular signals, heart rate, temperature, sleep, etc.); messaging (e.g., text, speech, video, etc.); image capture via one or more imaging devices or cameras 625; wireless communications (e.g., cellular, near field, Wi-Fi, personal area network, etc.); location determination; financial transactions; providing haptic feedback; alarms; notifications; biometric authentication; health monitoring; sleep monitoring; etc.

The above-example functions can be executed independently in the watch body 620, independently in the wearable band 610, and/or via an electronic communication between the watch body 620 and the wearable band 610. In some embodiments, functions can be executed on the wrist-wearable device 600 while an AR environment is being presented (e.g., via one of the AR systems 500a to 500d). As the skilled artisan will appreciate upon reading the descriptions provided herein, the novel wearable devices described herein can be used with other types of AR environments.

The wearable band 610 can be configured to be worn by a user such that an inner (or inside) surface of the wearable structure 611 of the wearable band 610 is in contact with the user's skin. When worn by a user, sensors 613 contact the user's skin. The sensors 613 can sense biometric data such as a user's heart rate, saturated oxygen level, temperature, sweat level, neuromuscular signal sensors, or a combination thereof. The sensors 613 can also sense data about a user's environment including a user's motion, altitude, location, orientation, gait, acceleration, position, or a combination thereof. In some embodiment, the sensors 613 are configured to track a position and/or motion of the wearable band 610. The one or more sensors 613 can include any of the sensors defined above and/or discussed below with respect to FIG. 6B.

The one or more sensors 613 can be distributed on an inside and/or an outside surface of the wearable band 610. In some embodiments, the one or more sensors 613 are uniformly spaced along the wearable band 610. Alternatively, in some embodiments, the one or more sensors 613 are positioned at distinct points along the wearable band 610. As shown in FIG. 6A, the one or more sensors 613 can be the same or distinct. For example, in some embodiments, the one or more sensors 613 can be shaped as a pill (e.g., sensor 613a), an oval, a circle a square, an oblong (e.g., sensor 613c) and/or any other shape that maintains contact with the user's skin (e.g., such that neuromuscular signal and/or other biometric data can be accurately measured at the user's skin). In some embodiments, the one or more sensors 613 are aligned to form pairs of sensors (e.g., for sensing neuromuscular signals based on differential sensing within each respective sensor). For example, sensor 613b is aligned with an adjacent sensor to form sensor pair 614a and sensor 613d aligned with an adjacent sensor to form sensor pair 614b. In some embodiments, the wearable band 610 does not have a sensor pair. Alternatively, in some embodiments, the wearable band 610 has a predetermined number of sensor pairs (one pair of sensors, three pairs of sensors, four pairs of sensors, six pairs of sensors, sixteen pairs of sensors, etc.).

The wearable band 610 can include any suitable number of sensors 613. In some embodiments, the number and arrangement of sensors 613 depends on the particular application for which the wearable band 610 is used. For instance, a wearable band 610 configured as an armband, wristband, or chest-band may include a plurality of sensors 613 with different number of sensors 613 and different arrangement for each use case, such as medical use cases as compared to gaming or general day-to-day use cases.

In accordance with some embodiments, the wearable band 610 further includes an electrical ground electrode and a shielding electrode. The electrical ground and shielding electrodes, like the sensors 613, can be distributed on the inside surface of the wearable band 610 such that they contact a portion of the user's skin. For example, the electrical ground and shielding electrodes can be at an inside surface of coupling mechanism 616 or an inside surface of a wearable structure 611. The electrical ground and shielding electrodes can be formed and/or use the same components as the sensors 613. In some embodiments, the wearable band 610 includes more than one electrical ground electrode and more than one shielding electrode.

The sensors 613 can be formed as part of the wearable structure 611 of the wearable band 610. In some embodiments, the sensors 613 are flush or substantially flush with the wearable structure 611 such that they do not extend beyond the surface of the wearable structure 611. While flush with the wearable structure 611, the sensors 613 are still configured to contact the user's skin (e.g., via a skin-contacting surface). Alternatively, in some embodiments, the sensors 613 extend beyond the wearable structure 611 a predetermined distance (e.g., 0.1-2 mm) to make contact and depress into the user's skin. In some embodiment, the sensors 613 are coupled to an actuator (not shown) configured to adjust an extension height (e.g., a distance from the surface of the wearable structure 611) of the sensors 613 such that the sensors 613 make contact and depress into the user's skin. In some embodiments, the actuators adjust the extension height between 0.01 mm-1.2 mm. This allows the user to customize the positioning of the sensors 613 to improve the overall comfort of the wearable band 610 when worn while still allowing the sensors 613 to contact the user's skin. In some embodiments, the sensors 613 are indistinguishable from the wearable structure 611 when worn by the user.

The wearable structure 611 can be formed of an elastic material, elastomers, etc. configured to be stretched and fitted to be worn by the user. In some embodiments, the wearable structure 611 is a textile or woven fabric. As described above, the sensors 613 can be formed as part of a wearable structure 611. For example, the sensors 613 can be molded into the wearable structure 611 or be integrated into a woven fabric (e.g., the sensors 613 can be sewn into the fabric and mimic the pliability of fabric (e.g., the sensors 613 can be constructed from a series woven strands of fabric)).

The wearable structure 611 can include flexible electronic connectors that interconnect the sensors 613, the electronic circuitry, and/or other electronic components (described below in reference to FIG. 6B) that are enclosed in the wearable band 610. In some embodiments, the flexible electronic connectors are configured to interconnect the sensors 613, the electronic circuitry, and/or other electronic components of the wearable band 610 with respective sensors and/or other electronic components of another electronic device (e.g., watch body 620). The flexible electronic connectors are configured to move with the wearable structure 611 such that the user adjustment to the wearable structure 611 (e.g., resizing, pulling, folding, etc.) does not stress or strain the electrical coupling of components of the wearable band 610.

As described above, the wearable band 610 is configured to be worn by a user. In particular, the wearable band 610 can be shaped or otherwise manipulated to be worn by a user. For example, the wearable band 610 can be shaped to have a substantially circular shape such that it can be configured to be worn on the user's lower arm or wrist. Alternatively, the wearable band 610 can be shaped to be worn on another body part of the user, such as the user's upper arm (e.g., around a bicep), forearm, chest, legs, etc. The wearable band 610 can include a retaining mechanism 612 (e.g., a buckle, a hook and loop fastener, etc.) for securing the wearable band 610 to the user's wrist or other body part. While the wearable band 610 is worn by the user, the sensors 613 sense data (referred to as sensor data) from the user's skin. In particular, the sensors 613 of the wearable band 610 obtain (e.g., sense and record) neuromuscular signals.

The sensed data (e.g., sensed neuromuscular signals) can be used to detect and/or determine the user's intention to perform certain motor actions. In particular, the sensors 613 sense and record neuromuscular signals from the user as the user performs muscular activations (e.g., movements, gestures, etc.). The detected and/or determined motor actions (e.g., phalange (or digits) movements, wrist movements, hand movements, and/or other muscle intentions) can be used to determine control commands or control information (instructions to perform certain commands after the data is sensed) for causing a computing device to perform one or more input commands. For example, the sensed neuromuscular signals can be used to control certain user interfaces displayed on the display 605 of the wrist-wearable device 600 and/or can be transmitted to a device responsible for rendering an artificial-reality environment (e.g., a head-mounted display) to perform an action in an associated artificial-reality environment, such as to control the motion of a virtual device displayed to the user. The muscular activations performed by the user can include static gestures, such as placing the user's hand palm down on a table; dynamic gestures, such as grasping a physical or virtual object; and covert gestures that are imperceptible to another person, such as slightly tensing a joint by co-contracting opposing muscles or using sub-muscular activations. The muscular activations performed by the user can include symbolic gestures (e.g., gestures mapped to other gestures, interactions, or commands, for example, based on a gesture vocabulary that specifies the mapping of gestures to commands).

The sensor data sensed by the sensors 613 can be used to provide a user with an enhanced interaction with a physical object (e.g., devices communicatively coupled with the wearable band 610) and/or a virtual object in an artificial-reality application generated by an artificial-reality system (e.g., user interface objects presented on the display 605, or another computing device (e.g., a smartphone)).

In some embodiments, the wearable band 610 includes one or more haptic devices 646 (FIG. 6B; e.g., a vibratory haptic actuator) that are configured to provide haptic feedback (e.g., a cutaneous and/or kinesthetic sensation, etc.) to the user's skin. The sensors 613, and/or the haptic devices 646 can be configured to operate in conjunction with multiple applications including, without limitation, health monitoring, social media, games, and artificial reality (e.g., the applications associated with artificial reality).

The wearable band 610 can also include coupling mechanism 616 (e.g., a cradle or a shape of the coupling mechanism can correspond to shape of the watch body 620 of the wrist-wearable device 600) for detachably coupling a capsule (e.g., a computing unit) or watch body 620 (via a coupling surface of the watch body 620) to the wearable band 610. In particular, the coupling mechanism 616 can be configured to receive a coupling surface proximate to the bottom side of the watch body 620 (e.g., a side opposite to a front side of the watch body 620 where the display 605 is located), such that a user can push the watch body 620 downward into the coupling mechanism 616 to attach the watch body 620 to the coupling mechanism 616. In some embodiments, the coupling mechanism 616 can be configured to receive a top side of the watch body 620 (e.g., a side proximate to the front side of the watch body 620 where the display 605 is located) that is pushed upward into the cradle, as opposed to being pushed downward into the coupling mechanism 616. In some embodiments, the coupling mechanism 616 is an integrated component of the wearable band 610 such that the wearable band 610 and the coupling mechanism 616 are a single unitary structure. In some embodiments, the coupling mechanism 616 is a type of frame or shell that allows the watch body 620 coupling surface to be retained within or on the wearable band 610 coupling mechanism 616 (e.g., a cradle, a tracker band, a support base, a clasp, etc.).

The coupling mechanism 616 can allow for the watch body 620 to be detachably coupled to the wearable band 610 through a friction fit, magnetic coupling, a rotation-based connector, a shear-pin coupler, a retention spring, one or more magnets, a clip, a pin shaft, a hook and loop fastener, or a combination thereof. A user can perform any type of motion to couple the watch body 620 to the wearable band 610 and to decouple the watch body 620 from the wearable band 610. For example, a user can twist, slide, turn, push, pull, or rotate the watch body 620 relative to the wearable band 610, or a combination thereof, to attach the watch body 620 to the wearable band 610 and to detach the watch body 620 from the wearable band 610. Alternatively, as discussed below, in some embodiments, the watch body 620 can be decoupled from the wearable band 610 by actuation of the release mechanism 629.

The wearable band 610 can be coupled with a watch body 620 to increase the functionality of the wearable band 610 (e.g., converting the wearable band 610 into a wrist-wearable device 600, adding an additional computing unit and/or battery to increase computational resources and/or a battery life of the wearable band 610, adding additional sensors to improve sensed data, etc.). As described above, the wearable band 610 (and the coupling mechanism 616) is configured to operate independently (e.g., execute functions independently) from watch body 620. For example, the coupling mechanism 616 can include one or more sensors 613 that contact a user's skin when the wearable band 610 is worn by the user and provide sensor data for determining control commands.

A user can detach the watch body 620 (or capsule) from the wearable band 610 in order to reduce the encumbrance of the wrist-wearable device 600 to the user. For embodiments in which the watch body 620 is removable, the watch body 620 can be referred to as a removable structure, such that in these embodiments the wrist-wearable device 600 includes a wearable portion (e.g., the wearable band 610) and a removable structure (the watch body 620).

Turning to the watch body 620, the watch body 620 can have a substantially rectangular or circular shape. The watch body 620 is configured to be worn by the user on their wrist or on another body part. More specifically, the watch body 620 is sized to be easily carried by the user, attached on a portion of the user's clothing, and/or coupled to the wearable band 610 (forming the wrist-wearable device 600). As described above, the watch body 620 can have a shape corresponding to the coupling mechanism 616 of the wearable band 610. In some embodiments, the watch body 620 includes a single release mechanism 629 or multiple release mechanisms (e.g., two release mechanisms 629 positioned on opposing sides of the watch body 620, such as spring-loaded buttons) for decoupling the watch body 620 and the wearable band 610. The release mechanism 629 can include, without limitation, a button, a knob, a plunger, a handle, a lever, a fastener, a clasp, a dial, a latch, or a combination thereof.

A user can actuate the release mechanism 629 by pushing, turning, lifting, depressing, shifting, or performing other actions on the release mechanism 629. Actuation of the release mechanism 629 can release (e.g., decouple) the watch body 620 from the coupling mechanism 616 of the wearable band 610, allowing the user to use the watch body 620 independently from wearable band 610, and vice versa. For example, decoupling the watch body 620 from the wearable band 610 can allow the user to capture images using rear-facing camera 625B. Although the is shown positioned at a corner of watch body 620, the release mechanism 629 can be positioned anywhere on watch body 620 that is convenient for the user to actuate. In addition, in some embodiments, the wearable band 610 can also include a respective release mechanism for decoupling the watch body 620 from the coupling mechanism 616. In some embodiments, the release mechanism 629 is optional and the watch body 620 can be decoupled from the coupling mechanism 616 as described above (e.g., via twisting, rotating, etc.).

The watch body 620 can include one or more peripheral buttons 623 and 627 for performing various operations at the watch body 620. For example, the peripheral buttons 623 and 627 can be used to turn on or wake (e.g., transition from a sleep state to an active state) the display 605, unlock the watch body 620, increase or decrease a volume, increase or decrease a brightness, interact with one or more applications, interact with one or more user interfaces, etc. Additionally, or alternatively, in some embodiments, the display 605 operates as a touch screen and allows the user to provide one or more inputs for interacting with the watch body 620.

In some embodiments, the watch body 620 includes one or more sensors 621. The sensors 621 of the watch body 620 can be the same or distinct from the sensors 613 of the wearable band 610. The sensors 621 of the watch body 620 can be distributed on an inside and/or an outside surface of the watch body 620. In some embodiments, the sensors 621 are configured to contact a user's skin when the watch body 620 is worn by the user. For example, the sensors 621 can be placed on the bottom side of the watch body 620 and the coupling mechanism 616 can be a cradle with an opening that allows the bottom side of the watch body 620 to directly contact the user's skin. Alternatively, in some embodiments, the watch body 620 does not include sensors that are configured to contact the user's skin (e.g., including sensors internal and/or external to the watch body 620 that configured to sense data of the watch body 620 and the watch body 620's surrounding environment). In some embodiment, the sensors 613 are configured to track a position and/or motion of the watch body 620.

The watch body 620 and the wearable band 610 can share data using a wired communication method (e.g., a Universal Asynchronous Receiver/Transmitter (UART), a USB transceiver, etc.) and/or a wireless communication method (e.g., near field communication, Bluetooth, etc.). For example, the watch body 620 and the wearable band 610 can share data sensed by the sensors 613 and 621, as well as application and device specific information (e.g., active and/or available applications, output devices (e.g., display, speakers, etc.), input devices (e.g., touch screen, microphone, imaging sensors, etc.).

In some embodiments, the watch body 620 can include, without limitation, a front-facing camera 625A and/or a rear-facing camera 625B, sensors 621 (e.g., a biometric sensor, an IMU, a heart rate sensor, a saturated oxygen sensor, a neuromuscular signal sensor, an altimeter sensor, a temperature sensor, a bioimpedance sensor, a pedometer sensor, an optical sensor (e.g., imaging sensor 663; FIG. 6B), a touch sensor, a sweat sensor, etc.). In some embodiments, the watch body 620 can include one or more haptic devices 676 (FIG. 6B; a vibratory haptic actuator) that is configured to provide haptic feedback (e.g., a cutaneous and/or kinesthetic sensation, etc.) to the user. The sensors 621 and/or the haptic device 676 can also be configured to operate in conjunction with multiple applications including, without limitation, health monitoring applications, social media applications, game applications, and artificial reality applications (e.g., the applications associated with artificial reality).

As described above, the watch body 620 and the wearable band 610, when coupled, can form the wrist-wearable device 600. When coupled, the watch body 620 and wearable band 610 operate as a single device to execute functions (operations, detections, communications, etc.) described herein. In some embodiments, each device is provided with particular instructions for performing the one or more operations of the wrist-wearable device 600. For example, in accordance with a determination that the watch body 620 does not include neuromuscular signal sensors, the wearable band 610 can include alternative instructions for performing associated instructions (e.g., providing sensed neuromuscular signal data to the watch body 620 via a different electronic device). Operations of the wrist-wearable device 600 can be performed by the watch body 620 alone or in conjunction with the wearable band 610 (e.g., via respective processors and/or hardware components) and vice versa. In some embodiments, operations of the wrist-wearable device 600, the watch body 620, and/or the wearable band 610 can be performed in conjunction with one or more processors and/or hardware components of another communicatively coupled device (e.g., the HIPD 800; FIGS. 8A-8B).

As described below with reference to the block diagram of FIG. 6B, the wearable band 610 and/or the watch body 620 can each include independent resources required to independently execute functions. For example, the wearable band 610 and/or the watch body 620 can each include a power source (e.g., a battery), a memory, data storage, a processor (e.g., a central processing unit (CPU)), communications, a light source, and/or input/output devices.

FIG. 6B shows block diagrams of a computing system 630 corresponding to the wearable band 610, and a computing system 660 corresponding to the watch body 620, according to some embodiments. A computing system of the wrist-wearable device 600 includes a combination of components of the wearable band computing system 630 and the watch body computing system 660, in accordance with some embodiments.

The watch body 620 and/or the wearable band 610 can include one or more components shown in watch body computing system 660. In some embodiments, a single integrated circuit includes all or a substantial portion of the components of the watch body computing system 660 are included in a single integrated circuit. Alternatively, in some embodiments, components of the watch body computing system 660 are included in a plurality of integrated circuits that are communicatively coupled. In some embodiments, the watch body computing system 660 is configured to couple (e.g., via a wired or wireless connection) with the wearable band computing system 630, which allows the computing systems to share components, distribute tasks, and/or perform other operations described herein (individually or as a single device).

The watch body computing system 660 can include one or more processors 679, a controller 677, a peripherals interface 661, a power system 695, and memory (e.g., a memory 680), each of which are defined above and described in more detail below.

The power system 695 can include a charger input 696, a power-management integrated circuit (PMIC) 697, and a battery 698, each are which are defined above. In some embodiments, a watch body 620 and a wearable band 610 can have respective charger inputs (e.g., charger input 696 and 657), respective batteries (e.g., battery 698 and 659), and can share power with each other (e.g., the watch body 620 can power and/or charge the wearable band 610, and vice versa). Although watch body 620 and/or the wearable band 610 can include respective charger inputs, a single charger input can charge both devices when coupled. The watch body 620 and the wearable band 610 can receive a charge using a variety of techniques. In some embodiments, the watch body 620 and the wearable band 610 can use a wired charging assembly (e.g., power cords) to receive the charge. Alternatively, or in addition, the watch body 620 and/or the wearable band 610 can be configured for wireless charging. For example, a portable charging device can be designed to mate with a portion of watch body 620 and/or wearable band 610 and wirelessly deliver usable power to a battery of watch body 620 and/or wearable band 610. The watch body 620 and the wearable band 610 can have independent power systems (e.g., power system 695 and 656) to enable each to operate independently. The watch body 620 and wearable band 610 can also share power (e.g., one can charge the other) via respective PMICs (e.g., PMICs 697 and 658) that can share power over power and ground conductors and/or over wireless charging antennas.

In some embodiments, the peripherals interface 661 can include one or more sensors 621, many of which listed below are defined above. The sensors 621 can include one or more coupling sensor 662 for detecting when the watch body 620 is coupled with another electronic device (e.g., a wearable band 610). The sensors 621 can include imaging sensors 663 (one or more of the cameras 625, and/or separate imaging sensors 663 (e.g., thermal-imaging sensors)). In some embodiments, the sensors 621 include one or more SpO2 sensors 664. In some embodiments, the sensors 621 include one or more biopotential-signal sensors (e.g., EMG sensors 665, which may be disposed on a user-facing portion of the watch body 620 and/or the wearable band 610). In some embodiments, the sensors 621 include one or more capacitive sensors 666. In some embodiments, the sensors 621 include one or more heart rate sensors 667. In some embodiments, the sensors 621 include one or more IMUs 668. In some embodiments, one or more IMUs 668 can be configured to detect movement of a user's hand or other location that the watch body 620 is placed or held).

In some embodiments, the peripherals interface 661 includes a near-field communication (NFC) component 669, a global-position system (GPS) component 670, a long-term evolution (LTE) component 671, and/or a Wi-Fi and/or Bluetooth communication component 672. In some embodiments, the peripherals interface 661 includes one or more buttons 673 (e.g., the peripheral buttons 623 and 627 in FIG. 6A), which, when selected by a user, cause operation to be performed at the watch body 620. In some embodiments, the peripherals interface 661 includes one or more indicators, such as a light emitting diode (LED), to provide a user with visual indicators (e.g., message received, low battery, active microphone and/or camera, etc.).

The watch body 620 can include at least one display 605, for displaying visual representations of information or data to the user, including user-interface elements and/or three-dimensional virtual objects. The display can also include a touch screen for inputting user inputs, such as touch gestures, swipe gestures, and the like. The watch body 620 can include at least one speaker 674 and at least one microphone 675 for providing audio signals to the user and receiving audio input from the user. The user can provide user inputs through the microphone 675 and can also receive audio output from the speaker 674 as part of a haptic event provided by the haptic controller 678. The watch body 620 can include at least one camera 625, including a front-facing camera 625A and a rear-facing camera 625B. The cameras 625 can include ultra-wide-angle cameras, wide angle cameras, fish-eye cameras, spherical cameras, telephoto cameras, a depth-sensing cameras, or other types of cameras.

The watch body computing system 660 can include one or more haptic controllers 678 and associated componentry (e.g., haptic devices 676) for providing haptic events at the watch body 620 (e.g., a vibrating sensation or audio output in response to an event at the watch body 620). The haptic controllers 678 can communicate with one or more haptic devices 676, such as electroacoustic devices, including a speaker of the one or more speakers 674 and/or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). The haptic controller 678 can provide haptic events to that are capable of being sensed by a user of the watch body 620. In some embodiments, the one or more haptic controllers 678 can receive input signals from an application of the applications 682.

In some embodiments, the computer system 630 and/or the computer system 660 can include memory 680, which can be controlled by a memory controller of the one or more controllers 677 and/or one or more processors 679. In some embodiments, software components stored in the memory 680 include one or more applications 682 configured to perform operations at the watch body 620. In some embodiments, the one or more applications 682 include games, word processors, messaging applications, calling applications, web browsers, social media applications, media streaming applications, financial applications, calendars, clocks, etc. In some embodiments, software components stored in the memory 680 include one or more communication interface modules 683 as defined above. In some embodiments, software components stored in the memory 680 include one or more graphics modules 684 for rendering, encoding, and/or decoding audio and/or visual data; and one or more data management modules 685 for collecting, organizing, and/or providing access to the data 687 stored in memory 680. In some embodiments, one or more of applications 682 and/or one or more modules can work in conjunction with one another to perform various tasks at the watch body 620.

In some embodiments, software components stored in the memory 680 can include one or more operating systems 681 (e.g., a Linux-based operating system, an Android operating system, etc.). The memory 680 can also include data 687. The data 687 can include profile data 688A, sensor data 689A, media content data 690, and application data 691.

It should be appreciated that the watch body computing system 660 is an example of a computing system within the watch body 620, and that the watch body 620 can have more or fewer components than shown in the watch body computing system 660, combine two or more components, and/or have a different configuration and/or arrangement of the components. The various components shown in watch body computing system 660 are implemented in hardware, software, firmware, or a combination thereof, including one or more signal processing and/or application-specific integrated circuits.

Turning to the wearable band computing system 630, one or more components that can be included in the wearable band 610 are shown. The wearable band computing system 630 can include more or fewer components than shown in the watch body computing system 660, combine two or more components, and/or have a different configuration and/or arrangement of some or all of the components. In some embodiments, all, or a substantial portion of the components of the wearable band computing system 630 are included in a single integrated circuit. Alternatively, in some embodiments, components of the wearable band computing system 630 are included in a plurality of integrated circuits that are communicatively coupled. As described above, in some embodiments, the wearable band computing system 630 is configured to couple (e.g., via a wired or wireless connection) with the watch body computing system 660, which allows the computing systems to share components, distribute tasks, and/or perform other operations described herein (individually or as a single device).

The wearable band computing system 630, similar to the watch body computing system 660, can include one or more processors 649, one or more controllers 647 (including one or more haptics controller 648), a peripherals interface 631 that can includes one or more sensors 613 and other peripheral devices, power source (e.g., a power system 656), and memory (e.g., a memory 650) that includes an operating system (e.g., an operating system 651), data (e.g., data 654 including profile data 688B, sensor data 689B, etc.), and one or more modules (e.g., a communications interface module 652, a data management module 653, etc.).

The one or more sensors 613 can be analogous to sensors 621 of the computer system 660 and in light of the definitions above. For example, sensors 613 can include one or more coupling sensors 632, one or more SpO2 sensor 634, one or more EMG sensors 635, one or more capacitive sensor 636, one or more heart rate sensor 637, and one or more IMU 638.

The peripherals interface 631 can also include other components analogous to those included in the peripheral interface 661 of the computer system 660, including an NFC component 639, a GPS component 640, an LTE component 641, a Wi-Fi and/or Bluetooth communication component 642, and/or one or more haptic devices 676 as described above in reference to peripherals interface 661. In some embodiments, the peripherals interface 631 includes one or more buttons 643, a display 633, a speaker 644, a microphone 645, and a camera 655. In some embodiments, the peripherals interface 631 includes one or more indicators, such as an LED.

It should be appreciated that the wearable band computing system 630 is an example of a computing system within the wearable band 610, and that the wearable band 610 can have more or fewer components than shown in the wearable band computing system 630, combine two or more components, and/or have a different configuration and/or arrangement of the components. The various components shown in wearable band computing system 630 can be implemented in one or a combination of hardware, software, firmware, including one or more signal processing and/or application-specific integrated circuits.

The wrist-wearable device 600 with respect to FIG. 6A is an example of the wearable band 610 and the watch body 620 coupled, so the wrist-wearable device 600 will be understood to include the components shown and described for the wearable band computing system 630 and the watch body computing system 660. In some embodiments, wrist-wearable device 600 has a split architecture (e.g., a split mechanical architecture, a split electrical architecture) between the watch body 620 and the wearable band 610. In other words, all of the components shown in the wearable band computing system 630 and the watch body computing system 660 can be housed or otherwise disposed in a combined watch device 600, or within individual components of the watch body 620, wearable band 610, and/or portions thereof (e.g., a coupling mechanism 616 of the wearable band 610).

The techniques described above can be used with any device for sensing neuromuscular signals, including the arm-wearable devices of FIG. 6A-6B, but could also be used with other types of wearable devices for sensing neuromuscular signals (such as body-wearable or head-wearable devices that might have neuromuscular sensors closer to the brain or spinal column).

In some embodiments, a wrist-wearable device 600 can be used in conjunction with a head-wearable device described below (e.g., AR device 700 and VR device 710) and/or an HIPD 800; and the wrist-wearable device 600 can also be configured to be used to allow a user to control aspect of the artificial reality (e.g., by using EMG-based gestures to control user interface objects in the artificial reality and/or by allowing a user to interact with the touchscreen on the wrist-wearable device to also control aspects of the artificial reality). In some embodiments, a wrist-wearable device 600 can also be used in conjunction with a wearable garment, such as smart textile-based garment 900 described below in reference to FIGS. 9A-9C. Having thus described example wrist-wearable device, attention will now be turned to example head-wearable devices, such AR device 700 and VR device 710.

Example Head-Wearable Devices

Figure 7A:
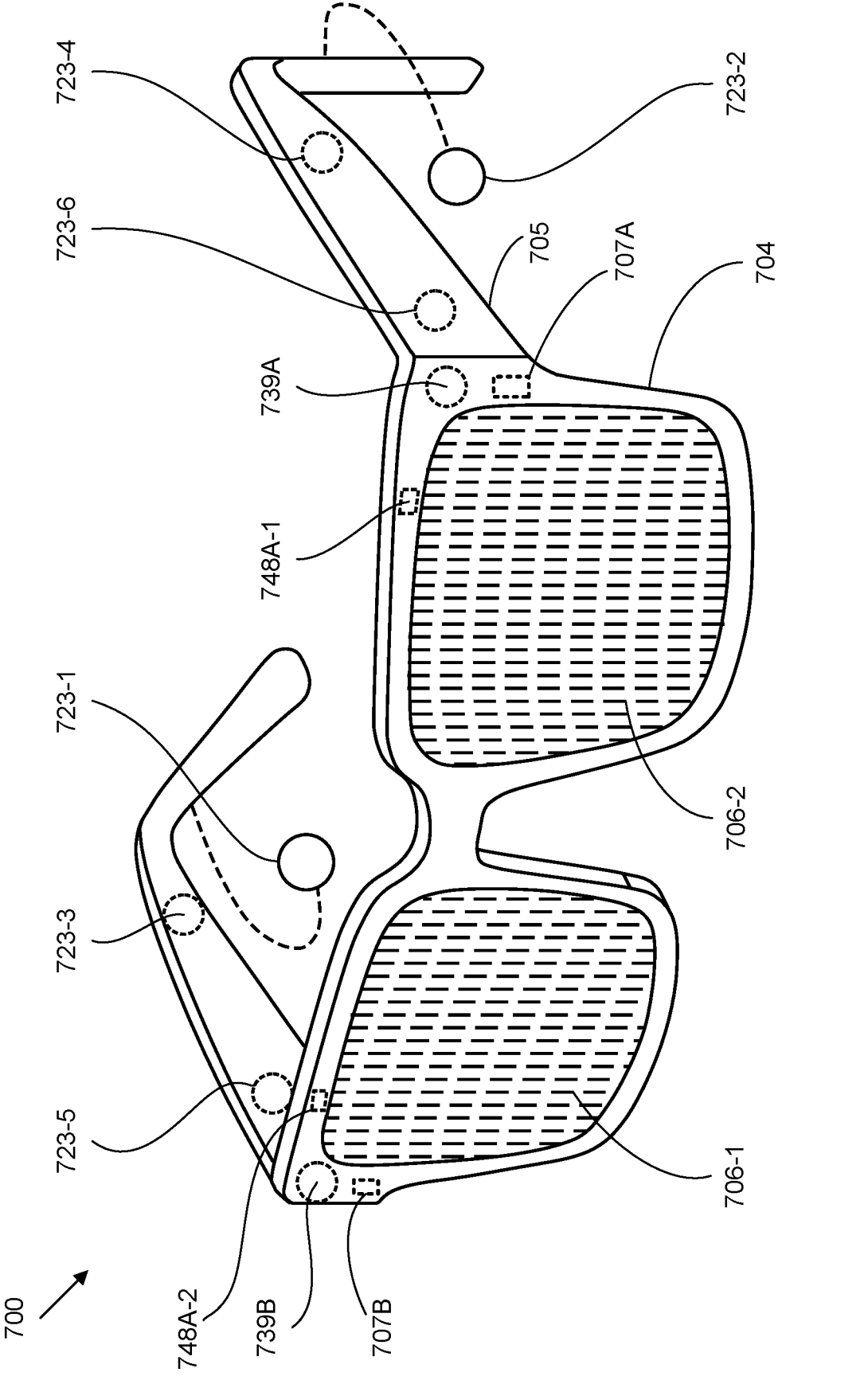
FIGS. 7A-7C illustrate example head-wearable devices, in accordance with some embodiments.
Figures 1, 7B:
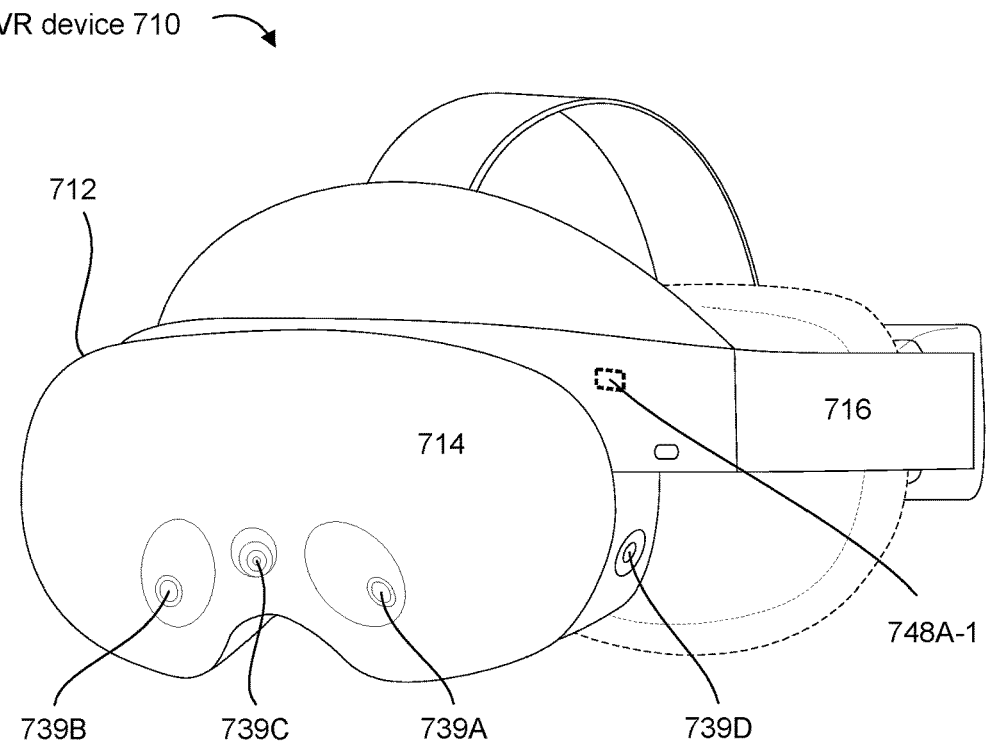
Figures 2, 7B:
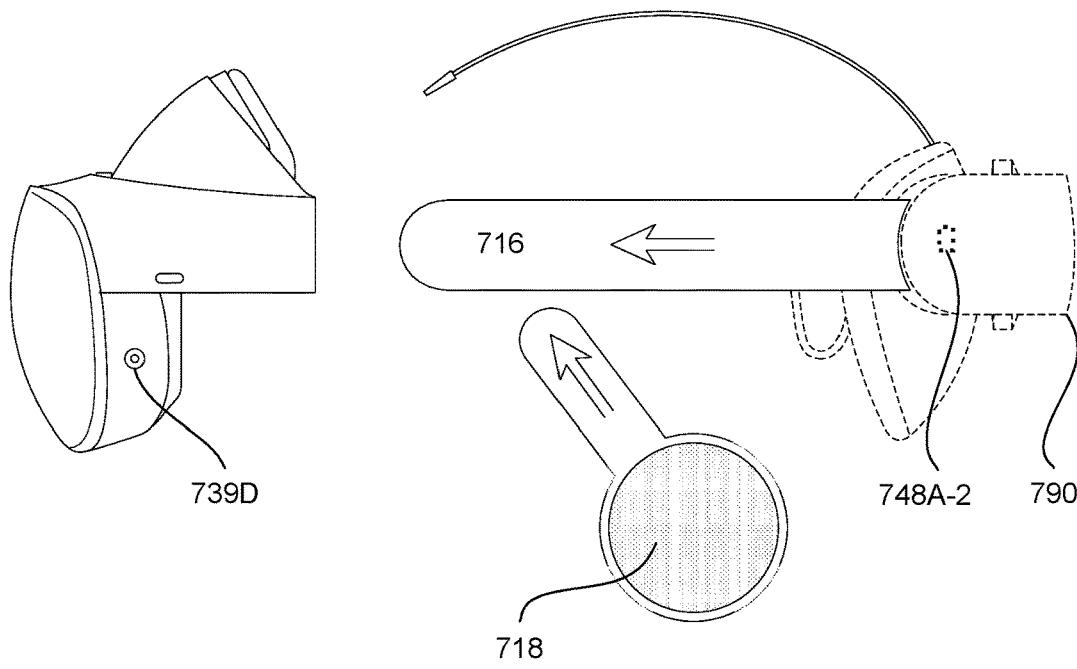
Figure 7C:
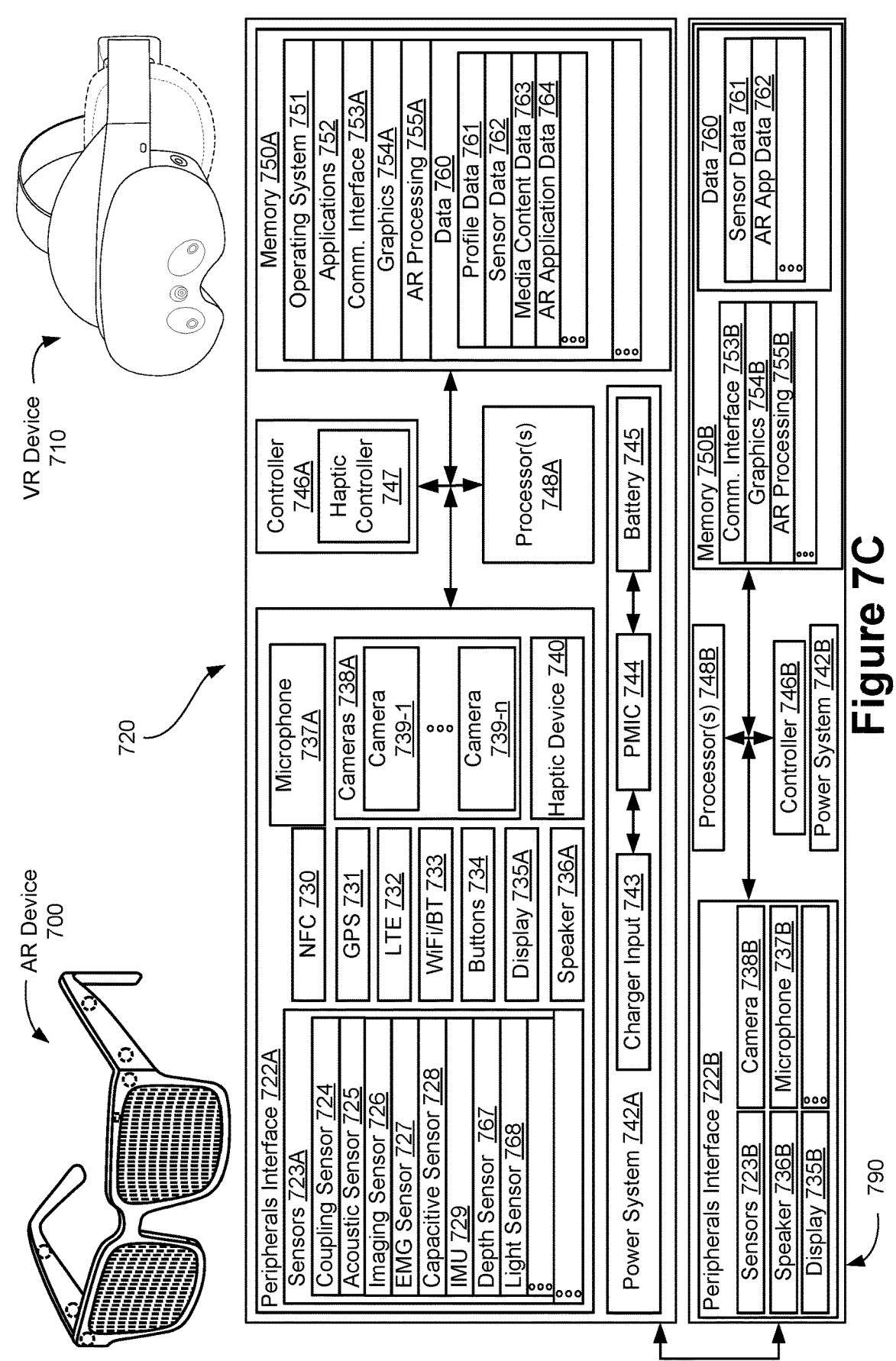

FIGS. 7A-7C show example head-wearable devices, in accordance with some embodiments. Head-wearable devices can include, but are not limited to, AR devices 710 (e.g., AR or smart eyewear devices, such as smart glasses, smart monocles, smart contacts, etc.), VR devices 710 (e.g., VR headsets, head-mounted displays (HMD)s, etc.), or other ocularly coupled devices. The AR devices 700 and the VR devices 710 can perform various functions and/or operations associated with navigating through user interfaces and selectively opening applications.

In some embodiments, an AR system (e.g., AR systems 500a-500d; FIGS. 5A-5D-2) includes an AR device 700 (as shown in FIG. 7A) and/or VR device 710 (as shown in FIGS. 7B-1-B-2). In some embodiments, the AR device 700 and the VR device 710 can include one or more analogous components (e.g., components for presenting interactive artificial-reality environments, such as processors, memory, and/or presentation devices, including one or more displays and/or one or more waveguides), some of which are described in more detail with respect to FIG. 7C. The head-wearable devices can use display projectors (e.g., display projector assemblies 707A and 707B) and/or waveguides for projecting representations of data to a user. Some embodiments of head-wearable devices do not include displays.

FIG. 7A shows an example visual depiction of the AR device 700 (e.g., which may also be described herein as augmented-reality glasses, and/or smart glasses). The AR device 700 can work in conjunction with additional electronic components that are not shown in FIGS. 7A, such as a wearable accessory device and/or an intermediary processing device, in electronic communication or otherwise configured to be used in conjunction with the AR device 700. In some embodiments, the wearable accessory device and/or the intermediary processing device may be configured to couple with the AR device 700 via a coupling mechanism in electronic communication with a coupling sensor 724, where the coupling sensor 724 can detect when an electronic device becomes physically or electronically coupled with the AR device 700. In some embodiments, the AR device 700 can be configured to couple to a housing (e.g., a portion of frame 704 or temple arms 705), which may include one or more additional coupling mechanisms configured to couple with additional accessory devices. The components shown in FIG. 7A can be implemented in hardware, software, firmware, or a combination thereof, including one or more signal-processing components and/or application-specific integrated circuits (ASICs).

The AR device 700 includes mechanical glasses components, including a frame 704 configured to hold one or more lenses (e.g., one or both lenses 706-1 and 706-2). One of ordinary skill in the art will appreciate that the AR device 700 can include additional mechanical components, such as hinges configured to allow portions of the frame 704 of the AR device 700 to be folded and unfolded, a bridge configured to span the gap between the lenses 706-1 and 706-2 and rest on the user's nose, nose pads configured to rest on the bridge of the nose and provide support for the AR device 700, earpieces configured to rest on the user's ears and provide additional support for the AR device 700, temple arms 705 configured to extend from the hinges to the earpieces of the AR device 700, and the like. One of ordinary skill in the art will further appreciate that some examples of the AR device 700 can include none of the mechanical components described herein. For example, smart contact lenses configured to present artificial-reality to users may not include any components of the AR device 700.

The lenses 706-1 and 706-2 can be individual displays or display devices (e.g., a waveguide for projected representations). The lenses 706-1 and 706-2 may act together or independently to present an image or series of images to a user. In some embodiments, the lenses 706-1 and 706-2 can operate in conjunction with one or more display projector assemblies 707A and 707B to present image data to a user. While the AR device 700 includes two displays, embodiments of this disclosure may be implemented in AR devices with a single near-eye display (NED) or more than two NEDs.

The AR device 700 includes electronic components, many of which will be described in more detail below with respect to FIG. 7C. Some example electronic components are illustrated in FIG. 7A, including sensors 723-1, 723-2, 723-3, 723-4, 723-5, and 723-6, which can be distributed along a substantial portion of the frame 704 of the AR device 700. The different types of sensors are described below in reference to FIG. 7C. The AR device 700 also includes a left camera 739A and a right camera 739B, which are located on different sides of the frame 704. And the eyewear device includes one or more processors 748A and 748B (e.g., an integral microprocessor, such as an ASIC) that is embedded into a portion of the frame 704.

FIGS. 7B-1 and 7B-2 show an example visual depiction of the VR device 710 (e.g., a head-mounted display (HMD) 712, also referred to herein as an artificial-reality headset, a head-wearable device, a VR headset, etc.). The HMD 712 includes a front body 714 and a frame 716 (e.g., a strap or band) shaped to fit around a user's head. In some embodiments, the front body 714 and/or the frame 716 includes one or more electronic elements for facilitating presentation of and/or interactions with an AR and/or VR system (e.g., displays, processors (e.g., processor 748A-1), IMUs, tracking emitter or detectors, sensors, etc.). In some embodiments, the HMD 712 includes output audio transducers (e.g., an audio transducer 718-1), as shown in FIG. 7B-2. In some embodiments, one or more components, such as the output audio transducer(s) 718 and the frame 716, can be configured to attach and detach (e.g., are detachably attachable) to the HMD 712 (e.g., a portion or all of the frame 716, and/or the output audio transducer 718), as shown in FIG. 7B-2. In some embodiments, coupling a detachable component to the HMD 712 causes the detachable component to come into electronic communication with the HMD 712. The VR device 710 includes electronic components, many of which will be described in more detail below with respect to FIG. 7C FIG. 7B-1 to 7B-2 also show that the VR device 710 one or more cameras, such as the left camera 739A and the right camera 739B, which can be analogous to the left and right cameras on the frame 704 of the AR device 700. In some embodiments, the VR device 710 includes one or more additional cameras (e.g., cameras 739C and 739D), which can be configured to augment image data obtained by the cameras 739A and 739B by providing more information. For example, the camera 739C can be used to supply color information that is not discerned by cameras 739A and 739B. In some embodiments, one or more of the cameras 739A to 739D can include an optional IR cut filter configured to remove IR light from being received at the respective camera sensors.

The VR device 710 can include a housing 790 storing one or more components of the VR device 710 and/or additional components of the VR device 710. The housing 790 can be a modular electronic device configured to couple with the VR device 710 (or an AR device 700) and supplement and/or extend the capabilities of the VR device 710 (or an AR device 700). For example, the housing 790 can include additional sensors, cameras, power sources, processors (e.g., processor 748A-2), etc. to improve and/or increase the functionality of the VR device 710. Examples of the different components included in the housing 790 are described below in reference to FIG. 7C.

Alternatively or in addition, in some embodiments, the head-wearable device, such as the VR device 710 and/or the AR device 700), includes, or is communicatively coupled to, another external device (e.g., a paired device), such as an HIPD 8 (discussed below in reference to FIGS. 8A-8B) and/or an optional neckband. The optional neckband can couple to the head-wearable device via one or more connectors (e.g., wired or wireless connectors). The head-wearable device and the neckband can operate independently without any wired or wireless connection between them. In some embodiments, the components of the head-wearable device and the neckband are located on one or more additional peripheral devices paired with the head-wearable device, the neckband, or some combination thereof. Furthermore, the neckband is intended to represent any suitable type or form of paired device. Thus, the following discussion of neckband may also apply to various other paired devices, such as smart watches, smart phones, wrist bands, other wearable devices, hand-held controllers, tablet computers, or laptop computers.

In some situations, pairing external devices, such as an intermediary processing device (e.g., an HIPD device 800, an optional neckband, and/or wearable accessory device) with the head-wearable devices (e.g., an AR device 700 and/or VR device 710) enables the head-wearable devices to achieve a similar form factor of a pair of glasses while still providing sufficient battery and computation power for expanded capabilities. Some, or all, of the battery power, computational resources, and/or additional features of the head-wearable devices can be provided by a paired device or shared between a paired device and the head-wearable devices, thus reducing the weight, heat profile, and form factor of the head-wearable devices overall while allowing the head-wearable devices to retain its desired functionality. For example, the intermediary processing device (e.g., the HIPD 800) can allow components that would otherwise be included in a head-wearable device to be included in the intermediary processing device (and/or a wearable device or accessory device), thereby shifting a weight load from the user's head and neck to one or more other portions of the user's body. In some embodiments, the intermediary processing device has a larger surface area over which to diffuse and disperse heat to the ambient environment. Thus, the intermediary processing device can allow for greater battery and computation capacity than might otherwise have been possible on the head-wearable devices, standing alone. Because weight carried in the intermediary processing device can be less invasive to a user than weight carried in the head-wearable devices, a user may tolerate wearing a lighter eyewear device and carrying or wearing the paired device for greater lengths of time than the user would tolerate wearing a heavier eyewear device standing alone, thereby enabling an artificial-reality environment to be incorporated more fully into a user's day-to-day activities.

In some embodiments, the intermediary processing device is communicatively coupled with the head-wearable device and/or to other devices. The other devices may provide certain functions (e.g., tracking, localizing, depth mapping, processing, storage, etc.) to the head-wearable device. In some embodiments, the intermediary processing device includes a controller and a power source. In some embodiments, sensors of the intermediary processing device are configured to sense additional data that can be shared with the head-wearable devices in an electronic format (analog or digital).

The controller of the intermediary processing device processes information generated by the sensors on the intermediary processing device and/or the head-wearable devices. The intermediary processing device, like an HIPD 800, can process information generated by one or more sensors of its sensors and/or information provided by other communicatively coupled devices. For example, a head-wearable device can include an IMU, and the intermediary processing device (neckband and/or an HIPD 800) can compute all inertial and spatial calculations from the IMUs located on the head-wearable device. Additional examples of processing performed by a communicatively coupled device, such as the HIPD 800, are provided below in reference to FIGS. 8A and 8B.

Artificial-reality systems may include a variety of types of visual feedback mechanisms. For example, display devices in the AR devices 700 and/or the VR devices 710 may include one or more liquid-crystal displays (LCDs), light emitting diode (LED) displays, organic LED (OLED) displays, and/or any other suitable type of display screen. Artificial-reality systems may include a single display screen for both eyes or may provide a display screen for each eye, which may allow for additional flexibility for varifocal adjustments or for correcting a refractive error associated with the user's vision. Some artificial-reality systems also include optical subsystems having one or more lenses (e.g., conventional concave or convex lenses, Fresnel lenses, or adjustable liquid lenses) through which a user may view a display screen. In addition to or instead of using display screens, some artificial-reality systems include one or more projection systems. For example, display devices in the AR device 700 and/or the VR device 710 may include micro-LED projectors that project light (e.g., using a waveguide) into display devices, such as clear combiner lenses that allow ambient light to pass through. The display devices may refract the projected light toward a user's pupil and may enable a user to simultaneously view both artificial-reality content and the real world. Artificial-reality systems may also be configured with any other suitable type or form of image projection system. As noted, some AR systems may, instead of blending an artificial reality with actual reality, substantially replace one or more of a user's sensory perceptions of the real world with a virtual experience.

While the example head-wearable devices are respectively described herein as the AR device 700 and the VR device 710, either or both of the example head-wearable devices described herein can be configured to present fully-immersive VR scenes presented in substantially all of a user's field of view, additionally or alternatively to, subtler augmented-reality scenes that are presented within a portion, less than all, of the user's field of view.

In some embodiments, the AR device 700 and/or the VR device 710 can include haptic feedback systems. The haptic feedback systems may provide various types of cutaneous feedback, including vibration, force, traction, shear, texture, and/or temperature. The haptic feedback systems may also provide various types of kinesthetic feedback, such as motion and compliance. The haptic feedback can be implemented using motors, piezoelectric actuators, fluidic systems, and/or a variety of other types of feedback mechanisms. The haptic feedback systems may be implemented independently of other artificial-reality devices, within other artificial-reality devices, and/or in conjunction with other artificial-reality devices (e.g., wrist-wearable devices which may be incorporated into headwear, gloves, body suits, handheld controllers, environmental devices (e.g., chairs or floormats), and/or any other type of device or system, such as a wrist-wearable device 600, an HIPD 800, smart textile-based garment 900, etc.), and/or other devices described herein.

FIG. 7C illustrates a computing system 720 and an optional housing 790, each of which show components that can be included in a head-wearable device (e.g., the AR device 700 and/or the VR device 710). In some embodiments, more or less components can be included in the optional housing 790 depending on practical restraints of the respective head-wearable device being described. Additionally or alternatively, the optional housing 790 can include additional components to expand and/or augment the functionality of a head-wearable device.

In some embodiments, the computing system 720 and/or the optional housing 790 can include one or more peripheral interfaces 722A and 722B, one or more power systems 742A and 742B (including charger input 743, PMIC 744, and battery 745), one or more controllers 746A 746B (including one or more haptic controllers 747), one or more processors 748A and 748B (as defined above, including any of the examples provided), and memory 750A and 750B, which can all be in electronic communication with each other. For example, the one or more processors 748A and/or 748B can be configured to execute instructions stored in the memory 750A and/or 750B, which can cause a controller of the one or more controllers 746A and/or 746B to cause operations to be performed at one or more peripheral devices of the peripherals interfaces 722A and/or 722B. In some embodiments, each operation described can occur based on electrical power provided by the power system 742A and/or 742B.

In some embodiments, the peripherals interface 722A can include one or more devices configured to be part of the computing system 720, many of which have been defined above and/or described with respect to wrist-wearable devices shown in FIGS. 6A and 6B. For example, the peripherals interface can include one or more sensors 723A. Some example sensors include: one or more coupling sensors 724, one or more acoustic sensors 725, one or more imaging sensors 726, one or more EMG sensors 727, one or more capacitive sensors 728, and/or one or more IMUs 729. In some embodiments, the sensors 723A further include depth sensors 767, light sensors 768 and/or any other types of sensors defined above or described with respect to any other embodiments discussed herein.

In some embodiments, the peripherals interface can include one or more additional peripheral devices, including one or more NFC devices 730, one or more GPS devices 731, one or more LTE devices 732, one or more WiFi and/or Bluetooth devices 733, one or more buttons 734 (e.g., including buttons that are slidable or otherwise adjustable), one or more displays 735A, one or more speakers 736A, one or more microphones 737A, one or more cameras 738A (e.g., including the a first camera 739-1 through nth camera 739-n, which are analogous to the left camera 739A and/or the right camera 739B), one or more haptic devices 740;

and/or any other types of peripheral devices defined above or described with respect to any other embodiments discussed herein.

The head-wearable devices can include a variety of types of visual feedback mechanisms (e.g., presentation devices). For example, display devices in the AR device 700 and/or the VR device 710 can include one or more liquid-crystal displays (LCDs), light emitting diode (LED) displays, organic LED (OLED) displays, micro-LEDs, and/or any other suitable types of display screens. The head-wearable devices can include a single display screen (e.g., configured to be seen by both eyes), and/or can provide separate display screens for each eye, which can allow for additional flexibility for varifocal adjustments and/or for correcting a refractive error associated with the user's vision. Some embodiments of the head-wearable devices also include optical subsystems having one or more lenses (e.g., conventional concave or convex lenses, Fresnel lenses, or adjustable liquid lenses) through which a user can view a display screen. For example, respective displays 735A can be coupled to each of the lenses 706-1 and 706-2 of the AR device 700. The displays 735A coupled to each of the lenses 706-1 and 706-2 can act together or independently to present an image or series of images to a user. In some embodiments, the AR device 700 and/or the VR device 710 includes a single display 735A (e.g., a near-eye display) or more than two displays 735A.

In some embodiments, a first set of one or more displays 735A can be used to present an augmented-reality environment, and a second set of one or more display devices 735A can be used to present a virtual-reality environment. In some embodiments, one or more waveguides are used in conjunction with presenting artificial-reality content to the user of the AR device 700 and/or the VR device 710 (e.g., as a means of delivering light from a display projector assembly and/or one or more displays 735A to the user's eyes). In some embodiments, one or more waveguides are fully or partially integrated into the AR device 700 and/or the VR device 710. Additionally, or alternatively to display screens, some artificial-reality systems include one or more projection systems. For example, display devices in the AR device 700 and/or the VR device 710 can include micro-LED projectors that project light (e.g., using a waveguide) into display devices, such as clear combiner lenses that allow ambient light to pass through. The display devices can refract the projected light toward a user's pupil and can enable a user to simultaneously view both artificial-reality content and the real world. The head-wearable devices can also be configured with any other suitable type or form of image projection system. In some embodiments, one or more waveguides are provided additionally or alternatively to the one or more display(s) 735A.

In some embodiments of the head-wearable devices, ambient light and/or a real-world live view (e.g., a live feed of the surrounding environment that a user would normally see) can be passed through a display element of a respective head-wearable device presenting aspects of the AR system. In some embodiments, ambient light and/or the real-world live view can be passed through a portion less than all, of an AR environment presented within a user's field of view (e.g., a portion of the AR environment co-located with a physical object in the user's real-world environment that is within a designated boundary (e.g., a guardian boundary) configured to be used by the user while they are interacting with the AR environment). For example, a visual user interface element (e.g., a notification user interface element) can be presented at the head-wearable devices, and an amount of ambient light and/or the real-world live view (e.g., 15-50% of the ambient light and/or the real-world live view) can be passed through the user interface element, such that the user can distinguish at least a portion of the physical environment over which the user interface element is being displayed.

The head-wearable devices can include one or more external displays 735A for presenting information to users. For example, an external display 735A can be used to show a current battery level, network activity (e.g., connected, disconnected, etc.), current activity (e.g., playing a game, in a call, in a meeting, watching a movie, etc.), and/or other relevant information. In some embodiments, the external displays 735A can be used to communicate with others. For example, a user of the head-wearable device can cause the external displays 735A to present a do not disturb notification. The external displays 735A can also be used by the user to share any information captured by the one or more components of the peripherals interface 722A and/or generated by head-wearable device (e.g., during operation and/or performance of one or more applications).

The memory 750A can include instructions and/or data executable by one or more processors 748A (and/or processors 748B of the housing 790) and/or a memory controller of the one or more controllers 746A (and/or controller 746B of the housing 790). The memory 750A can include one or more operating systems 751; one or more applications 752; one or more communication interface modules 753A; one or more graphics modules 754A; one or more AR processing modules 755A; and/or any other types of modules or components defined above or described with respect to any other embodiments discussed herein.

The data 760 stored in memory 750A can be used in conjunction with one or more of the applications and/or programs discussed above. The data 760 can include profile data 761; sensor data 762; media content data 763; AR application data 764; and/or any other types of data defined above or described with respect to any other embodiments discussed herein.

In some embodiments, the controller 746A of the head-wearable devices processes information generated by the sensors 723A on the head-wearable devices and/or another component of the head-wearable devices and/or communicatively coupled with the head-wearable devices (e.g., components of the housing 790, such as components of peripherals interface 722B). For example, the controller 746A can process information from the acoustic sensors 725 and/or image sensors 726. For each detected sound, the controller 746A can perform a direction of arrival (DOA) estimation to estimate a direction from which the detected sound arrived at a head-wearable device. As one or more of the acoustic sensors 725 detects sounds, the controller 746A can populate an audio data set with the information (e.g., represented by sensor data 762).

In some embodiments, a physical electronic connector can convey information between the head-wearable devices and another electronic device, and/or between one or more processors 748A of the head-wearable devices and the controller 746A. The information can be in the form of optical data, electrical data, wireless data, or any other transmittable data form. Moving the processing of information generated by the head-wearable devices to an intermediary processing device can reduce weight and heat in the eyewear device, making it more comfortable and safer for a user. In some embodiments, an optional accessory device (e.g., an electronic neckband or an HIPD 800) is coupled to the head-wearable devices via one or more connectors. The connectors can be wired or wireless connectors and can include electrical and/or non-electrical (e.g., structural) components. In some embodiments, the head-wearable devices and the accessory device can operate independently without any wired or wireless connection between them.

The head-wearable devices can include various types of computer vision components and subsystems. For example, the AR device 700 and/or the VR device 710 can include one or more optical sensors such as two-dimensional (2D) or three-dimensional (3D) cameras, time-of-flight depth sensors, single-beam or sweeping laser rangefinders, 3D LiDAR sensors, and/or any other suitable type or form of optical sensor. A head-wearable device can process data from one or more of these sensors to identify a location of a user and/or aspects of the use's real-world physical surroundings, including the locations of real-world objects within the real-world physical surroundings. In some embodiments, the methods described herein are used to map the real world, to provide a user with context about real-world surroundings, and/or to generate interactable virtual objects (which can be replicas or digital twins of real-world objects that can be interacted with in AR environment), among a variety of other functions. For example, FIGS. 7B-1 and 7B-2 show the VR device 710 having cameras 739A-739D, which can be used to provide depth information for creating a voxel field and a two-dimensional mesh to provide object information to the user to avoid collisions.

The optional housing 790 can include analogous components to those describe above with respect to the computing system 720. For example, the optional housing 790 can include a respective peripherals interface 722B including more or less components to those described above with respect to the peripherals interface 722A. As described above, the components of the optional housing 790 can be used augment and/or expand on the functionality of the head-wearable devices. For example, the optional housing 790 can include respective sensors 723B, speakers 736B, displays 735B, microphones 737B, cameras 738B, and/or other components to capture and/or present data. Similarly, the optional housing 790 can include one or more processors 748B, controllers 746B, and/or memory 750B (including respective communication interface modules 753B; one or more graphics modules 754B; one or more AR processing modules 755B, etc.) that can be used individually and/or in conjunction with the components of the computing system 720.

The techniques described above in FIGS. 7A-7C can be used with different head-wearable devices. In some embodiments, the head-wearable devices (e.g., the AR device 700 and/or the VR device 710) can be used in conjunction with one or more wearable device such as a wrist-wearable device 600 (or components thereof) and/or a smart textile-based garment 900 (FIGS. 9A-9C), as well as an HIPD 800. Having thus described example the head-wearable devices, attention will now be turned to example handheld intermediary processing devices, such as HIPD 800.

Example Handheld Intermediary Processing Devices

FIGS. 8A and 8B illustrate an example handheld intermediary processing device (HIPD) 800, in accordance with some embodiments. The HIPD 800 can perform various functions and/or operations associated with navigating through user interfaces and selectively opening applications.

FIG. 8A shows a top view 805 and a side view 825 of the HIPD 800. The HIPD 800 is configured to communicatively couple with one or more wearable devices (or other electronic devices) associated with a user. For example, the HIPD 800 is configured to communicatively couple with a user's wrist-wearable device 600 (or components thereof, such as the watch body 620 and the wearable band 610), AR device 700, and/or VR device 710. The HIPD 800 can be configured to be held by a user (e.g., as a handheld controller), carried on the user's person (e.g., in their pocket, in their bag, etc.), placed in proximity of the user (e.g., placed on their desk while seated at their desk, on a charging dock, etc.), and/or placed at or within a predetermined distance from a wearable device or other electronic device (e.g., where, in some embodiments, the predetermined distance is the maximum distance (e.g., 10 meters) at which the HIPD 800 can successfully be communicatively coupled with an electronic device, such as a wearable device).

The HIPD 800 can perform various functions independently and/or in conjunction with one or more wearable devices (e.g., wrist-wearable device 600, AR device 700, VR device 710, etc.). The HIPD 800 is configured to increase and/or improve the functionality of communicatively coupled devices, such as the wearable devices. The HIPD 800 is configured to perform one or more functions or operations associated with interacting with user interfaces and applications of communicatively coupled devices, interacting with an AR environment, interacting with VR environment, and/or operating as a human-machine interface controller. Additionally, as will be described in more detail below, functionality and/or operations of the HIPD 800 can include, without limitation, task offloading and/or handoffs; thermals offloading and/or handoffs; 6 degrees of freedom (6DoF) raycasting and/or gaming (e.g., using imaging devices or cameras 814A and 814B, which can be used for simultaneous localization and mapping (SLAM) and/or with other image processing techniques); portable charging; messaging; image capturing via one or more imaging devices or cameras (e.g., cameras 822A and 822B); sensing user input (e.g., sensing a touch on a multi-touch input surface 802); wireless communications and/or interlining (e.g., cellular, near field, Wi-Fi, personal area network, etc.); location determination; financial transactions; providing haptic feedback; alarms; notifications; biometric authentication; health monitoring; sleep monitoring; etc. The above-example functions can be executed independently in the HIPD 800 and/or in communication between the HIPD 800 and another wearable device described herein. In some embodiments, functions can be executed on the HIPD 800 in conjunction with an AR environment. As the skilled artisan will appreciate upon reading the descriptions provided herein, the novel the HIPD 800 described herein can be used with any type of suitable AR environment.

While the HIPD 800 is communicatively coupled with a wearable device and/or other electronic device, the HIPD 800 is configured to perform one or more operations initiated at the wearable device and/or the other electronic device. In particular, one or more operations of the wearable device and/or the other electronic device can be offloaded to the HIPD 800 to be performed. The HIPD 800 performs the one or more operations of the wearable device and/or the other electronic device and provides to data corresponded to the completed operations to the wearable device and/or the other electronic device. For example, a user can initiate a video stream using AR device 700 and back-end tasks associated with performing the video stream (e.g., video rendering) can be offloaded to the HIPD 800, which the HIPD 800 performs and provides corresponding data to the AR device 700 to perform remaining front-end tasks associated with the video stream (e.g., presenting the rendered video data via a display of the AR device 700). In this way, the HIPD 800, which has more computational resources and greater thermal headroom than a wearable device, can perform computationally intensive tasks for the wearable device improving performance of an operation performed by the wearable device.

The HIPD 800 includes a multi-touch input surface 802 on a first side (e.g., a front surface) that is configured to detect one or more user inputs. In particular, the multi-touch input surface 802 can detect single tap inputs, multi-tap inputs, swipe gestures and/or inputs, force-based and/or pressure-based touch inputs, held taps, and the like. The multi-touch input surface 802 is configured to detect capacitive touch inputs and/or force (and/or pressure) touch inputs. The multi-touch input surface 802 includes a first touch-input surface 804 defined by a surface depression, and a second touch-input surface 806 defined by a substantially planar portion. The first touch-input surface 804 can be disposed adjacent to the second touch-input surface 806. In some embodiments, the first touch-input surface 804 and the second touch-input surface 806 can be different dimensions, shapes, and/or cover different portions of the multi-touch input surface 802. For example, the first touch-input surface 804 can be substantially circular and the second touch-input surface 806 is substantially rectangular. In some embodiments, the surface depression of the multi-touch input surface 802 is configured to guide user handling of the HIPD 800. In particular, the surface depression is configured such that the user holds the HIPD 800 upright when held in a single hand (e.g., such that the using imaging devices or cameras 814A and 814B are pointed toward a ceiling or the sky). Additionally, the surface depression is configured such that the user's thumb rests within the first touch-input surface 804.

In some embodiments, the different touch-input surfaces include a plurality of touch-input zones. For example, the second touch-input surface 806 includes at least a first touch-input zone 808 within a second touch-input zone 806 and a third touch-input zone 810 within the first touch-input zone 808. In some embodiments, one or more of the touch-input zones are optional and/or user defined (e.g., a user can specific a touch-input zone based on their preferences). In some embodiments, each touch-input surface and/or touch-input zone is associated with a predetermined set of commands. For example, a user input detected within the first touch-input zone 808 causes the HIPD 800 to perform a first command and a user input detected within the second touch-input zone 806 causes the HIPD 800 to perform a second command, distinct from the first. In some embodiments, different touch-input surfaces and/or touch-input zones are configured to detect one or more types of user inputs. The different touch-input surfaces and/or touch-input zones can be configured to detect the same or distinct types of user inputs. For example, the first touch-input zone 808 can be configured to detect force touch inputs (e.g., a magnitude at which the user presses down) and capacitive touch inputs, and the second touch-input zone 806 can be configured to detect capacitive touch inputs.

The HIPD 800 includes one or more sensors 851 for sensing data used in the performance of one or more operations and/or functions. For example, the HIPD 800 can include an IMU that is used in conjunction with cameras 814 for 3-dimensional object manipulation (e.g., enlarging, moving, destroying, etc. an object) in an AR or VR environment. Non-limiting examples of the sensors 851 included in the HIPD 800 include a light sensor, a magnetometer, a depth sensor, a pressure sensor, and a force sensor. Additional examples of the sensors 851 are provided below in reference to FIG. 8B.

The HIPD 800 can include one or more light indicators 812 to provide one or more notifications to the user. In some embodiments, the light indicators are LEDs or other types of illumination devices. The light indicators 812 can operate as a privacy light to notify the user and/or others near the user that an imaging device and/or microphone are active. In some embodiments, a light indicator is positioned adjacent to one or more touch-input surfaces. For example, a light indicator can be positioned around the first touch-input surface 804. The light indicators can be illuminated in different colors and/or patterns to provide the user with one or more notifications and/or information about the device. For example, a light indicator positioned around the first touch-input surface 804 can flash when the user receives a notification (e.g., a message), change red when the HIPD 800 is out of power, operate as a progress bar (e.g., a light ring that is closed when a task is completed (e.g., 0% to 100%)), operates as a volume indicator, etc.).

In some embodiments, the HIPD 800 includes one or more additional sensors on another surface. For example, as shown FIG. 8A, HIPD 800 includes a set of one or more sensors (e.g., sensor set 820) on an edge of the HIPD 800. The sensor set 820, when positioned on an edge of the of the HIPD 800, can be pre positioned at a predetermined tilt angle (e.g., 26 degrees), which allows the sensor set 820 to be angled toward the user when placed on a desk or other flat surface. Alternatively, in some embodiments, the sensor set 820 is positioned on a surface opposite the multi-touch input surface 802 (e.g., a back surface). The one or more sensors of the sensor set 820 are discussed in detail below.

The side view 825 of the of the HIPD 800 shows the sensor set 820 and camera 814B. The sensor set 820 includes one or more cameras 822A and 822B, a depth projector 824, an ambient light sensor 828, and a depth receiver 830. In some embodiments, the sensor set 820 includes a light indicator 826. The light indicator 826 can operate as a privacy indicator to let the user and/or those around them know that a camera and/or microphone is active. The sensor set 820 is configured to capture a user's facial expression such that the user can puppet a custom avatar (e.g., showing emotions, such as smiles, laughter, etc., on the avatar or a digital representation of the user). The sensor set 820 can be configured as a side stereo RGB system, a rear indirect Time-of-Flight (iToF) system, or a rear stereo RGB system. As the skilled artisan will appreciate upon reading the descriptions provided herein, the novel HIPD 800 described herein can use different sensor set 820 configurations and/or sensor set 820 placement.

In some embodiments, the HIPD 800 includes one or more haptic devices 871 (FIG. 8B; e.g., a vibratory haptic actuator) that are configured to provide haptic feedback (e.g., kinesthetic sensation). The sensors 851, and/or the haptic devices 871 can be configured to operate in conjunction with multiple applications and/or communicatively coupled devices including, without limitation, a wearable devices, health monitoring applications, social media applications, game applications, and artificial reality applications (e.g., the applications associated with artificial reality).

The HIPD 800 is configured to operate without a display. However, in optional embodiments, the HIPD 800 can include a display 868 (FIG. 8B). The HIPD 800 can also income one or more optional peripheral buttons 867 (FIG. 8B). For example, the peripheral buttons 867 can be used to turn on or turn off the HIPD 800. Further, the HIPD 800 housing can be formed of polymers and/or elastomer elastomers. The HIPD 800 can be configured to have a non-slip surface to allow the HIPD 800 to be placed on a surface without requiring a user to watch over the HIPD 800. In other words, the HIPD 800 is designed such that it would not easily slide off a surfaces. In some embodiments, the HIPD 800 include one or magnets to couple the HIPD 800 to another surface. This allows the user to mount the HIPD 800 to different surfaces and provide the user with greater flexibility in use of the HIPD 800.

As described above, the HIPD 800 can distribute and/or provide instructions for performing the one or more tasks at the HIPD 800 and/or a communicatively coupled device. For example, the HIPD 800 can identify one or more back-end tasks to be performed by the HIPD 800 and one or more front-end tasks to be performed by a communicatively coupled device. While the HIPD 800 is configured to offload and/or handoff tasks of a communicatively coupled device, the HIPD 800 can perform both back-end and front-end tasks (e.g., via one or more processors, such as CPU 877; FIG. 8B). The HIPD 800 can, without limitation, can be used to perform augmenting calling (e.g., receiving and/or sending 3D or 2.5D live volumetric calls, live digital human representation calls, and/or avatar calls), discreet messaging, 6DoF portrait/landscape gaming, AR/VR object manipulation, AR/VR content display (e.g., presenting content via a virtual display), and/or other AR/VR interactions. The HIPD 800 can perform the above operations alone or in conjunction with a wearable device (or other communicatively coupled electronic device).

FIG. 8B shows block diagrams of a computing system 840 of the HIPD 800, in accordance with some embodiments. The HIPD 800, described in detail above, can include one or more components shown in HIPD computing system 840. The HIPD 800 will be understood to include the components shown and described below for the HIPD computing system 840. In some embodiments, all, or a substantial portion of the components of the HIPD computing system 840 are included in a single integrated circuit. Alternatively, in some embodiments, components of the HIPD computing system 840 are included in a plurality of integrated circuits that are communicatively coupled.

The HIPD computing system 840 can include a processor (e.g., a CPU 877, a GPU, and/or a CPU with integrated graphics), a controller 875, a peripherals interface 850 that includes one or more sensors 851 and other peripheral devices, a power source (e.g., a power system 895), and memory (e.g., a memory 878) that includes an operating system (e.g., an operating system 879), data (e.g., data 888), one or more applications (e.g., applications 880), and one or more modules (e.g., a communications interface module 881, a graphics module 882, a task and processing management module 883, an interoperability module 884, an AR processing module 885, a data management module 886, etc.). The HIPD computing system 840 further includes a power system 895 that includes a charger input and output 896, a PMIC 897, and a battery 898, all of which are defined above.

In some embodiments, the peripherals interface 850 can include one or more sensors 851. The sensors 851 can include analogous sensors to those described above in reference to FIG. 6B. For example, the sensors 851 can include imaging sensors 854, (optional) EMG sensors 856, IMUs 858, and capacitive sensors 860. In some embodiments, the sensors 851 can include one or more pressure sensor 852 for sensing pressure data, an altimeter 853 for sensing an altitude of the HIPD 800, a magnetometer 855 for sensing a magnetic field, a depth sensor 857 (or a time-of-flight sensor) for determining a difference between the camera and the subject of an image, a position sensor 859

(e.g., a flexible position sensor) for sensing a relative displacement or position change of a portion of the HIPD 800, a force sensor 861 for sensing a force applied to a portion of the HIPD 800, and a light sensor 862 (e.g., an ambient light sensor) for detecting an amount of lighting. The sensors 851 can include one or more sensors not shown in FIG. 8B.

Analogous to the peripherals described above in reference to FIGS. 6B, the peripherals interface 850 can also include an NFC component 863, a GPS component 864, an LTE component 865, a Wi-Fi and/or Bluetooth communication component 866, a speaker 869, a haptic device 871, and a microphone 873. As described above in reference to FIG. 8A, the HIPD 800 can optionally include a display 868 and/or one or more buttons 867. The peripherals interface 850 can further include one or more cameras 870, touch surfaces 872, and/or one or more light emitters 874. The multi-touch input surface 802 described above in reference to FIG. 8A is an example of touch surface 872. The light emitters 874 can be one or more LEDs, lasers, etc. and can be used to project or present information to a user. For example, the light emitters 874 can include light indicators 812 and 826 described above in reference to FIG. 8A. The cameras 870 (e.g., cameras 814A, 814B, and 822 described above in FIG. 8A) can include one or more wide angle cameras, fish-eye cameras, spherical cameras, compound eye cameras (e.g., stereo and multi cameras), depth cameras, RGB cameras, ToF cameras, RGB-D cameras (depth and ToF cameras), and/or other available cameras. Cameras 870 can be used for SLAM; 6 DoF ray casting, gaming, object manipulation, and/or other rendering; facial recognition and facial expression recognition, etc.

Similar to the watch body computing system 660 and the watch band computing system 630 described above in reference to FIG. 6B, the HIPD computing system 840 can include one or more haptic controllers 876 and associated componentry (e.g., haptic devices 871) for providing haptic events at the HIPD 800.

Memory 878 can include high-speed random-access memory and/or non-volatile memory, such as one or more magnetic disk storage devices, flash memory devices, or other non-volatile solid-state memory devices. Access to the memory 878 by other components of the HIPD 800, such as the one or more processors and the peripherals interface 850, can be controlled by a memory controller of the controllers 875.

In some embodiments, software components stored in the memory 878 include one or more operating systems 879, one or more applications 880, one or more communication interface modules 881, one or more graphics modules 882, one or more data management modules 885, which are analogous to the software components described above in reference to FIG. 6B.

In some embodiments, software components stored in the memory 878 include a task and processing management module 883 for identifying one or more front-end and back-end tasks associated with an operation performed by the user, performing one or more front-end and/or back-end tasks, and/or providing instructions to one or more communicatively coupled devices that cause performance of the one or more front-end and/or back-end tasks. In some embodiments, the task and processing management module 883 uses data 888 (e.g., device data 890) to distribute the one or more front-end and/or back-end tasks based on communicatively coupled devices' computing resources, available power, thermal headroom, ongoing operations, and/or other factors. For example, the task and processing management module 883 can cause the performance of one or more back-end tasks (of an operation performed at communicatively coupled AR device 700) at the HIPD 800 in accordance with a determination that the operation is utilizing a predetermined amount (e.g., at least 70%) of computing resources available at the AR device 700.

In some embodiments, software components stored in the memory 878 include an interoperability module 884 for exchanging and utilizing information received and/or provided to distinct communicatively coupled devices. The interoperability module 884 allows for different systems, devices, and/or applications to connect and communicate in a coordinated way without user input. In some embodiments, software components stored in the memory 878 include an AR module 885 that is configured to process signals based at least on sensor data for use in an AR and/or VR environment. For example, the AR processing module 885 can be used for 3D object manipulation, gesture recognition, facial and facial expression, recognition, etc.

The memory 878 can also include data 887, including structured data. In some embodiments, the data 887 can include profile data 889, device data 889 (including device data of one or more devices communicatively coupled with the HIPD 800, such as device type, hardware, software, configurations, etc.), sensor data 891, media content data 892, and application data 893.

It should be appreciated that the HIPD computing system 840 is an example of a computing system within the HIPD 800, and that the HIPD 800 can have more or fewer components than shown in the HIPD computing system 840, combine two or more components, and/or have a different configuration and/or arrangement of the components. The various components shown in HIPD computing system 840 are implemented in hardware, software, firmware, or a combination thereof, including one or more signal processing and/or application-specific integrated circuits.

Figure 9C:
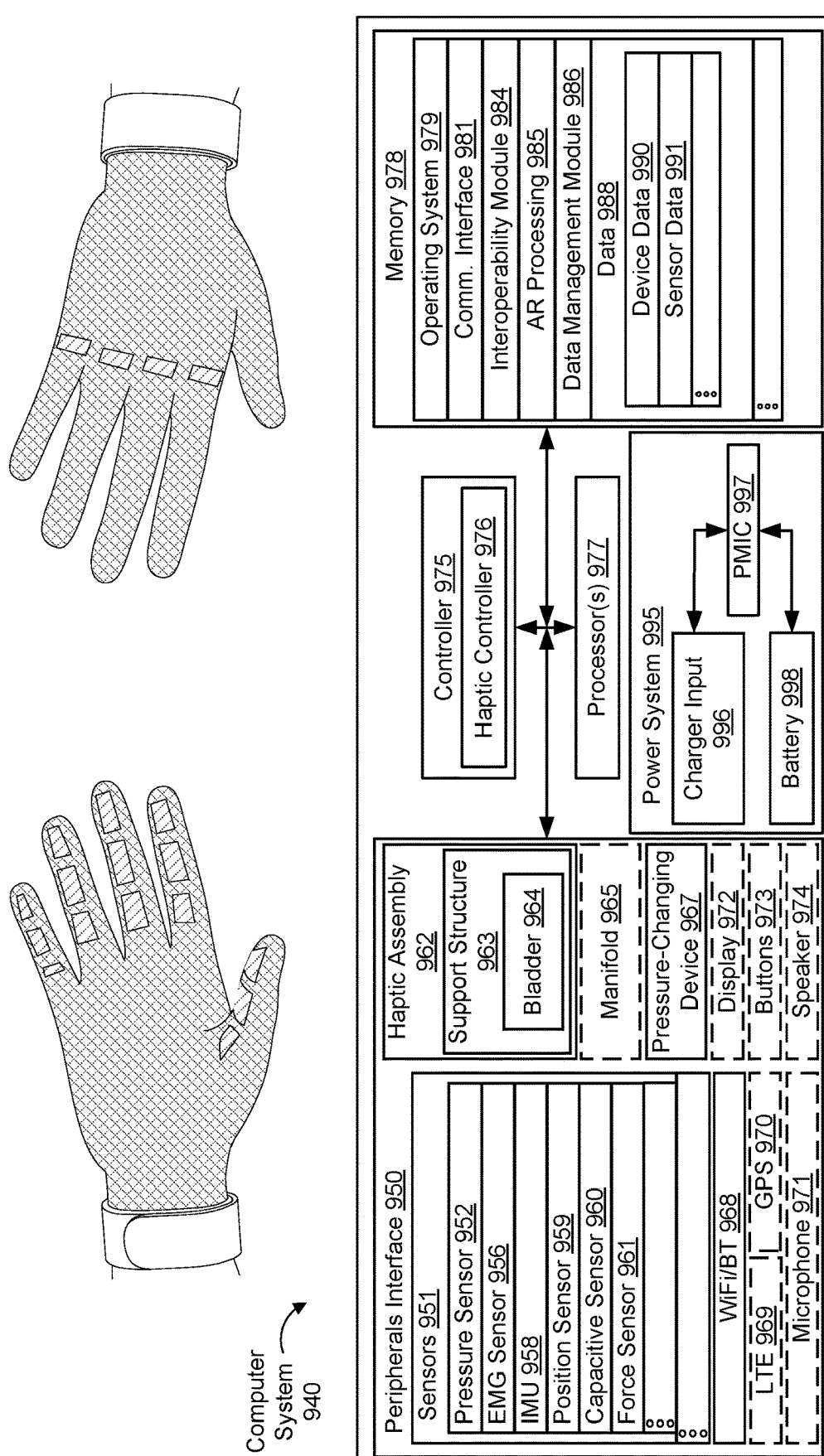

The techniques described above in FIG. 8A-8B can be used with any device used as a human-machine interface controller. In some embodiments, an HIPD 800 can be used in conjunction with one or more wearable device such as a head-wearable device (e.g., AR device 700 and VR device 710) and/or a wrist-wearable device 600 (or components thereof). In some embodiments, an HIPD 800 can also be used in conjunction with a wearable garment, such as smart textile-based garment 900 (FIGS. 9A-9C). Having thus described example HIPD 800, attention will now be turned to example feedback devices, such as smart textile-based garment 900.

Example Smart Textile-Based Garments

FIGS. 9A and 9B illustrate an example smart textile-based garment, in accordance with some embodiments. The smart textile-based garment 900 (e.g., wearable gloves, a shirt, a headband, a wristbands, socks, etc.) is configured to communicatively couple with one or more electronic devices, such as a wrist-wearable device 600, a head-wearable device, an HIPD 800, a laptop, tablet, and/or other computing devices. The smart textile-based garment 900 can perform various functions and/or operations associated with navigating through user interfaces and selectively opening applications.

The smart textile-based garment 900 can be part of an AR system, such as AR system 500d described above in reference to FIGS. 5D-1 and 5D-2. The smart textile-based garment 900 is also configured to provide feedback (e.g., tactile or other haptic feedback) to a user based on the user's interactions with a computing system (e.g., navigation of a user interface, operation of an application (e.g., game vibrations, media responsive haptics), device notifications, etc.)), and/or the user's interactions within an AR environment. In some embodiments, the smart textile-based garment 900 receives instructions from a communicatively coupled device (e.g., the wrist-wearable device 600, a head-wearable device, and HIPD 800, etc.) for causing the performance of a feedback response. Alternatively, or in addition, in some embodiments, the smart textile-based garment 900 determines one or more feedback responses to provide a user. The smart textile-based garment 900 can determine the one or more feedback responses based on sensor data captured by one or more of its sensors (e.g., sensors 951; FIG. 9C) or communicatively coupled sensors (e.g., sensors of a wrist-wearable device 600, a head-wearable device, an HIPD 800, and/or other computing device).

Non-limiting examples of the feedback determined by the smart textile-based garment 900 and/or a communicatively coupled device include visual feedback, audio feedback, haptic (e.g., tactile, kinesthetic, etc.) feedback, thermal or temperature feedback, and/or other sensory perceptible feedback. The smart textile-based garment 900 can include respective feedback devices (e.g., a haptic device or assembly 962 or other feedback devices or assemblies) to provide the feedback responses to the user. Similarly, the smart textile-based garment 900 can communicatively couple with another device (and/or the other device's feedback devices) to coordinate the feedback provided to the user. For example, a VR device 710 can present an AR environment to a user and as the user interacts with objects within the AR environment, such as a virtual cup, the smart textile-based garment 900 provides respective response to the user. In particular, the smart textile-based garment 900 can provide haptic feedback to prevent (or, at a minimum, hinder/resist movement of) one or more of the user's fingers from bending past a certain point to simulate the sensation of touching a solid cup and/or thermal feedback to simulate the sensation of a cold or warm beverage.

Additionally or alternatively, in some embodiments, the smart textile-based garment 900 is configured to operate as a controller configured to perform one or more functions or operations associated with interacting with user interfaces and applications of communicatively coupled devices, interacting with an AR environment, interacting with VR environment, and/or operating as a human-machine interface controller.

FIG. 9A shows one or more haptic assemblies 962 (e.g., first through fourth haptic assemblies 962-1 through 962-4) on a portion of the smart textile-based garment 900 adjacent to a palmar side of the user's hand and FIG. 9B shows additional haptic assemblies (e.g., a fifth haptic assembly 962-5) on a portion of the smart textile-based garment 900 adjacent to a dorsal side of the user's hand. In some embodiments, the haptic assemblies 962 include a mechanism that, at a minimum, provide resistance when a respective haptic assembly 962 is transitioned from a first state (e.g., a first pressurized state (e.g., at atmospheric pressure or deflated)) to a second state (e.g., a second pressurized state (e.g., inflated to a threshold pressure)). In other words, the haptic assemblies 962 described can transition between a first pressurized state and a second pressurized state to provide haptic feedback to the user. Structures of haptic assemblies 962 can be integrated into various devices configured to be in contact or proximity to a user's skin, including, but not limited to devices such as glove worn devices, body worn clothing device, headset devices. Each of the haptic assemblies 962 can be included in or physically coupled to a garment component 904 of the smart textile-based garment 900. For example, each of the haptic assemblies 962-1, 962-2, 962-3, ... 962-N are physically coupled to the garment 904 are configured to contact respective phalanges of a user's thumb and fingers.

Due to the ever-changing nature of artificial-reality, the haptic assemblies 962 may be required to transition between the multiple states hundreds, or perhaps thousands of times, during a single use. Thus, the haptic assemblies 962 described herein are durable and designed to quickly transition from state to state. To provide some context, in a first pressurized state, the haptic assemblies 962 do not impede free movement of a portion of the wearer's body. For example, one or more haptic assemblies 962 incorporated into a glove are made from flexible materials that do not impede free movement of the wearer's hand and fingers (e.g., an electrostatic-zipping actuator). The haptic assemblies 962 are configured to conform to a shape of the portion of the wearer's body when in the first pressurized state. However, once in a second pressurized state, the haptic assemblies 962 can be configured to restrict and/or impede free movement of the portion of the wearer's body (e.g., appendages of the user's hand). For example, the respective haptic assembly 962 (or multiple respective haptic assemblies) can restrict movement of a wearer's finger (e.g., prevent the finger from curling or extending) when the haptic assembly 962 is in the second pressurized state. Moreover, once in the second pressurized state, the haptic assemblies 962 may take different shapes, with some haptic assemblies 962 configured to take a planar, rigid shape (e.g., flat and rigid), while some other haptic assemblies 962 are configured to curve or bend, at least partially.

The smart textile-based garment 900 can be one of a plurality of devices in an AR system (e.g., AR systems of FIGS. 5A-5D-2). For example, a user can wear a pair of gloves (e.g., a first type of smart textile-based garment 900), wear a haptics component of a wrist-wearable device 600 (FIGS. 6A-6B), wear a headband (e.g., a second type of smart textile-based garment 900), hold an HIPD 800, etc. As explained above, the haptic assemblies 962 are configured to provide haptic simulations to a wearer of the smart textile-based garments 900. The garment 904 of each smart textile-based garment 900 can be one of various articles of clothing (e.g., gloves, socks, shirts, pants, etc.). Thus, a user may wear multiple smart textile-based garments 900 that are each configured to provide haptic stimulations to respective parts of the body where the smart textile-based garments 900 are being worn. Although the smart textile-based garment 900 are described as an individual device, in some embodiments, the smart textile-based garment 900 can be combined with other wearable devices described herein. For example, the smart textile-based garment 900 can form part of a VR device 710 (e.g., a headband portion).

FIG. 9C shows block diagrams of a computing system 940 of the haptic assemblies 962, in accordance with some embodiments. The computing system 940 can include one or more peripheral interfaces 950, one or more power systems 995 (including charger input 996, PMIC 997, and battery 998), one or more controllers 975 (including one or more haptic controllers 976), one or more processors 977 (as defined above, including any of the examples provided), and memory 978, which can all be in electronic communication with each other. For example, the one or more processors 977 can be configured to execute instructions stored in the memory 978, which can cause a controller of the one or more controllers 975 to cause operations to be performed at one or more peripheral devices of the peripherals interface 950. In some embodiments, each operation described can occur based on electrical power provided by the power system 995.

In some embodiments, the peripherals interface 950 can include one or more devices configured to be part of the computing system 940, many of which have been defined above and/or described with respect to wrist-wearable devices shown in FIGS. 6A-8B. For example, the peripherals interface 950 can include one or more sensors 951, such as one or more pressure sensors 952, one or more EMG sensors 956, one or more IMUs 958, one or more position sensors 959, one or more capacitive sensors 960, one or more force sensors 961; and/or any other types of sensors defined above or described with respect to any other embodiments discussed herein. In some embodiments, the peripherals interface can include one or more additional peripheral devices including one or more WiFi and/or Bluetooth devices 968; an LTE component 969; a GPS component 970; a microphone 971; one or more haptic assemblies 962; one or more support structures 963 (which can include one or more bladders 964; one or more manifolds 965; one or more pressure-changing devices 967; one or more displays 972; one or more buttons 973; one or more speakers 974; and/or any other types of peripheral devices defined above or described with respect to any other embodiments discussed herein. In some embodiments, computing system 940 includes more or less components that those shown in FIG. 9C.

In some embodiments, each haptic assembly 962 includes a support structure 963, and at least one bladder 964. The bladder 964 (e.g., a membrane) is a sealed, inflatable pocket made from a durable and puncture resistance material, such as thermoplastic polyurethane (TPU), a flexible polymer, or the like. The bladder 964 contains a medium (e.g., a fluid such as air, inert gas, or even a liquid) that can be added to or removed from the bladder 964 to change a pressure (e.g., fluid pressure) inside the bladder 964. The support structure 963 is made from a material that is stronger and stiffer than the material of the bladder 964. A respective support structure 963 coupled to a respective bladder 964 is configured to reinforce the respective bladder 964 as the respective bladder changes shape and size due to changes in pressure (e.g., fluid pressure) inside the bladder. The above example haptic assembly 962 is non-limiting. The haptic assembly 962 can include eccentric rotating mass (ERM), linear resonant actuators (LRA), voice coil motor (VCM), piezo haptic actuator, thermoelectric devices, solenoid actuators, ultrasonic transducers, thermo-resistive heaters, Peltier devices, and/or other devices configured to generate a perceptible response.

The smart textile-based garment 900 also includes a haptic controller 976 and a pressure-changing device 967. Alternatively, in some embodiments, the computing system 940 is communicatively coupled with a haptic controller 976 and/or pressure-changing device 967 (e.g., in electronic communication with one or more processors 977 of the computing system 940). The haptic controller 976 is configured to control operation of the pressure-changing device 967, and in turn operation of the smart textile-based garments 900. For example, the haptic controller 976 sends one or more signals to the pressure-changing device 967 to activate the pressure-changing device 967 (e.g., turn it on and off). The one or more signals can specify a desired pressure (e.g., pounds-per-square inch) to be output by the pressure-changing device 967. Generation of the one or more signals, and in turn the pressure output by the pressure-changing device 967, can be based on information collected by sensors 951 of the smart textile-based garment 900 and/or other communicatively coupled device. For example, the haptic controller 976 can provide one or more signals, based on collected sensor data, to cause the pressure-changing device 967 to increase the pressure (e.g., fluid pressure) inside a first haptic assembly 962 at a first time, and provide one or more additional signals, based on additional sensor data, to the pressure-changing device 967 to cause the pressure-changing device 967 to further increase the pressure inside a second haptic assembly 962 at a second time after the first time. Further, the haptic controller 976 can provide one or more signals to cause the pressure-changing device 967 to inflate one or more bladders 964 in a first portion of a smart textile-based garment 900 (e.g., a first finger), while one or more bladders 964 in a second portion of the smart textile-based garment 900 (e.g., a second finger) remain unchanged. Additionally, the haptic controller 976 can provide one or more signals to cause the pressure-changing device 967 to inflate one or more bladders 964 in a first smart textile-based garment 900 to a first pressure and inflate one or more other bladders 964 in the first smart textile-based garment 900 to a second pressure different from the first pressure. Depending on the number of smart textile-based garments 900 serviced by the pressure-changing device 967, and the number of bladders therein, many different inflation configurations can be achieved through the one or more signals and the examples above are not meant to be limiting.

The smart textile-based garment 900 may include an optional manifold 965 between the pressure-changing device 967, the haptic assemblies 962, and/or other portions of the smart textile-based garment 900. The manifold 965 may include one or more valves (not shown) that pneumatically couple each of the haptic assemblies 962 with the pressure-changing device 967 via tubing. In some embodiments, the manifold 965 is in communication with the controller 975, and the controller 975 controls the one or more valves of the manifold 965 (e.g., the controller generates one or more control signals). The manifold 965 is configured to switchably couple the pressure-changing device 967 with one or more haptic assemblies 962 of the smart textile-based garment 900. In some embodiments, one or more smart textile-based garment 900 or other haptic devices can be coupled in a network of haptic device and the manifold 965 can distribute the fluid between the coupled smart textile-based garments 900.

In some embodiments, instead of using the manifold 965 to pneumatically couple the pressure-changing device 967 with the haptic assemblies 962, the smart textile-based garment 900 may include multiple pressure-changing devices 967, where each pressure-changing device 967 is pneumatically coupled directly with a single (or multiple) haptic assembly 962. In some embodiments, the pressure-changing device 967 and the optional manifold 965 can be configured as part of one or more of the smart textile-based garments 900 (not illustrated) while, in other embodiments, the pressure-changing device 967 and the optional manifold 965 can be configured as external to the smart textile-based garments 900. In some embodiments, a single pressure-changing device 967 can be shared by multiple smart textile-based garment 900 or other haptic devices. In some embodiments, the pressure-changing device 967 is a pneumatic device, hydraulic device, a pneudraulic device, or some other device capable of adding and removing a medium (e.g., fluid, liquid, gas) from the one or more haptic assemblies 962.

The memory 978 includes instructions and data, some or all of which may be stored as non-transitory computer-readable storage media within the memory 978. For example, the memory 978 can include one or more operating systems 979; one or more communication interface applications 981; one or more interoperability modules 984; one or more AR processing applications 985; and one or more data management modules 986; and/or any other types of data defined above or described with respect to FIGS. 6A-8B.

The memory 978 also includes data 988 which can be used in conjunction with one or more of the applications discussed above. The data 988 can include: device data 990; sensor data 991; and/or any other types of data defined above or described with respect to FIGS. 6A-8B.

The different components of the computing system 940 (and the smart textile-based garment 900) shown in FIGS. 9A-9C can be coupled via a wired connection (e.g., via busing). Alternatively, one or more of the devices shown in FIGS. 9A-9C may be wirelessly connected (e.g., via short-range communication signals).

Example System for Knitting Smart Textile-Based Garments

Figure 10:
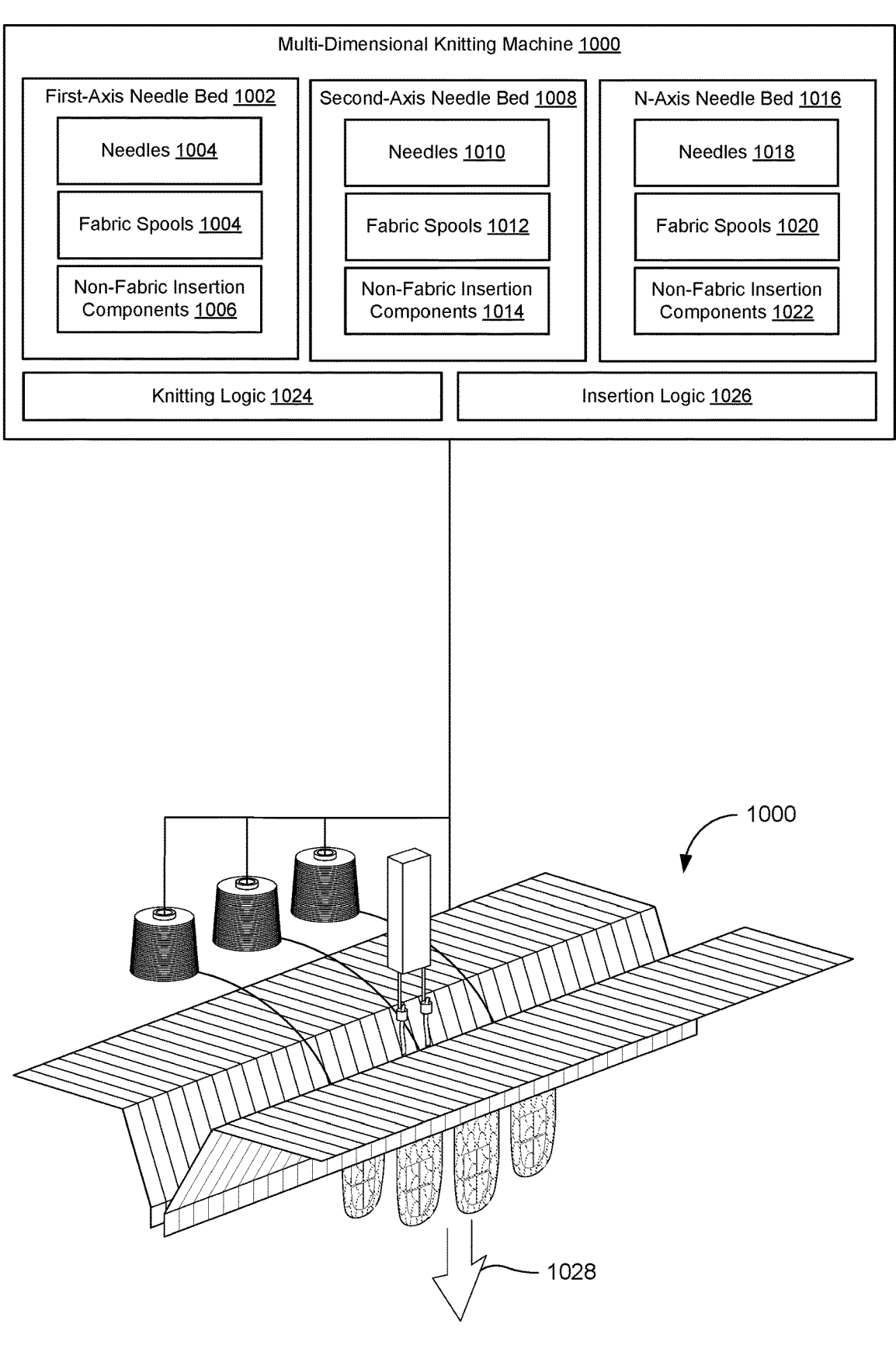
FIG. 10 illustrates a multi-dimensional knitting machine configured to produce multi-dimensional knitted smart textile-based garments in an automated fashion, in accordance with some embodiments.

Attention is now directed to FIG. 10, which illustrates a multi-dimensional knitting machine configured to produce multi-dimensional knitted garments in an automated fashion (e.g., with the needing for any hand knitting or other user intervention after initiating the knitting process, including allowing for having an electronic component automatically knitted as an integrated component of the multi-dimensional knitted garments), in accordance with some embodiments. The multi-dimensional knitting machine 1000 is a garment-producing device that is computer controlled and user programmable to allow for complex knitted structures to be produced (e.g., smart textile-based garments 900 (FIGS. 9A-9C); such as gloves, tubular fabrics, fabrics with embedded electronic devices, complex knit patterns, special stretch characteristics, unique pattern structures, multi-thread structures, etc.,). The multi-dimensional knitting machine 1000 includes a first-axis needle bed 1002, a second-axis needle bed 1008, and N-axis needle bed (indicating more than three needle beds are possible). Each one of these needle beds (e.g., needles 1004, needles 1010, and needles 1018) is configured to use multiple different types of knit patterns (e.g., jersey knits, rib knits, interlock knits, French-terry knits, fleece knits, etc.,) based on a programmed sequence providing to the multi-dimensional knitting machine 1000, and variations of these knits can be employed to form a single continuous garment (e.g., a combination of jersey knits and French terry knit and/or a first variation of a jersey knit and a second variation of a jersey knit). In some embodiments, the variations of these knits in a single continuous garment can be done without producing seams (e.g., a seamless wearable device can be produced). In some embodiments, the knitting machine is further configured to layer fabrics to produce multilayered wearable structures (e.g., to house one or more electronic components). In some embodiments, each layer in a multilayered wearable structure can be made from a different fabric, which in one example is produced using a conductive yarn. For example, a two-layer knitted capacitive sensor can be produced using the multi-dimensional knitting machine 1000, where the first layer and the second layer use different thread (e.g., a coated-conductive thread and an uncoated-conductive thread). A plurality of fabric spools (e.g., fabric spools 1004, fabric spools 1012, and fabric spools 1020) can be included for each one of the needle beds. Multiple types of fabric spools can be used for each needle bed allowing for even more complex woven structures (also referred to as garments) to be produced. In some embodiments, the fabric spools can also include elastic thread allowing for stretchable fabrics and/or fabrics with shape memory to be produced.

Each of the needle beds discussed above can also include one or more non-fabric insertion components (e.g., non-fabric insertion components 1006, non-fabric insertion components 1014, and non-fabric insertion components 1022) that are configured to be used to allow for insertion of non-fabric structures into the needle beds, such that the non-knitted structure can be knitted into the knitted structure, while the knitted structure (e.g., garment) is being produced. For example, non-fabric structures can include flexible printed circuit boards, rigid circuit boards, conductive wires, structural ribbing, sensors (e.g., neuromuscular signal sensors, light sensors, PPG sensors, etc.,), etc. In some embodiments, a stitch pattern can be adjusted by the multi-dimensional knitting machine (e.g., in accordance with a programmed sequence of knit instructions provided to the machine) to accommodate these structures, which, in some embodiments, means that these structures are knitted into the fabric, instead of being sewn on top of a knitted fabric. This allows for garments to be lighter, thinner, and more comfortable to wear (e.g., by having fewer protrusions applying uneven pressure to the wearer's skin). In some embodiments, these multi-dimensional knitting machines can also knit knitted structures along either or both of a vertical axis or a horizontal depending on desired characteristics of the knitted structure. Knitting along a horizontal axis means that the garment would be produced from a left side to a right side (e.g., a glove would be produced starting with the pinky finger, then moving to the ring finger, then middle finger, etc. Sewing on the vertical means that the garment is produced in a top-down fashion (e.g., a glove would be produced starting from the top of the tallest finger and move down to the wrist portion of the glove (e.g., as shown by 1028 in FIG. 10)). With respect to the glove examples, a reverse manufacturing process is also contemplated (e.g., knitting a thumb first when knitting on the horizontal and knitting the wrist portions when knitting on the vertical). In some embodiments, the insertion component can feed the non-knitted structure to the knitting machine or, in some other embodiments, the insertion component is fed through the knitting machine with the non-knitted structure. In the latter, the insertion component is not integrated into the garment and is discarded. In some embodiments, the insertion component is not fed at all, but is an integrated component of the multi-dimensional knitting machine that is activated based on a programming knit sequence to then allow for insertion of a non-knitting component into a knitted structure.

The multi-dimensional knitting machine 1000 also includes knitting logic module 1024, which is a module that is user programmable to allow for a user (which can be a manufacturing entity producing wearable structures on mass scale) to define a knitting sequence to produce a garment using any of the above-described materials, stitch patterns, knitting techniques, etc. As stated above, the knitting logic module 1024 allows for a seamless combination of any of the above-described techniques, thereby allowing unique complex knitted structures to be produced in a single knitting sequence (e.g., the user does not need to remove the knitted structure, then reinsert and reorient it to complete knitting the knitted structure). The multi-dimensional knitting machine 1000 also includes insertion logic module 1026, which works in tandem with the knitting logic module

1024, to allow for insertion of non-fabric components to be seamlessly inserted into the knitted structure while the knitted structure is knitted together. The insertion logic is in communication with the knitting logic to allow for the knit to be adjusted in accordance with where the non-fabric structure is being inserted. In some embodiments, the user need only show where the non-fabric structure is to be inserted in their mock-up (e.g., at a user interface associated with the multi-dimensional knitting machine, which user interface allows for creating and editing a programmed knit sequence) and the knitting logic module 1024 and insertion logic module 1026 automatically work together to allow for the knitted structure to be produced.

Any data collection performed by the devices described herein and/or any devices configured to perform or cause the performance of the different embodiments described above in reference to any of the Figures, hereinafter the "devices," is done with user consent and in a manner that is consistent with all applicable privacy laws. Users are given options to allow the devices to collect data, as well as the option to limit or deny collection of data by the devices. A user is able to opt-in or opt-out of any data collection at any time. Further, users are given the option to request the removal of any collected data.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" can be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" can be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

53

54

What is claimed is:

1. A method of securing a wearable device to a user, the method including:

while the wearable device is worn around a body part of a user, the wearable device including a biopotential-signal sensor configured to receive a biopotential signal and the biopotential-signal sensor is connected to an amplifier to adjust amplification of the biopotential signal to a particular amplitude for signal processing:

receiving first information representative of power needed to amplify the biopotential signal to the particular amplitude for signal processing;

in accordance with a determination that the first information representative of the power needed to amplify the biopotential signal to the particular amplitude for signal processing indicates that the wearable device is not properly affixed to the body part of the user, providing first instructions to adjust how the wearable device is affixed to the body part of the user; and receiving second information representative of power needed to amplify the biopotential signal to the particular amplitude for signal processing;

in accordance with a determination that the second information representative of the power needed to amplify the biopotential signal to the particular amplitude for signal processing indicates that the wearable device is properly affixed to the body part of the user, forgoing providing second instructions to adjust how the wearable device is affixed to the body part of the user.

2. The method of claim 1, wherein providing first instructions to adjust how the wearable device is affixed to the body part of the user includes providing instructions as to tightening or loosening the wearable device around the body part.

3. The method of claim 1, wherein providing the first instructions to adjust how the wearable device is affixed to the body part of a user includes causing display of a visual alert.

4. The method of claim 3, wherein the visual alert is displayed via a display device of the wearable device.

5. The method of claim 1, wherein the wearable device is in communication with another electronic device that includes a display, and the providing of the first instructions occurs at the display of the other electronic device.

6. The method of claim 1, wherein the wearable device includes post-amplifier signal processing components, and the method includes:

while the wearable device is worn around the body part of the user:

in accordance with the determination that the first information representative of the power needed to amplify the biopotential signal to the particular amplitude for signal processing indicates that the wearable device is not properly affixed to the body part of the user, forgoing processing biopotential signal data by the post-amplifier signal processing components.

7. The method of claim 1, wherein the wearable device includes post-amplifier signal processing components, and the method includes:

while the wearable device is worn around the body part of the user:

in accordance with the determination that the second information representative of the power needed to amplify the biopotential signal to the particular amplitude for signal processing indicates that the wearable device is properly affixed to the body part of the user, processing biopotential signal data by the post-amplifier signal processing components.

8. The method of claim 1, wherein the wearable device includes an automatic-wrist-fit adjusting mechanism, the method includes:

before receiving the second information, receiving, at the automatic-wrist-fit adjusting mechanism, the first instructions to adjust how the wearable device is affixed to the body part of the user; and in response to receiving the first instructions, automatically adjusting a fit characteristic of the wearable device.

9. The method of claim 8, the determination that the second information representative of the power needed to amplify the biopotential signal to the particular amplitude for signal processing indicates that the wearable device is properly affixed to the body part of the user is made after adjusting the fit characteristic of the wearable device.

10. The method of claim 8, wherein the automatically adjusting a fit characteristic of the wearable device occurs via a linear actuator or by adjusting a skin-depression depth associated with the biopotential-signal sensor.

11. The method of claim 8, including automatically adjusting the fit characteristic until a further determination is made that the wearable device is properly affixed to the body part of the user, and when the further determination is made, ceasing to further adjust how the wearable device is affixed to the body part of the user.

12. The method of claim 1, wherein the first information representative of the power needed to amplify the biopotential signal to the particular amplitude for signal processing includes a measurement of an average current being used to amplify signals detected by the biopotential-signal sensor.

13. The method of claim 12, wherein the measurement of average current being sent to the biopotential-signal sensor exceeds 50 milliamps.

14. The method of claim 1, wherein the second information representative of the power needed to amplify the biopotential signal to the particular amplitude for signal processing includes a measurement of an average current being used to amplify signals detected by the biopotential-signal sensor.

15. The method of claim 14, wherein the measurement of average current being sent to the biopotential-signal sensor does not meet 30 microamps.

16. The method of claim 1, wherein the wearable device is a wrist-wearable device, and the body part of the user is a wrist.

17. The method of claim 1, wherein the biopotential-signal sensor is a neuromuscular signal sensor configured to receive a neuromuscular signal.

18. A non-transitory computer readable storage medium including instructions that, when executed by a computing device in communication with a wearable device, cause the computing device to:

while the wearable device is worn around a body part of a user, the wearable device including a biopotential-signal sensor configured to receive a biopotential signal and the biopotential-signal sensor is connected to an amplifier to adjust amplification of the biopotential signal to a particular amplitude for signal processing:

receive first information representative of power needed to amplify the biopotential signal to the particular amplitude for signal processing;

in accordance with a determination that the first information representative of the power needed to amplify the biopotential signal to the particular amplitude for signal processing indicates that the wearable device is not properly affixed to the body part of the user, provide first instructions to adjust how the wearable device is affixed to the body part of the user; and receive second information representative of power needed to amplify the biopotential signal to the particular amplitude for signal processing;

in accordance with a determination that the second information representative of the power needed to amplify the biopotential signal to the particular amplitude for signal processing indicates that the wearable device is properly affixed to the body part of the user, forgo providing second instructions to adjust how the wearable device is affixed to the body part of the user.

19. A wearable device, comprising:

memory; and one or more programs, wherein the one or more programs are stored in the memory and configured to be executed by one or more processors of the wearable device, the one or more programs including instructions for:

while the wearable device is worn around a body part of a user, the wearable device including a biopotential-signal sensor configured to receive a biopotential signal and the biopotential-signal sensor is connected to an amplifier to adjust amplification of the biopotential signal to a particular amplitude for signal processing:

receiving first information representative of power needed to amplify the biopotential signal to the particular amplitude for signal processing;

in accordance with a determination that the first information representative of the power needed to amplify the biopotential signal to the particular amplitude for signal processing indicates that the wearable device is not properly affixed to the body part of the user, providing first instructions to adjust how the wearable device is affixed to the body part of the user; and receiving second information representative of power needed to amplify the biopotential signal to the particular amplitude for signal processing;

in accordance with a determination that the second information representative of the power needed to amplify the biopotential signal to the particular amplitude for signal processing indicates that the wearable device is properly affixed to the body part of the user, forgoing providing second instructions to adjust how the wearable device is affixed to the body part of the user.

* * * * *